(12) United States Patent
Ansari et al.

(10) Patent No.: US 11,759,533 B2
(45) Date of Patent: Sep. 19, 2023

(54) METHODS AND COMPOSITIONS FOR MODULATING GENE EXPRESSION

(71) Applicant: Wisconsin Alumni Research Foundation, Madison, WI (US)

(72) Inventors: Aseem Ansari, Madison, WI (US); Graham Erwin, Indianapolis, IN (US); Matthew Grieshop, New Berlin, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 747 days.

(21) Appl. No.: 15/940,183

(22) Filed: Mar. 29, 2018

(65) Prior Publication Data
US 2018/0280541 A1    Oct. 4, 2018

Related U.S. Application Data

(60) Provisional application No. 62/478,291, filed on Mar. 29, 2017.

(51) Int. Cl.
| | |
|---|---|
| *A61K 48/00* | (2006.01) |
| *C12N 15/11* | (2006.01) |
| *A61K 31/5517* | (2006.01) |
| *C07D 495/14* | (2006.01) |
| *A61K 47/59* | (2017.01) |
| *A61P 43/00* | (2006.01) |
| *A61K 47/54* | (2017.01) |
| *C12N 15/00* | (2006.01) |
| *A61K 47/60* | (2017.01) |

(52) U.S. Cl.
CPC ...... *A61K 48/0066* (2013.01); *A61K 31/5517* (2013.01); *A61K 47/545* (2017.08); *A61K 47/595* (2017.08); *A61K 48/0041* (2013.01); *A61P 43/00* (2018.01); *C07D 495/14* (2013.01); *C12N 15/00* (2013.01); *C12N 15/11* (2013.01); *A61K 47/60* (2017.08); *C12N 2310/113* (2013.01); *C12N 2310/152* (2013.01); *C12N 2310/343* (2013.01); *C12N 2310/3513* (2013.01); *C12N 2310/3519* (2013.01)

(58) Field of Classification Search
CPC .............. A61K 31/5517; A61K 47/545; A61K 47/595; A61K 47/60; A61K 48/0041; A61K 48/0066; A61P 43/00; C07D 495/14; C12N 15/00; C12N 15/11; C12N 2310/113; C12N 2310/152; C12N 2310/343; C12N 2310/3513; C12N 2310/3519
USPC ...................................................... 435/375
See application file for complete search history.

(56) References Cited

U.S. PATENT DOCUMENTS

| | | | |
|---|---|---|---|
| 5,712,274 A | 1/1998 | Sueoka et al. | |
| 6,090,647 A | 7/2000 | Dervan et al. | |
| 6,545,162 B1 | 4/2003 | Dervan et al. | |
| 6,555,692 B1* | 4/2003 | Dervan | .............. C07K 7/02 548/518 |
| 6,559,125 B1 | 5/2003 | Dervan et al. | |
| 6,660,255 B1 | 12/2003 | Gottesfeld et al. | |
| 7,452,730 B2 | 11/2008 | Dervan et al. | |
| 8,044,042 B2 | 10/2011 | Adachi et al. | |
| 8,476,260 B2 | 7/2013 | Miyoshi et al. | |
| 8,835,502 B2 | 9/2014 | Gottesfeld et al. | |
| 8,981,083 B2 | 3/2015 | Bradner et al. | |
| 9,000,009 B2 | 4/2015 | Wilson et al. | |
| 9,066,966 B2 | 6/2015 | Puccio et al. | |
| 9,125,881 B2 | 9/2015 | Henderson | |
| 9,169,196 B2 | 10/2015 | Jankowski et al. | |
| 9,217,019 B2 | 12/2015 | Testi | |
| 9,227,985 B2 | 1/2016 | Combs et al. | |
| 9,301,962 B2 | 4/2016 | Bradner et al. | |
| 9,320,741 B2 | 4/2016 | Bradner et al. | |
| 9,399,640 B2 | 7/2016 | Yue et al. | |
| 9,458,156 B2 | 10/2016 | Norris et al. | |
| 9,492,460 B2 | 11/2016 | Poss et al. | |
| 10,517,877 B2* | 12/2019 | Ansari | ................ C07D 495/14 |
| 2005/0123936 A1 | 6/2005 | Ansari et al. | |
| 2006/0270727 A1* | 11/2006 | Melander | ........... A61K 31/4178 514/397 |
| 2010/0016172 A1 | 1/2010 | Ansari et al. | |
| 2010/0159457 A1 | 6/2010 | Warren et al. | |

(Continued)

FOREIGN PATENT DOCUMENTS

| | | |
|---|---|---|
| WO | 0234295 | 5/2002 |
| WO | 2007058927 | 5/2007 |

(Continued)

OTHER PUBLICATIONS

CN: 1-BET-151; Registry No. 1300031-49-5. May 24, 2011. (Year: 2011).*
CN: I-BET-762; Registry No. 1260907-17-2. Jan. 28, 2011. (Year: 2011).*
CN: JQ1; Registry No. 1268524-70-4. Mar. 15, 2011. (Year: 2011).*
Eguchi et al. Biochem. J. (2014) 462, 397-413. (Year: 2014).*
PCTUS2017024745 International Search Report and Written Opinion, filing date Mar. 29, 2017, 13 pages.

(Continued)

*Primary Examiner* — Janet L Epps-Smith
(74) *Attorney, Agent, or Firm* — Daniel A. Blasiole; DeWitt LLP

(57) ABSTRACT

The present technology relates to compositions and methods for modulating expression of genes which include a target oligonucleotide sequence, such as repeats of a particular oligonucleotide sequence containing 3 to 10 nucleotides. In particular aspects, the present technology relates to agents having a formula A-L-B, wherein -L- is a linker; A- is a Brd4 binding moiety; and —B is a nucleic acid binding moiety, such as a polyamide or complementary oligonucleotide, that specifically binds to the target oligonucleotide sequence.

30 Claims, 18 Drawing Sheets
(10 of 18 Drawing Sheet(s) Filed in Color)
Specification includes a Sequence Listing.

(56) References Cited

U.S. PATENT DOCUMENTS

| | | |
|---|---|---|
| 2013/0210813 A1 | 8/2013 | Bradner et al. |
| 2013/0252331 A1 | 9/2013 | Bradner et al. |
| 2014/0011862 A1 | 1/2014 | Bradner et al. |
| 2015/0051208 A1 | 2/2015 | Engelhardt et al. |
| 2015/0133447 A1 | 5/2015 | Engelhardt |
| 2016/0033519 A1 | 2/2016 | Bradner et al. |
| 2016/0193218 A1 | 7/2016 | Quinn et al. |
| 2016/0201063 A1 | 7/2016 | Ozsolak et al. |
| 2017/0065719 A1 | 3/2017 | Qian et al. |
| 2017/0281643 A1 | 10/2017 | Ansari et al. |

FOREIGN PATENT DOCUMENTS

| | | | |
|---|---|---|---|
| WO | 2011143651 | 11/2011 | |
| WO | 2011143657 | 11/2011 | |
| WO | 2011143669 | 11/2011 | |
| WO | 2011143660 | 4/2012 | |
| WO | 2014159392 | 10/2014 | |
| WO | 2015015318 | 2/2015 | |
| WO | 2015022332 | 2/2015 | |
| WO | 2015023938 | 2/2015 | |
| WO | 2015067770 | 5/2015 | |
| WO | WO-2016145014 A1 * | 9/2016 | ......... A61K 31/4164 |
| WO | 2017030814 | 2/2017 | |
| WO | 2017031416 | 2/2017 | |
| WO | 2017037567 | 3/2017 | |
| WO | 2017172914 | 10/2017 | |

OTHER PUBLICATIONS

Ansari AZ, Mapp AK, Nguyen DH, Dervan PB, Towards a minimal motif for artificial transcriptional activators, Ptashne M, Chem Biol. (2001 )8, 583-592.

Arndt HD, Toward artificial developmental regulators,(2003) J Am Chem Soc. 125, 13322-13323.

Arora PS, Design of artificial transcriptional activators with rigid poly-L-proline linkers,(2002), J Am Chem Soc. 124, 13067-13071.

Baird, E.E. et al., Solid Phase Synthesis of Polyamides Containing Imidazole and Pyrrole Amino Acids, (1996), J. Am. Chem. Soc. 118, pp. 6141-6146.

Burnett et al., DNA sequence-specific polyamides alleviate transcription inhibition associated with long GAA-TTC repeats in Friedreich's ataxia, PNAS, (2006), 103, 31, 11497-11502.

Butler et al., Friedreich's ataxia—a case of aberrant transcription termination? Transcription,(2015), 6:2, 33-36.

Carlson CD, Specificity landscapes of DNA binding molecules elucidate biological function,(2010), 107, 4544-4549.

Delmore et al., BET Bromodomain Inhibition as a Therapeutic Strategy to Target c-Myc, Cell, (2011), 146, 6, 904.

Dervan, Molecular Recognition of DNA by Small Molecules, Bioorganic & Medicinal Chemistry, (2001 ), vol. 9, 2215-2235.

Eguchi et al., Controlling gene networks and cell fate with precision-targeted DNA-binding proteins and small-molecule-based genome readers, Biochem J., 2014, 462, 397.

Erwin et al., Genome-wide Mapping of Drug-DNA Interactions in Cells with COSMIC Crosslinking of Small Molecules to Isolate Chromatin, J. Vis. Exp., 2016, 107, e53510.

Erwin et al., Mapping polyamide-DNA interactions in human cells reveals a new design strategy for effective targeting of genomic sites, Angew. Chem. Int. Ed., 2014, 53, 10124.

Erwin et al., Synthetic genome readers target clustered binding sites across diverse chromatin states, PNAS, Nov. 22, 2016 vol. 113.

Filippakopoulos, Selective Inhibition of BET bromodomains, JQ1 synthesis, Nature, Dec. 23, 2010; 468 (7327): 1067-1073.

Finley et al., Small Molecule Control of Chromatin Remodeling, Chemistry & Biology, 2014, 21, 1196-1210.

Gakh et al., Normal and Friedreich ataxia cells express different isorforms of frataxin with complementary roles in iron-sulfer cluster assembly, J. Biolog. Chem., (2010), 285(49), 38486-38501.

Sottesfeld et al., Increasing frataxin gene expression with histone deacetylase inhibitors as a therapeutic approach for Freidreich's ataxia, Jornal of Neurochemistry, vol. 126, Jul. 17, 2013, pp. 14 7-154, XP055383276, New York, NY, US.

Groh et al., R-loops Associated with Triplet Repeat Expansions Promote Gene Silencing in Friedreich Ataxia and Fragile X Syndrome, PLoS Genetics, 2014, 10(5), e1004318.

Harding, A.E., Friedreich's Ataxia: A clinical and genetic study of 90 families with an analysis of early diagnostic criteria and intrafamilial clustering of clinical features, Brain, 1981, 104:589-620.

Hauschild KE, Temperature-sensitive protein-DNA dimerizers, PNAS, 2005, 102, 5008-5013.

Herman et al., Histone deacetylase inhibitors reverse gene silencing in Friedreich's ataxia, Nat. Chem. Biol. 2006, 2, 551-558.

Jacoby, D. et al., Epigenetic Therapy for Friedreich's ataxia: A Phase I Clinical Trial (PL 1.003), 2014, Neurology, vol. 82, No. 10 supplement PL 1003. (Abstract only.).

Janssen, Chromatin Opening of DNA satellites by targeted sequence-specific drugs, Molecular Cell, Nov. 2000, vol. 6, 999-1011.

Li et al., Expanded GAA repeats impede transcription elongation through the FXN gene and induce transcriptional silencing that is restricted to the FXN locus, Hum. Mol. Genet. 2015, 24, 24, 6932-6943.

Lu Fino et al., GAA repeat expansion reporter model of Friedreich's ataxia, Hum. Mol. Genet., 2013, 22 (25): 5173-5187.

Mapp AK, Activation of gene expression by small molecule transcription factors, Proc Natl Acad Sci USA 97, 2000 3930-3935.

Polak et al., Expanded complexity of unstable repeat diseases, BioFactors, 2013, 39(2): 164-175.

Puckett et al., Quantitative microarray profiling of DNA-binding molecules, J Am Chem Soc., 2007, 129, 12310-12319.

Punga et al., Long itronic GAA repeats causing Friedreich ataxia impede transcription elongation, EMBO Mol. Med., 2010, 2, 120-129.

Rodriguez-Martinez et al, Small-molecule regulators that mimic transcription factors, Biochim Biophys Acta., 2010,(10-12):768-74.

Silva et al., Expanded GAA repeats impair FXN gene expression and reposition the FXN locus to the nuclear amina in single cells, Hum. Mol. Genet., 2015, 24, 12, 3457.

Soragni et al., Mechanism of Action of 2-Aminobenzamide HDAC inhibitors in reversing gene silencing in Friedreich's ataxia, Front. Neurol. 2015, 6: 44.

Sorgani et al., Epigenetic therapty for Friedreich ataxia: Epigenetic Therapy for FRDA, Annals of Neurology, vol. 76, No. 4, Sep. 16, 2014, pp. 489-508, XP055383280, Boston, US.

Stafford et al, Minimization of a protein-DNA dimerizer, J Am Chem Soc., 2007, 129, 2660-2668.

Weidemann, et al., The cardiomyopathy in Friedreich's ataxia—New biomarker for staging cardiac involvement, Intl. J. Cardiol., 2015, 194:50-57.

Wood, N.W., FRDA diagnosis—clinical criteria and genetic testing, Arch. Dis. Child., 1998, 78:204-207.

Yang, et al., Antitumor activity of a pyrrole-imidazole polyamide, PNAS, Jan. 29, 2013, vol. 110, No. 5, pp. 1863-1868.

Hersh, et al., Clinical Report—Health supervision for children with Fragile X Syndrome, Pediatrics, 127:994-1006 (2011).

Lee, et al., Pathogenic mechanisms of myotonic dystrophy, Biochem. Soc. Trans., 37(6): 1281-1286 (2009).

Nelson, et al., The unstable repeats—three evolving faces of neurological disease, Neuron, 77(5):825-843 (2013).

Warren et al., Defining the sequence-recognition profile of DNA-binding molecules, PNAS, 2006, 103(4) 867.

Erwin et al. "Synthetic transcription elongation factors license transcription across repressive chromatin," Science, 358(6370):1617-1622, 2017.

International Search Report and Written Opinion for PCT/US2018/025147, 17 pages, dated Jun. 7, 2018.

* cited by examiner

2 = Control Conjugate 2
3 = Polyamide 3
4 = Agent 4

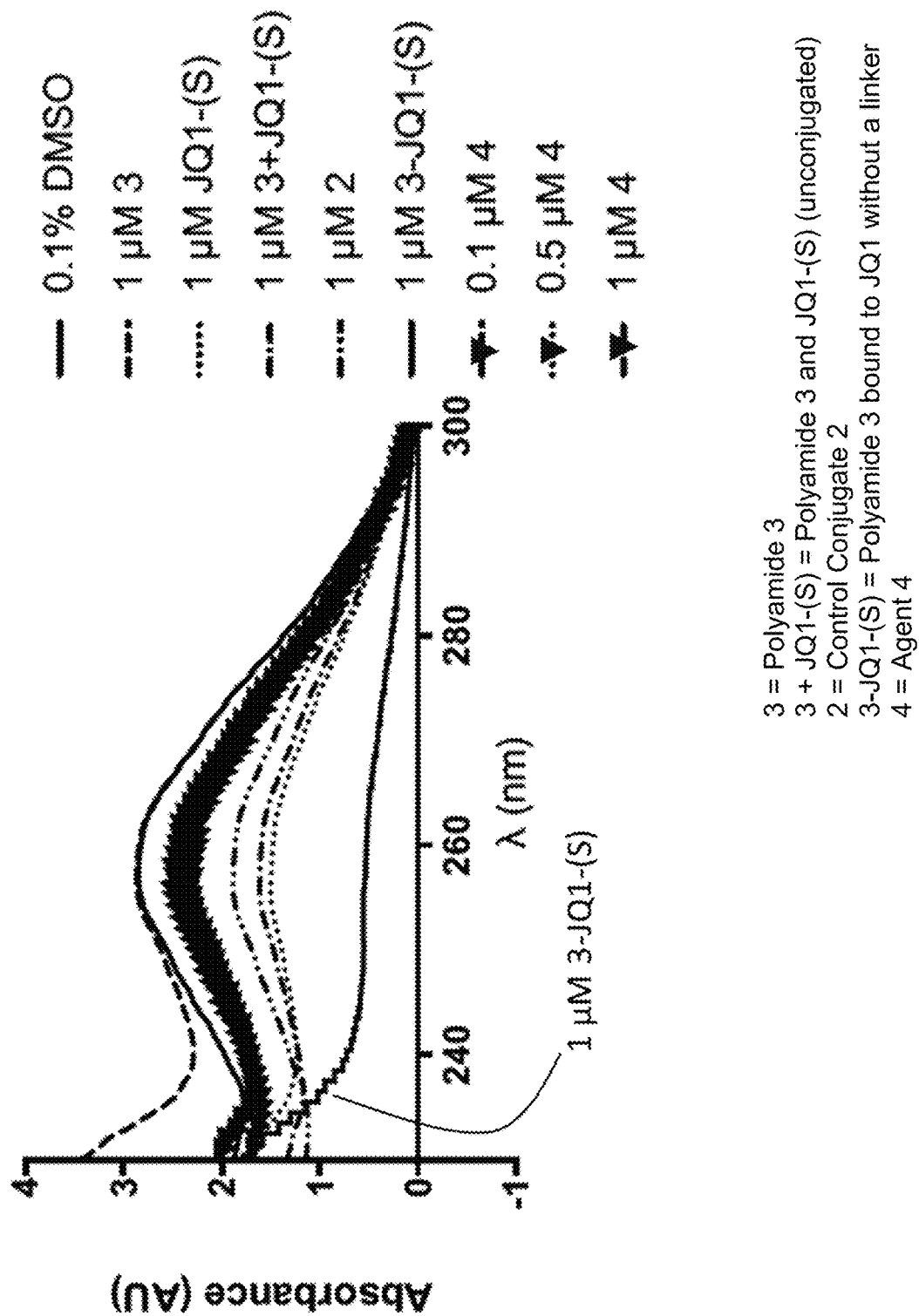

Scheme 1

Scheme 2

Scheme 3

Scheme 4 - Exemplary Polyamides

Scheme 5 - Coupling of Subunit A- and linker -L-

Scheme 6 - coupling of Subunit A-L- and subunit -B

METHODS AND COMPOSITIONS FOR MODULATING GENE EXPRESSION

CROSS-REFERENCE TO RELATED APPLICATIONS

This application claims priority to U.S. Provisional Application Ser. No. 62/478,291, filed Mar. 29, 2017, which is incorporated herein by reference in its entirety.

STATEMENT OF GOVERNMENT INTEREST

This invention was made with government support under CA133508 and HL099773 awarded by the National Institutes of Health. The government has certain rights in the invention.

BACKGROUND

Expanded oligonucleotide repeat sequences, such as dinucleotide, trinucleotide, tetranucleotide, pentanucleotide, and hexanucleotide repeats, that are contiguously repeated in genomic stretches of deoxyribonucleic acid (DNA) can lead to disease. Examples of diseases and disorders involving expanded oligonucleotide repeat sequences include Friedreich's ataxia (FR or FRDA), Fragile X syndrome (FXS), Fragile X-associated tremor/ataxia syndrome (FXTAS), myotonic dystrophy type 1 (DM type 1), and myotonic dystrophy type 2 (DM type 2). In some cases, expansions may comprise more than 1000 repeats. Expanded oligonucleotide repeat sequences may be found in regions within the transcription unit of a gene, including the DNA coding sequence (introns and exons) as well as DNA regions corresponding to the 5' and 3' untranslated regions (5' UTR and 3' UTR, respectively) of the transcribed mRNA, or in regions of the genome not associated with a gene. Recent evidence suggests that pausing of RNA polymerase-II at genes having expanded oligonucleotide repeats plays a role in disease pathogenesis at the molecular level, thereby inhibiting transcriptional elongation.

Many diseases, for example diseases discussed herein, are characterized by expanded oligonucleotide repeat sequences at different locations and degrees of expansion within the genome. Such repeats can occur throughout all genomic sequences. FRDA is characterized by an abnormal expansion of the guanine-adenine-adenine (GAA) trinucleotide repeat sequence in intron 1 of the frataxin (FXN) gene, resulting in transcriptional repression and reduced expression of the frataxin (FXN) protein. FXS is characterized by an abnormal expansion of the cytosine-guanine-guanine (CGG) trinucleotide repeat sequence in the region of the Fragile X Mental Retardation 1 (FMR1) gene corresponding to the 5' UTR of the transcribed FMR1 mRNA, resulting in transcriptional repression and reduced expression of the FMRP, which is the protein encoded by FMR1. FXTAS is characterized by an abnormal expansion of the cytosine-guanine-guanine (CGG) trinucleotide repeat sequence in the region of the Fragile X Mental Retardation 1 (FMR1) gene corresponding to the 5' UTR of the transcribed FMR1 mRNA, which may result in transcriptional repression and reduced expression of the FMRP, which is the protein encoded by FMR1. Myotonic dystrophy type 1 (DM type 1) is characterized by an abnormal expansion of the cytosine-thymine-guanine (CTG) trinucleotide repeat sequence in the region of the dystrophia myotonica protein kinase (DMPK) gene corresponding to the 3' UTR of the transcribed DMPK mRNA, which may result in transcriptional repression and reduced expression of the DMPK protein. Myotonic dystrophy type 2 (DM type 2) is characterized by an abnormal expansion of the cytosine-cytosine-thymine-guanine (CCTG) tetranucleotide repeat sequence in the region of the CNBP (ZNF9 or zinc finger 9) gene corresponding to intron 1, which may result in transcriptional repression and reduced expression of the CNBP (ZNF9 or zinc finger 9) protein. Without wishing to be bound by theory, it is generally understood that hyper-expansion of oligonucleotide repeat sequences located within the genomic nucleotide sequence of a disease gene results in decreased transcription of the gene and lower levels of protein relative to an individual without hyper-expansion of the oligonucleotide repeat sequences. The decreased protein levels result in disease.

Presently, there is neither a cure for FRDA, FXTAS, FXS, DM type 1, or DM type 2, nor a specific therapy, which has been approved for use as a treatment, to prevent progression of the disease. Therefore, there is a need to develop compositions to modulate the genes in these diseases for treatment and prevention.

SUMMARY

The present technology relates generally to compositions and methods for modulating expression of genes which include a target oligonucleotide sequence, such as repeats of an oligonucleotide sequence having 3 to 10 nucleotides. In a particular aspect, the present technology relates to agents having a formula A-L-B wherein -L- is a linker; A- is a Brd4 binding moiety; and —B is a nucleic acid binding moiety that binds to a specific target oligonucleotide sequence. In some embodiments, —B is a polyamide that specifically binds to the target oligonucleotide sequence. In some embodiments, —B is a second oligonucleotide sequence that specifically binds to the target oligonucleotide sequence. In some embodiments, the target oligonucleotide sequence comprises one or more repeats of an oligonucleotide sequence having 3 to 10 nucleotides. In some embodiments, —B is a polyamide that specifically binds to one or more repeats of an oligonucleotide sequence having 3 to 10 nucleotides.

In one aspect, the present technology provides compositions and methods for modulating expression of genes which include repeats of an oligonucleotide sequence having 3 to 10 nucleotides, such as repeats of a GAA, CGG, CTG, or CCTG oligonucleotide sequence. In some embodiments, the present technology relates to agents having a formula A-L-B, wherein -L- is a linker; A- is a Brd4 binding moiety; and —B is a polyamide that specifically binds to one or more repeats of a GAA oligonucleotide sequence and methods of use. In some embodiments, the present technology relates to agents having a formula A-L-B, wherein -L- is a linker; A- is a Brd4 binding moiety; and —B is a polyamide that specifically binds to one or more repeats of a CGG oligonucleotide sequence and methods of use. In some embodiments, the present technology relates to agents having a formula A-L-B, wherein -L- is a linker; A- is a Brd4 binding moiety; and —B is a polyamide that specifically binds to one or more repeats of a CTG oligonucleotide sequence and methods of use. In some embodiments, the present technology relates to agents having a formula A-L-B, wherein -L- is a linker; A- is a Brd4 binding moiety; and —B is a polyamide that specifically binds to one or more repeats of a CCTG oligonucleotide sequence and methods of use.

Disclosed herein are methods and compositions for modulating gene expression. In one aspect, the compositions comprise any one or more of the agents shown in Section IV. In some embodiments, the agent has a formula A-L-B, wherein -L- is a linker; A- is a Brd4 binding moiety; and —B is polyamide that specifically binds to one or more repeats of an oligonucleotide sequence containing 3 to 10 nucleotides, such as a GAA oligonucleotide sequence. In some embodiments, the agent has a formula A-L-B, wherein -L- is a linker; A- is a Brd4 binding moiety; and —B is polyamide that specifically binds to one or more repeats of an oligonucleotide sequence containing 3 to 10 nucleotides, such as a CGG oligonucleotide sequence. In some embodiments, the agent has a formula A-L-B, wherein -L- is a linker; A- is a Brd4 binding moiety; and —B is polyamide that specifically binds to one or more repeats of an oligonucleotide sequence containing 3 to 10 nucleotides, such as a CTG oligonucleotide sequence. In some embodiments, the agent has a formula A-L-B, wherein -L- is a linker; A- is a Brd4 binding moiety; and —B is polyamide that specifically binds to one or more repeats of an oligonucleotide sequence containing 3 to 10 nucleotides, such as a CCTG oligonucleotide sequence.

In some embodiments, A may be a triazolodiazepine Brd4 binding moiety or related structure, such as a thienotriazolodiazepine Brd4 binding moiety.

In some embodiments, the agent is capable of increasing mRNA expression levels of a gene wherein the gene comprises at least about 30 repeats, and in some instances at least about 50 repeats of an oligonucleotide sequence having 3 to 10 nucleotides, e.g., increasing gene mRNA levels in a cell derived from a subject suffering from a genetic condition associated with a gene comprising a plurality of repeats of a GAA oligonucleotide sequence. In some embodiments, the agent is capable of increasing mRNA expression levels of a gene which includes repeats of a GAA oligonucleotide sequence, e.g., increasing frataxin mRNA levels in a cell derived from a Friedreich's ataxia (FRDA) patient. In some embodiments, the agent is capable of increasing frataxin mRNA levels in a GM15850 FRDA patient cell line relative to an untreated GM15850 cell. In some embodiments, the agent is capable of inducing at least about a 2.5-fold increase in frataxin mRNA levels in a GM15850 FRDA patient cell line relative to an untreated GM15850 cell line. In some embodiments, the agent is capable of inducing at least about a 4-fold increase in frataxin mRNA levels in a GM15850 FRDA patient cell line relative to an untreated GM15850 cell line. In some embodiments, the agent is capable of inducing at least about a 6-fold increase in frataxin mRNA levels in a GM15850 FRDA patient cell line relative to an untreated GM15850 cell line. In some embodiments, the agent is capable of inducing at least about an 8-fold increase in frataxin mRNA levels in a GM15850 FRDA patient cell line relative to an untreated GM15850 cell line.

In some embodiments, the agent is capable of increasing mRNA expression levels of a gene which includes repeats of a CGG oligonucleotide sequence, e.g., increasing mRNA levels in a cell derived from a Fragile X syndrome (FXS) patient. In some embodiments, the agent is capable of increasing mRNA expression levels of a gene which includes repeats of a CGG oligonucleotide sequence, e.g., increasing mRNA levels in a cell derived from a Fragile X-associated tremor/ataxia syndrome (FXTAS) patient. In some embodiments, the agent is capable of increasing mRNA expression levels of a gene which includes repeats of a CTG oligonucleotide sequence, e.g., increasing mRNA levels in a cell derived from a myotonic dystrophy type 1 (DM type 1). In some embodiments, the agent is capable of increasing mRNA expression levels of a gene which includes repeats of a CCTG oligonucleotide sequence, e.g., increasing mRNA levels in a cell derived from a myotonic dystrophy type 2 (DM type 2).

In one aspect, the present disclosure provides a pharmaceutical composition comprising a therapeutically effective amount of any one or more of the agents described in Section IV and a pharmaceutically acceptable carrier. In some embodiments the pharmaceutically acceptable carrier is selected from one or more of saline, solvents, dispersion media, coatings, antibacterial and antifungal agents, isotonic and absorption delaying agents compatible with pharmaceutical administration. In some embodiments, the therapeutically effective amount of the agent is between 0.1 mg/kg to about 7.5 mg/kg body weight of a subject in need thereof.

In one aspect, the present disclosure provides a method for modulating transcription of a gene that includes multiple repeats of an oligonucleotide sequence containing 3 to 10 nucleotides, such as a GAA, CGG, CTG, or CCTG oligonucleotide repeat expansion. Without wishing to be bound by theory, the modulation of transcription is effected by contacting the gene with an agent of the present technology having a formula A-L-B, wherein -L- is a linker; A- is a Brd4 binding moiety; and —B is a polyamide that specifically binds to one or more repeats of the oligonucleotide sequence, thereby modulating the transcription of the gene.

In one aspect, the present disclosure provides a method for modulating mRNA levels in a cell, comprising contacting the cell with an effective amount of any one or more of the agents shown in Section IV, wherein the mRNA is encoded by a gene comprising at least about 50 repeats of an oligonucleotide sequence having 3 to 10 nucleotides. In one aspect, the present disclosure provides a method for increasing mRNA levels in a cell comprising contacting the cell with an effective amount of any one or more of the agents shown in Section IV, wherein the mRNA is encoded by a gene comprising at least about 50 repeats of an oligonucleotide sequence having 3 to 10 nucleotides. In one aspect, the present disclosure provides a method for increasing frataxin (FXN) mRNA levels in a cell comprising contacting the cell with an effective amount of any one or more of the agents shown in Section IV. In one aspect, the present disclosure provides a method for increasing Fragile X Mental Retardation 1 (FMR1) mRNA levels in a cell comprising contacting the cell with an effective amount of any one or more of the agents shown in Section IV. In one aspect, the present disclosure provides a method for increasing dystrophia myotonica protein kinase (DMPK) mRNA levels in a cell comprising contacting the cell with an effective amount of any one or more of the agents shown in Section IV. In one aspect, the present disclosure provides a method for increasing CNBP (ZNF9 or zinc finger 9) mRNA levels in a cell comprising contacting the cell with an effective amount of any one or more of the agents shown in Section IV. In another aspect, the present disclosure provides a method for increasing frataxin protein levels in a cell, comprising contacting the cell with an effective amount of any one or more of the agents shown in Section IV. In another aspect, the present disclosure provides a method for increasing FMRP protein levels in a cell, comprising contacting the cell with an effective amount of any one or more of the agents shown in Section IV. In another aspect, the present disclosure provides a method for increasing dystrophia myotonica protein kinase (DMPK) protein levels in a cell, comprising contacting the cell with an effective amount of any one or more of the agents shown in Section IV. In another aspect, the present disclosure provides a method for increasing CNBP protein levels in a cell, comprising contacting the cell with an effective amount of any one or more of the agents shown in Section IV. In some embodiments, the cell may be derived from a Friedreich's ataxia patient. In some embodiments, the cell may be derived from a Fragile X syndrome (FXS) patient. In some embodiments, the cell may be derived from a Fragile X-associated tremor/ataxia syndrome (FXTAS) patient. In some embodiments, the cell may be derived from a myotonic dystrophy type 1 (DM type 1) patient. In some embodiments, the cell may be derived from a myotonic dystrophy type 2 (DM type 2) patient. In some embodiments, the cell may be derived from a Friedreich's ataxia patient cell line. In some embodiments, the cell may be derived from a Fragile X syndrome (FXS) patient cell line. In some embodiments, the cell may be derived from a Fragile X-associated tremor/ataxia syndrome (FXTAS) patient cell line. In some embodiments, the cell may be derived from a myotonic dystrophy type 1 (DM type 1) patient cell line. In some embodiments, the cell may be derived from a myotonic dystrophy type 2 (DM type 2) patient cell line. In some embodiments, the Friedreich's ataxia patient cell line is a GM15850 cell line. In some embodiments, the cell may be a dorsal root ganglia neuron, cardiomyocyte, pancreatic beta cell, and/or B-lymphocyte.

In some embodiments, the cell comprises a gene associated with a genetic condition comprising at least about 50 repeats of an oligonucleotide sequence having 3 to 10 nucleotides. In some embodiments, the cell comprises a gene associated with a genetic condition comprising at least about 70 repeats of the oligonucleotide sequence. In some embodiments, the cell comprises a gene associated with a genetic condition comprising at least about 100 repeats of the oligonucleotide sequence. In some embodiments, the cell comprises a gene associated with a genetic condition comprising at least about 200 repeats of the oligonucleotide sequence.

In some embodiments, the cell comprises a gene associated with a genetic condition comprising a plurality of repeats of a GAA oligonucleotide sequence including at least about 50 GAA repeats. In some embodiments, the cell comprises a gene associated with a genetic condition comprising a plurality of repeats of a GAA oligonucleotide sequence including at least about 70 GAA repeats. In some embodiments, the cell comprises a gene associated with a genetic condition comprising a plurality of repeats of a GAA oligonucleotide sequence including at least about 100 GAA repeats. In some embodiments, the cell comprises a frataxin (FXN) gene including at least about 50 GAA repeats. In some embodiments, the cell comprises a frataxin (FXN) gene including at least about 70 GAA repeats. In some embodiments, the cell comprises an FXN gene including at least about 100 CGG repeats. In some embodiments, the cell comprises an FMR1 gene including at least about 50 CGG repeats. In some embodiments, the cell comprises an FMR1 gene including at least about 70 CGG repeats. In some embodiments, the cell comprises an FMR1 gene including at least about 100 CGG repeats. In some embodiments, the cell comprises an FMR1 gene including at least about 200 CGG repeats. In some embodiments, the cell comprises a DMPK gene including at least about 50 CGC repeats. In some embodiments, the cell comprises a DMPK gene including at least about 70 CGC repeats. In some embodiments, the cell comprises a DMPK gene including at least about 100 CGC repeats. In some embodiments, the cell comprises a CNBP (ZNF9 or zinc finger 9) gene including at least about 75 CCTG repeats. In some embodiments, the cell comprises a CNBP (ZNF9 or zinc finger 9) gene including at least about 100 CCTG repeats. In some embodiments, the cell comprises a CNBP (ZNF9 or zinc finger 9) gene including at least about 200 CCTG repeats.

In some embodiments, the mRNA levels produced from a gene comprising at least about 50 repeats of an oligonucleotide sequence are increased within about 6 hours after contacting the cell with any one or more of the agents shown in Section IV. In some embodiments, the mRNA levels produced from a gene comprising at least about 50 repeats of the oligonucleotide sequence are increased within about 24 hours after contacting the cell with any one or more of the agents shown in Section IV. In some embodiments, the mRNA levels produced from a gene comprising at least about 50 repeats of the oligonucleotide sequence are increased within about 2 days after contacting the cell with any one or more of the agents shown in Section IV. In some embodiments, the mRNA levels produced from a gene comprising at least about 50 repeats of the oligonucleotide sequence are increased within about 3 days after contacting the cell with any one or more of the agents shown in Section IV. In some embodiments, the frataxin mRNA levels are increased within about 6 hours after contacting the cell with any one or more of the agents shown in Section IV. In some embodiments, the frataxin mRNA levels are increased within about 24 hours after contacting the cell with any one or more of the agents shown in Section IV. In some embodiments, the frataxin mRNA levels are increased within about 2 days after contacting the cell with any one or more of the agents shown in Section IV. In some embodiments, the frataxin mRNA levels are increased within about 3 days after contacting the cell with any one or more of the agents shown in Section IV. In some embodiments, the FMR1 mRNA levels are increased within about 6 hours after contacting the cell with any one or more of the agents shown in Section IV. In some embodiments, the FMR1 mRNA levels are increased within about 24 hours after contacting the cell with any one or more of the agents shown in Section IV. In some embodiments, the FMR1 mRNA levels are increased within about 2 days after contacting the cell with any one or more of the agents shown in Section IV. In some embodiments, the FMR1 mRNA levels are increased within about 3 days after contacting the cell with any one or more of the agents shown in Section IV. In some embodiments, the DMPK mRNA levels are increased within about 6 hours after contacting the cell with any one or more of the agents shown in Section IV. In some embodiments, the DMPK mRNA levels are increased within about 24 hours after contacting the cell with any one or more of the agents shown in Section IV. In some embodiments, the DMPK mRNA levels are increased within about 2 days after contacting the cell with any one or more of the agents shown in Section IV. In some embodiments, the DMPK mRNA levels are increased within about 3 days after contacting the cell with any one or more of the agents shown in Section IV. In some embodiments, the CNBP (ZNF9 or zinc finger 9) mRNA levels are increased within about 6 hours after contacting the cell with any one or more of the agents shown in Section IV. In some embodiments, the CNBP (ZNF9 or zinc finger 9) mRNA levels are increased within about 24 hours after contacting the cell with any one or more of the agents shown in Section IV. In some embodiments, the CNBP (ZNF9 or zinc finger 9) mRNA levels are increased within about 2 days after contacting the cell with any one or more of the agents shown in Section IV. In some embodiments, the CNBP (ZNF9 or zinc finger 9) mRNA levels are increased within about 3 days after contacting the cell with any one or more of the agents shown in Section IV.

In one aspect, the present disclosure provides a method for treating a genetic condition associated with a gene comprising at least about 50 repeats of an oligonucleotide sequence having 3 to 10 nucleotides in a subject in need thereof, comprising administering any one or more of the agents shown in Section IV. In one aspect, the present disclosure provides a method for treating a genetic condition associated with a gene comprising a plurality of repeats of a GAA, CGG, CTG, or CCTG oligonucleotide sequence in a subject in need thereof, comprising administering any one or more of the agents shown in Section IV. In some embodiments, mRNA transcript levels produced from the gene including the multiple repeats may be increased relative to those prior to treatment by at least about 2.5-fold, at least about 3-fold, at least about 3.5-fold, at least about 4-fold, or at least about 6-fold. In one aspect, the present disclosure provides a method for treating Friedreich's ataxia (FRDA) in a subject in need thereof, comprising administering any one or more of the agents shown in Section IV. In some embodiments, the present disclosure provides a method for increasing frataxin mRNA levels in the subject. In some embodiments, frataxin mRNA levels of the subject are increased relative to those in the subject prior to treatment. In some embodiments, the frataxin mRNA levels are increased by at least about 2.5-fold. In some embodiments, the frataxin mRNA levels are increased by at least about 4-fold. In some embodiments, the frataxin mRNA levels are increased by at least about 8-fold. In some embodiments, frataxin protein levels of the subject are increased relative to those in the subject prior to treatment. In one aspect, the present disclosure provides a method for treating Fragile X syndrome (FXS) in a subject in need thereof, comprising administering any one or more of the agents shown in Section IV. In some embodiments, the present disclosure provides a method for increasing FMR1 mRNA levels in the subject. In some embodiments, FMR1 mRNA levels of the subject are increased relative to those in the subject prior to treatment. In some embodiments, the FMR1 mRNA levels are increased by at least about 2.5-fold. In some embodiments, the FMR1 mRNA levels are increased by at least about 4-fold. In some embodiments, the FMR1 mRNA levels are increased by at least about 8-fold. In some embodiments, FMRP protein levels of the subject are increased relative to those in the subject prior to treatment. In one aspect, the present disclosure provides a method for treating Fragile X-associated tremor/ataxia syndrome (FX-TAS) in a subject in need thereof, comprising administering any one or more of the agents shown in Section IV. In some embodiments, the present disclosure provides a method for increasing FMR1 mRNA levels in the subject. In some embodiments, FMR1 mRNA levels of the subject are increased relative to those in the subject prior to treatment. In some embodiments, the FMR1 mRNA levels are increased by at least about 2.5-fold. In some embodiments, the FMR1 mRNA levels are increased by at least about 4-fold. In some embodiments, the FMR1 mRNA levels are increased by at least about 8-fold. In some embodiments, FMRP protein levels of the subject are increased relative to those in the subject prior to treatment. In one aspect, the present disclosure provides a method for treating Myotonic dystrophy type 1 (DM type 1) in a subject in need thereof, comprising administering any one or more of the agents shown in Section IV. In some embodiments, the present disclosure provides a method for increasing DMPK mRNA levels in the subject. In some embodiments, DMPK mRNA levels of the subject are increased relative to those in the subject prior to treatment. In some embodiments, the DMPK mRNA levels are increased by at least about 2.5-fold. In some embodiments, the DMPK mRNA levels are increased by at least about 4-fold. In some embodiments, the DMPK mRNA levels are increased by at least about 8-fold. In some embodiments, DMPK protein levels of the subject are increased relative to those in the subject prior to treatment. In one aspect, the present disclosure provides a method for treating Myotonic dystrophy type 2 (DM type 2) in a subject in need thereof, comprising administering any one or more of the agents shown in Section IV. In some embodiments, the present disclosure provides a method for increasing CNBP mRNA levels in the subject. In some embodiments, CNBP mRNA levels of the subject are increased relative to those in the subject prior to treatment. In some embodiments, the CNBP mRNA levels are increased by at least about 2.5-fold. In some embodiments, the CNBP mRNA levels are increased by at least about 4-fold. In some embodiments, the CNBP mRNA levels are increased by at least about 8-fold. In some embodiments, CNBP protein levels of the subject are increased relative to those in the subject prior to treatment.

In one aspect, the present disclosure provides a method for treating a genetic condition associated with a gene comprising at least about 50 repeats of an oligonucleotide sequence having 3 to 10 nucleotides in a subject in need thereof, comprising administering a therapeutically effective amount of one or more agents having a formula A-L-B wherein -L- is a linker; A- is a Brd4 binding moiety; and —B is a polyamide that specifically binds to one or more repeats of the oligonucleotide sequence having 3 to 10 nucleotides. In some embodiments, the agent specifically binds to one more GAA repeats of an oligonucleotide sequence to treat Friedreich's ataxia (FRDA). In some embodiments, the agent specifically binds to one or more CGG repeats of an oligonucleotide sequence to treat Fragile X syndrome (FXS). In some embodiments, the agent specifically binds to one or more CGG repeats of an oligonucleotide sequence to treat Fragile X-associated tremor/ataxia syndrome (FX-TAS). In some embodiments, the agent specifically binds to one or more CTG repeats of an oligonucleotide sequence to treat Myotonic dystrophy type 1 (DM type 1). In some embodiments, the agent specifically binds to one or more CCTG repeats of an oligonucleotide sequence to treat Myotonic dystrophy type 2 (DM type 2).

In some embodiments, the treatment comprises ameliorating one or more symptoms of a genetic condition associated with a gene comprising at least about 50 repeats of an oligonucleotide sequence having 3 to 10 nucleotides. In some embodiments, the treatment comprises ameliorating one or more symptoms of Friedreich's ataxia. In some embodiments the symptoms of Friedreich's ataxia comprise one or more of ataxia, gait ataxia, muscle weakness, loss of coordination, loss of balance, lack of reflexes in lower limbs, loss of tendon reflexes, loss of ability to feel vibrations in lower limbs, loss of sensation in the extremities, loss of upper body strength, weakness in the arms, spasticity, loss of tactile sensation, impairment of position sense, impaired perception of light touch, impaired perception of pain, impaired perception of temperature, vision impairment, color vision changes, involuntary eye movements, pes cavus, inversion of the feet, hearing impairment, dysarthria, dysphagia, impaired breathing, scoliosis, diabetes, glucose intolerance, carbohydrate intolerance, hypertrophic cardiomyopathy, arrhythmia, myocardial fibrosis, cardiac failure, elevated serum or plasma high sensitive troponin-T (hsTNT) (>14 ng/L), or reduced serum or plasma frataxin protein levels (≤19 ng/mL for pediatric and ≤21 ng/mL for adult patients). In some embodiments, the treatment comprises ameliorating one or more symptoms of Fragile X syndrome (FXS). In some embodiments the symptoms of Fragile X syndrome (FXS) comprise one or more of intellectual disability, altered physical features in males including long face, soft skin, macroorchidism, ear infections, flat feet, high arched palate, double-jointed fingers, and hyper-flexible joints. Behavioral features may include ADD, ADHD, autism and autistic behaviors, autism spectrum disorder (ASD), social anxiety, hand-biting and/or flapping, poor eye contact, sensory disorders, seizures, Premature Ovarian Insufficiency (FXPOI), and increased aggression. In some embodiments, the treatment comprises ameliorating one or more symptoms of Fragile X-associated tremor/ataxia syndrome (FXTAS). In some embodiments the symptoms of Fragile X-associated tremor/ataxia syndrome (FXTAS) comprise one or more of Parkinsonian tremor, ataxia, cognitive decline, mood disorders, abnormal MRI, and eosinophilic nuclear inclusions in neurons and glial cells that contain ubiquitin and various proteins involved in proteasome degradation. In some embodiments, the treatment comprises ameliorating one or more symptoms of myotonic dystrophy type 1 (DM type 1). In some embodiments, the symptoms of myotonic dystrophy type 1 (DM type 1) comprise one or more of myotonia (hyperexcitability of skeletal muscle or sustained muscle contraction), muscle wasting of skeletal, cardiac and smooth muscle, insulin resistance, defects in cardiac conduction, cataracts, cognitive dysfunction, central nervous system involvement, and mental retardation. In some embodiments, the treatment comprises ameliorating one or more symptoms of myotonic dystrophy type 2 (DM type 2). In some embodiments, the symptoms of myotonic dystrophy type 2 (DM type 2) comprise one or more of myotonia (hyperexcitability of skeletal muscle or sustained muscle contraction), muscle wasting of skeletal, cardiac and smooth muscle, insulin resistance, defects in cardiac conduction, cataracts, cognitive dysfunction, and central nervous system involvement.

In some embodiments, the subject is human.

In some embodiments, the agent is administered orally, topically, systemically, intravenously, subcutaneously, transdermally, iontophoretically, intranasally, intraperitoneally, or intramuscularly.

In some embodiments, the present disclosure provides a method for treating Friedreich's ataxia (FRDA) in a subject in need thereof, comprising administering to the subject a therapeutically effective amount of a pharmaceutical composition comprising an agent(s) of the type described in Section IV and a pharmaceutically acceptable carrier.

In some embodiments, the present disclosure provides a method for treating Fragile X syndrome (FXS) in a subject in need thereof, comprising administering to the subject a therapeutically effective amount of a pharmaceutical composition comprising an agent(s) of the type described in Section IV and a pharmaceutically acceptable carrier.

In some embodiments, the present disclosure provides a method for treating Fragile X-associated tremor/ataxia syndrome (FXTAS) in a subject in need thereof, comprising administering to the subject a therapeutically effective amount of a pharmaceutical composition comprising an agent(s) of the type described in Section IV and a pharmaceutically acceptable carrier.

In some embodiments, the present disclosure provides a method for treating myotonic dystrophy type 1 (DM type 1) in a subject in need thereof, comprising administering to the subject a therapeutically effective amount of a pharmaceutical composition comprising an agent(s) of the type described in Section IV and a pharmaceutically acceptable carrier.

In some embodiments, the present disclosure provides a method for treating myotonic dystrophy type 2 (DM type 2) in a subject in need thereof, comprising administering to the subject a therapeutically effective amount of a pharmaceutical composition comprising an agent(s) of the type described in Section IV and a pharmaceutically acceptable carrier.

INCORPORATION BY REFERENCE

All publications, patents, and patent applications mentioned in this specification are herein incorporated by reference to the same extent as if each individual publication, patent, and patent application was specifically and individually indicated to be incorporated by reference.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A shows relative FXN mRNA levels produced in the GM15850 Friedreich's ataxia patient derived cell line following incubation for 24 hours with a control solution (0.1% DMSO), Control polyamide 3 ("3"), JQ1-(S), a mixture of Control polyamide 3 and JQ1-(S), Control conjugate 2 ("2"), and varying concentrations of Agent 4 ("4"). FIG. 1B shows relative FXN mRNA levels produced in a cell line that was derived from a clinically unaffected individual having two FXN alleles in the normal range of GAA trinucleotide repeats (GM15851) following incubation for 24 hours with a control solution (0.1% DMSO), Control polyamide 3 ("3"), JQ1-(S), a mixture of Control polyamide 3 and JQ1-(S), Control conjugate 2 ("2"), and varying concentrations of Agent 4 ("4"). FIG. 1C shows a side-by-side comparison of the data illustrated by FIGS. 1B and 1A.

FIG. 4 is a chart showing relative RNA concentrations of GM15850 cells harvested after 24 hours of treatment with the described compounds.

DETAILED DESCRIPTION

Figure 1A:
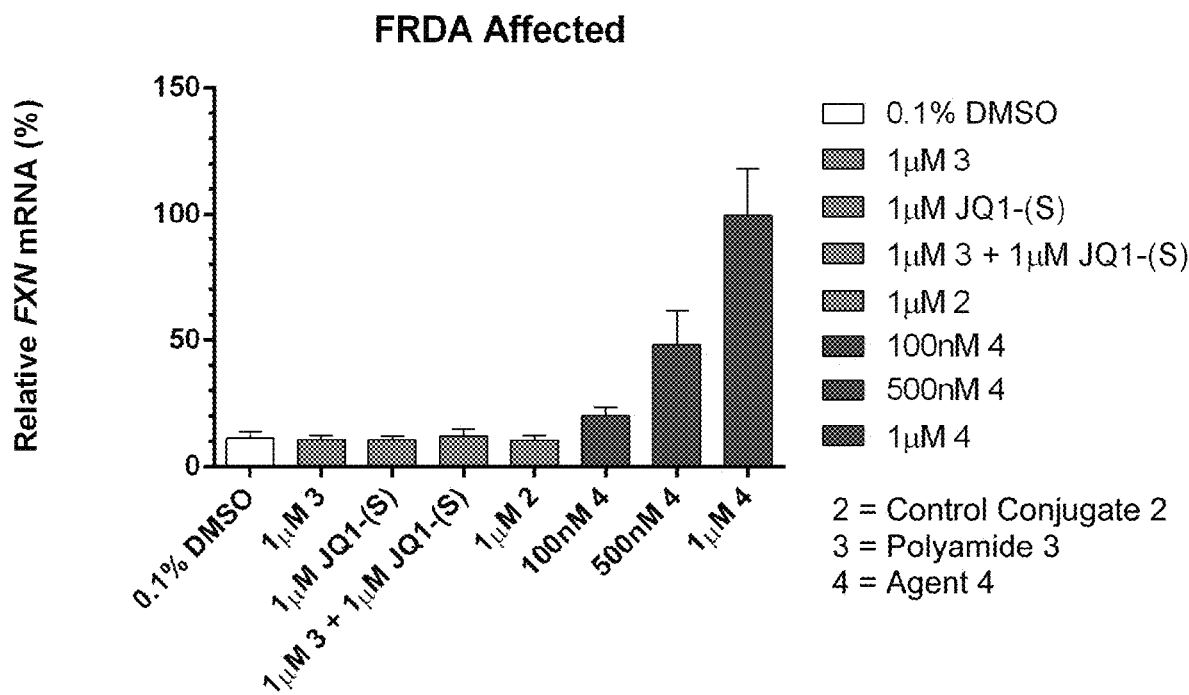
FIGS. 1A-1C show bar graphs illustrating the use of the agent of the present technology to increase frataxin levels in FRDA patient cells.

The present disclosure relates to compositions and methods for modulating the expression of genes, which include a target oligonucleotide sequence, such as repeats of an oligonucleotide sequence having 3 to 10 nucleotides, e.g., an oligonucleotide sequence containing multiple repeats of a GAA, CGG, CTG, or CCTG sequence. Certain embodiments of the methods are directed to modulating frataxin (FXN) gene expression, and for treating Friedreich's ataxia (FRDA). Some embodiments of the methods are directed to modulating fragile X Mental Retardation 1 (FMR1) gene expression, and for treating FXS. Some embodiments of the methods are directed to modulating fragile X Mental Retardation 1 (FMR1) gene expression, and for treating FXTAS. Some embodiments of the methods are directed to modulating dystrophia myotonic protein kinase (DMPK) gene expression, and for treating DM type 1. Some embodiments of the methods are directed to modulating CNBP (ZNF9 or zinc finger 9) gene expression, and for treating DM type 2.

Disclosed herein are agents having a formula A-L-B, wherein -L- is a linker; A- is a Brd4 binding moiety; and —B is a nucleic acid binding moiety, such as a polyamide that specifically binds to one or more repeats of an oligonucleotide sequence containing 3 to 10 nucleotides. Also disclosed herein are agents having a formula A-L-B, wherein -L- is a linker; A- is a Brd4 binding moiety; and —B is a polyamide that specifically binds to one or more repeats of a GAA oligonucleotide sequence. Also disclosed herein are agents having a formula A-L-B, wherein -L- is a linker; A- is a Brd4 binding moiety; and —B is a nucleic acid binding moiety, such as a polyamide that specifically binds to one or more repeats of a CGG oligonucleotide sequence. Also disclosed herein are agents having a formula A-L-B, wherein -L- is a linker; A- is a Brd4 binding moiety; and —B is a polyamide that specifically binds to one or more repeats of a CTG oligonucleotide sequence. Also disclosed herein are agents having a formula A-L-B, wherein -L- is a linker; A- is a Brd4 binding moiety; and —B is a polyamide that specifically binds to one or more repeats of a CCTG oligonucleotide sequence.

Also disclosed herein are methods for modulating mRNA levels produced from a gene in a cell comprising contacting the cell with an effective amount of one or more of the agents, wherein the gene comprises at least about 50 repeats of the oligonucleotide sequence. Also disclosed herein are methods for modulating protein levels in a cell, comprising contacting the cell with an effective amount of one or more of the agents, wherein the protein is encoded by a gene, which comprises at least about 50 repeats of the oligonucleotide sequence. Also disclosed herein are methods of treating a subject suffering from a genetic condition associated with a gene comprising a plurality of repeats of a GAA oligonucleotide sequence, comprising administering to the subject a therapeutically effective amount of one or more of the agents. Also disclosed herein are methods of treating Fragile X syndrome (FXS) in a subject in need thereof, comprising administering to the subject a therapeutically effective amount of one or more of the agents. Also disclosed herein are methods of treating Fragile X-associated tremor/ataxia syndrome (FXTAS) in a subject in need thereof, comprising administering to the subject a therapeutically effective amount of one or more of the agents. Also disclosed herein are methods of treating Myotonic dystrophy type 1 (DM type 1) in a subject in need thereof, comprising administering to the subject a therapeutically effective amount of one or more of the agents. Also disclosed herein are methods of treating Myotonic dystrophy type 2 (DM type 2) in a subject in need thereof, comprising administering to the subject a therapeutically effective amount of one or more of the agents.

I. Friedreich's Ataxia

Friedreich's ataxia (FA or FRDA) is an autosomal recessive neurodegenerative disorder caused by mutations in the FXN gene, which encodes the protein frataxin. Human frataxin is synthesized as a 210-amino acid precursor that is localized to the mitochondrion where the protein is subsequently cleaved to a mature 14 kDa protein (amino acid residues 81-210). Most FRDA patients (approximately 98%) carry a homozygous mutation characterized by an expansion of a GAA trinucleotide repeat in the first intron of the frataxin (FXN) gene, and this hyperexpansion causes FRDA. Pathological GAA expansions can range from about 66 to more than 1,000 trinucleotide repeats, whereas frataxin alleles that are not associated with FRDA comprise from about 6 to about 34 repeats. Hyperexpansion of the GAA repeats results in transcriptional repression and insufficient expression of frataxin (FXN), a highly-conserved, iron-binding mitochondrial protein. Transcription is a multistep, highly-regulated process that is divided into three stages: initiation, elongation, and termination. Recent evidence suggests that transcriptional elongation defects underlie a number of diseases caused by unstable nucleotide repeats. Without wishing to be bound by any particular theory, recent evidence suggests that transcriptional elongation is the primary step affected by the pathological GAA expansion, with the expanded GAA repeats leading to the premature termination or pausing of FXN transcription and, ultimately, decreased cellular frataxin protein levels. Accordingly, without wishing to be bound by any particular theory, FRDA may be characterized as a transcriptional pausing-based genetic disease caused by a defect in transcriptional elongation resulting in transcriptional repression and reduced expression of a gene (e.g., FXN). RNA polymerase-II initiates transcription of the repressed gene underlying the disease, but fails to elongate through the entire open reading frame of the gene to produce full-length pre-mRNA. Splicing is typically unaffected, thereby allowing for the production of normal full-length protein, albeit at reduced levels.

Friedreich's ataxia is the most common hereditary ataxia and causes progressive damage to the nervous system, particularly sensory neurons. Although frataxin is ubiquitously expressed, certain cells (e.g., dorsal root ganglia neurons, cardiomyocytes, and pancreatic beta cells) are particularly sensitive to frataxin depletion, and the resulting degenerative loss of these cells accounts for the clinical manifestations of FRDA. FRDA patients develop neurodegeneration of the large sensory neurons and spinocerebellar tracts, as well as cardiomyopathy and diabetes mellitus. Clinical symptoms of FRDA include ataxia, gait ataxia, muscle weakness, loss of coordination, loss of balance, lack of reflexes in lower limbs, loss of tendon reflexes, loss of ability to feel vibrations in lower limbs, loss of sensation in the extremities, loss of upper body strength, weakness in the arms, spasticity, loss of tactile sensation, impairment of position sense, impaired perception of light touch, impaired perception of pain, impaired perception of temperature, vision impairment, color vision changes, involuntary eye movements, pes cavus, inversion of the feet, hearing impairment, dysarthria, dysphagia, impaired breathing, scoliosis, diabetes, glucose intolerance, carbohydrate intolerance, hypertrophic cardiomyopathy, arrhythmia, myocardial fibrosis, cardiac failure, elevated serum or plasma high sensitive troponin-T (hsTNT) (>14 ng/L), and reduced serum or plasma frataxin protein levels (≤19 ng/mL for pediatric and ≤21 ng/mL for adult patients).

There is an inverse correlation between GAA repeat length and FXN protein levels, and there is a tight correlation between frataxin protein levels and the severity of disease. That is, lower frataxin protein levels correlate with greater GAA repeat length and disease severity. FRDA patients exhibiting clinical symptoms have frataxin protein levels that are between 5% and 35% those of healthy individuals. Asymptomatic heterozygous carriers have frataxin protein levels that are about 50% those of healthy individuals. Asymptomatic heterozygous carriers have frataxin protein levels that are about 40-45% those of healthy individuals. Most FRDA patients (approximately 98%) carry a homozygous mutation in the first intron of the frataxin (FXN) gene comprising an expansion of a GAA trinucleotide repeat. Pathological GAA expansions can range from about 66 to more than 1,000 trinucleotide repeats, whereas frataxin alleles that are not associated with disease comprise from about 6 to about 34 repeats. Very rare cases of FRDA (about 4%) are characterized by an expansion of a GAA trinucleotide repeat present in one allele and a deleterious point mutation in the other allele. It is generally understood that longer GAA trinucleotide repeats are associated with greater deficiency of frataxin and earlier onset and increased severity of disease. Partially restoring frataxin in affected cells may slow or prevent disease progression.

Diagnosis

FRDA is diagnosed by assessing clinical criteria and/or performing genetic testing (Wood, N. W., Arch. Dis. Child., 78:204-207 (1998)). The patient's medical history is evaluated and a physical examination performed. Key to diagnosing FRDA is the recognition of hallmark symptoms, including balance difficulty, loss of joint sensation, absence of reflexes, and signs of neurological problems. In addition, genetic testing can provide a conclusive diagnosis of FRDA.

Clinical Criteria.

Strict clinical criteria have been developed that are widely used in the diagnosis of FRDA (Harding, A. E., Brain, 104:589-620 (1981)). Diagnostic criteria include an age of onset before 25 years of age, as well as presence of the following symptoms: progressive ataxia of gait and limbs, absence of knee and ankle jerks, axonal picture on neurophysiology, and dysarthria (if after five years from onset). In over 66% of individuals with FRDA, the following symptoms are present: scoliosis, pyramidal weakness in lower limbs, absence of reflexes in arms, large fibre sensory loss on examination, and abnormal ECG. In less than 50% of individuals having FRDA, the following symptoms are present: nystagmus, optic atrophy, deafness, distal amyotrophy, pes cavus, and diabetes. However, some cases of FRDA present atypically. For example, onset of FRDA may occur over the age of 20 years in some patients. Moreover, some patients retain tendon reflexes.

Core features of pyramidal tract involvement include the association of extensor plantar responses, absence of ankle reflexes, and a progressive course of disease. Pyramidal weakness in lower limbs can lead to paralysis. Skeletal abnormalities are common in FRDA. For example, scoliosis is present in approximately 85% of FRDA patients. Foot abnormalities may be present, including pes cavus and, less frequently, pes planus and equinovarus. Amyotrophy of the lower legs may occur. Optic atrophy is present in about 25% of FRDA cases, while major visual impairment occurs in less than 5% of cases. Deafness is present in less than 10% of FRDA cases. Blood sugar analysis is also performed, as diabetes is seen in approximately 10% of FRDA patients. About 20% of FRDA patients develop carbohydrate intolerance.

A prominent non-neurological feature of FRDA is cardiomyopathy, which may initially present as the sole symptom of disease. An electrocardiogram (ECG) may be performed to assess electrical and muscular functions of the heart. Approximately 65% of FRDA patients present with an abnormal ECG, having widespread T wave inversion in the inferolateral chest leads. The most frequent echocardiographic abnormality in FRDA patients is concentric ventricular hypertrophy. Heart failure typically occurs late in disease progression, often accounting for premature death in FRDA patients.

Within a few years after onset of FRDA, the patient presents with dysarthria and pyramidal weakness, and subsequent nystagmus, which is characterized by involuntary repetitive and jerky eye movements. Within about 10-15 years after onset of disease, the patient becomes wheelchair bound.

Additional tests typically employed to assess FRDA patients include electromyogram (EMG) to measure electrical activity of muscle cells, nerve conduction studies to measure nerve impulse transmission speed, echocardiogram to record the position and motion of heart muscle, and blood tests to determine if the patient has vitamin E deficiency. Magnetic resonance imaging (MRI) or computed tomography (CT) scans provide brain and spinal cord images that can be useful to rule out other neurological conditions.

Genetic Testing.

FRDA is a neurological disorder caused by mutations in the frataxin (FXN) gene, having a cytogenetic location of 9q21.11. DNA-based testing is one method that is used to diagnose FRDA. Homozygosity for a GAA repeat expansion in intron 1 of FXN indicates FRDA. Rarely, patients will present as heterozygous for an allele having a GAA repeat expansion and an allele having a point mutation in FXN.

FRDA Biomarkers

Frataxin Protein Levels.

Frataxin protein levels may be measured to diagnose and monitor treatment efficacy in FRDA patients. This also permits multiplexing with other disease analytes and population screening. In this approach, frataxin protein levels may be measured by a high-throughput immunoassay. Tests can be performed employing whole blood samples or dried blood spots to measure frataxin protein. For whole blood samples, frataxin levels that are ≤19 ng/mL for pediatric individuals (less than 18 years of age) and ≤21 ng/mL for adults (18 years of age or older) are consistent with a diagnosis of FRDA. Frataxin levels that are ≥19 ng/mL for pediatric individuals and ≥21 ng/mL for adults measured using whole blood samples are not consistent with FRDA. For dried blood spot samples, frataxin levels that are ≤15 ng/mL for pediatric individuals (less than 18 years of age) and ≤21 ng/mL for adults are not consistent with FRDA. Frataxin levels that are ≥15 ng/mL for pediatric individuals and ≥21 ng/mL for adults measured using dried blood samples are not consistent with FRDA.

High Sensitive Troponin-T.

High sensitive Troponin-T (hsTNT) may be useful as a blood biomarker to indicate cumulative myocyte damage leading to fibrosis in FRDA patients (Weidemann, et al., *Intl. J. Cardiol.*, 194:50-57 (2015)). Troponin T is a myofibrillar protein that is present in striated musculature. There are two types of myofilaments, a thick myosin-containing filament and a thin filament consisting of actin, tropomyosin, and troponin. Troponin is a complex of 3 protein subunits: troponin T, troponin I, and troponin C. Troponin T functions to bind the troponin complex to tropomyosin.

In the cytosol, troponin T is present in soluble and protein-bound forms. The soluble or unbound pool of troponin T is released in early stages of myocardial damage. Bound troponin T is released from myofilaments at a later stage of irreversible myocardial damage, corresponding with degradation of myofibrils. The most common cause of cardiac injury is myocardial ischemia (i.e., acute myocardial infarction). Troponin T levels increase approximately 2 to 4 hours after the onset of myocardial necrosis, and can remain elevated for up to 14 days.

Myocardial fibrosis and disease progression appear to correlate strongly with hsTNT levels in FRDA patients. The cutoff point for the hsTNT levels is 14 ng/L (0.014 ng/mL) (ELECSYS® Troponin T hs (TnT-hs), which is available from Roche). Elevated serum or plasma hsTNT levels >14 ng/L (0.014 ng/mL) are seen in FRDA patients with hypertrophic cardiomyopathy (CM). Elevated hsTNT levels may indicate cumulative myocyte damage leading to fibrosis in FRDA.

II. Other Transcriptional Pausing-Based Genetic Diseases

It is thought that pausing of RNA polymerase-II at genes having expanded oligonucleotide repeats plays a role in disease pathogenesis at the molecular level, thereby inhibiting transcriptional elongation. Genetic diseases whose pathogenesis is thought to be mediated or caused by such transcriptional-based pausing include FRDA, Fragile X syndrome (FXS), Fragile X-associated tremor/ataxia syndrome, myotonic dystrophy type 1 (DM type 1), and myotonic dystrophy type 2 (DM type 2). Methods of identifying transcriptional pausing-based diseases would include the following: 1) identify a disease in which expanded oligonucleotide repeats do not affect the primary structure (amino acid sequence) of the corresponding protein, 2) determine whether aberrant splicing is present (e.g., by Northern blot), 3) if no aberrant splicing is present, determine whether transcription initiation occurs (e.g., using a chromatin immunoprecipitation assay or by measuring the production of nascent RNA).

Fragile X Syndrome (FXS)

Fragile X syndrome (FXS) is a genetic syndrome that causes a range of developmental defects, including learning disabilities, cognitive impairment, and various behavioral and physical features. It is sometimes referred to as Martin-Bell syndrome, or Escalante's syndrome. Typically, males are affected more severely than females. It is also associated with autism spectrum disorder (ASD). FXS is the most common cause of inherited intellectual disability, occurring in approximately 1 in 3700 white males, 1 in 2500 black males, and 1 in 7000 heterozygous females (Hersch, et al., *Pediatrics*, 127:994-1006 (2011)). In addition to intellectual disability, physical features in males include long face, soft skin, macroorchidism, ear infections, flat feet, high arched palate, double-jointed fingers, and hyper-flexible joints. Behavioral features may include ADD, ADHD, autism and autistic behaviors, social anxiety, hand-biting and/or flapping, poor eye contact, sensory disorders and increased aggression. FXS individuals are also at a higher risk for developing seizures. FXS female patients may display these symptoms, although typically presenting as a milder form. Women who carry the premutation allele, discussed below, are at an approximately 25% risk of having Fragile X-associated Premature Ovarian Insufficiency (FXPOI).

FXS was named for a "fragile" site on the X chromosome where nonstaining gaps in the metaphase chromosome are seen, near the end of the long arm of the X chromosome (Nelson, et al., *Neuron*, 77(5):825-843 (2013)). In particular, the site is located at band q27.3 on the long arm of the X chromosome (Xq27.3). The disease gene, Fragile X Mental Retardation 1 (FMR1) is located at the fragile site and contains a polymorphic trinucleotide cytosine-guanine-guanine (CGG) repeat located within the 5' untranslated region of exon 1. The CGG repeat is highly polymorphic in the general population. Four allelic classes encompass FMR1 alleles. First, normal alleles have 5 to 44 CGG repeats, with the most common normal allele having 29 or 30 CGG repeats. Second, full mutation alleles found in FXS patients typically have over 200 CGG repeats, with as many as several hundred repeats. Third, premutation alleles contain between 54 and 200 CGG repeats, and are meiotically unstable, particularly when maternally transmitted. Full mutation alleles are derived from permutation alleles. Fourth, intermediate alleles have between 45 and 54 repeats. However, unlike the premutation alleles, intermediate alleles do not directly transform into full mutation alleles.

Full mutation alleles cause FXS, resulting in the hypermethylation of FMR1, leading to gene-silencing and a decrease in fragile X mental retardation 1 protein (FMRP) levels. Full mutation alleles effectively correspond to FMR1 loss of function, and lack of FMRP results in FXS. Clinical severity of FXS typically correlates with the degree of FMR1 methylation and gene-silencing rather than the length or number of CGG repeats.

Human FMR1 has 17 exons with significant alternative splicing patterns, having multiple FMRP isoforms (67-80 Kd) with the most abundant at 69 Kd (isoform 7). FMRP is a predominantly cytoplasmic protein, with about 5% localized in the nucleus, and has been shown to selectively bind RNA, having KH domains and an RGG box. It is widely expressed, but is abundant in neurons and testes.

Fragile X-Associated Tremor/Ataxia Syndrome (FXTAS)

Fragile X-associated tremor/ataxia syndrome (FXTAS) is a progressive neurodegenerative condition. Males having FMR1 premutation alleles are at substantial risk of developing FXTAS (more than 50% showing symptoms by 70 years of age), while female carriers have a lower risk (about 20%). As discussed above, the permutation alleles of FMR1 contain between 54 and 200 CGG repeats. Symptoms of FXTAS are variable, and may include Parkinsonian tremor, ataxia, cognitive decline, mood disorders, and abnormal MRI. Autopsy may reveal the presence of eosinophilic nuclear inclusions in neurons and glial cells that contain ubiquitin and various proteins involved in proteasome degradation.

Myotonic Dystrophy Type 1 (DM Type 1) and Myotonic Dystrophy Type 2 (DM Type 2)

Myotonic dystrophy (DM) is a dominantly inherited genetic disorder that affects approximately 1 in 8500 individuals worldwide (Lee, et al., *Biochem. Soc. Trans.*, 371-11 (2009)). DM is a multisystemic disorder and represents the second most common form of muscular dystrophy. DM is characterized by the following features: myotonia (hyperexcitability of skeletal muscle or sustained muscle contraction), muscle wasting of skeletal, cardiac and smooth muscle, insulin resistance, defects in cardiac conduction, cataracts, cognitive dysfunction, central nervous system involvement, and, in the most severe congenital form, mental retardation. Two types of DM exist, myotonic dystrophy type 1 (DM type 1) and myotonic dystrophy type 2 (DM type 2). DM type 1 and DM type 2 patients show similar symptoms, except that a severe form of congenital DM type 1 exists not found in DM type 2 patients. Of the two types, DM type 1 is the more common in the United States.

DM type 1 is caused by a trinucleotide cytosine-thymine-guanine (CTG) nucleotide expansion within the DMPK (dystrophia myotonica protein kinase) 3'-untranslated region. Unaffected individuals have about 5-38 CTG trinucleotide repeats, and symptoms of DM type 1 may occur in individuals with as few as 50 CTG repeats. Premutation includes individuals having repeats of between about 38 and 49 repeats. Longer repeats correlate with greater disease severity and earlier age of onset of disease. Myotonic dystrophy type 2 (DM type 2) is caused by a tetra-(CCTG) nucleotide expansion within intron 1 of the cellular nucleic acid-binding protein (CNBP, zinc finger 9, or ZHF9) gene. The number of CCTG repeats in alleles having expanded repeats ranges from about 75 to more than 11,000, with a mean of approximately 5000 repeats (Dalton, et al., GENEREVIEWS®, Pagon R A, Adam M P, Ardinger H H, et al., editors, Seattle (Wash.): University of Washington, Seattle; 1993-2016 (last viewed on Mar. 24, 2016)).

III. Methods for the Modulation of Gene Expression

The present technology relates to methods and compositions for modulating gene expression. The expression of genes, such as FXN, FMR1, DMPK, and ZNF9, may be modulated using the methods and compositions of the present invention. In particular, the methods and compositions relate to the use of one or more agents to stimulate gene transcription. In one aspect, the methods and compositions of the present technology relate to agents having a formula A-L-B, wherein -L- is a linker; A- is a Brd4 binding moiety; and —B is a nucleic acid binding moiety, such as a polyamide, that specifically binds to one or more repeats of one or more repeats of an oligonucleotide sequence having 3 to 10 nucleotides, such as a GAA, CGG, CTG, or CCTG oligonucleotide sequence, or other target sequence and the use of one or more of these agents to stimulate gene transcription. In some embodiments, the nucleic acid binding moiety (—B) specifically binds to a target oligonucleotide sequence. In some embodiments, the nucleic acid binding moiety (—B) specifically binds to one or more repeats of a short oligonucleotide sequence-such as a GAA oligonucleotide sequence. In some embodiments, the nucleic acid binding moiety (—B) is a polyamide. In some embodiments, the nucleic acid binding moiety (—B) is a polyamide that specifically binds to one or more repeats of an oligonucleotide sequence containing 3 to 6 nucleotides, such as a GAA oligonucleotide sequence. In some embodiments, that nucleic acid binding moiety (—B) comprises an oligonucleotide sequence (e.g., containing about 15 to 30 nucleotides) that is complementary to a desired target oligonucleotide sequence. In some embodiments, the nucleic acid binding moiety (—B) may be a nucleic acid sequence capable of hybridizing to one or more repeats of a GAA oligonucleotide sequence or to one or more repeats of a TTC oligonucleotide sequence. In some embodiments, the nucleic acid binding moiety (—B) may be a deoxyribonucleic acid (DNA) sequence, a ribonucleic acid (RNA) sequence, or a peptide nucleic acid (PNA) sequence capable of hybridizing to one or more repeats of a GAA oligonucleotide sequence or to one or more repeats of a TTC oligonucleotide sequence. For example, the nucleic acid binding moiety (—B) may be a deoxyribonucleic acid (DNA) sequence comprising, consisting of, or consisting essentially of one or more repeats of a TTC sequence, including, but not limited to, TTCTTCTTC, TTCTTCTTCTTC (SEQ ID NO:2), TTCTTCTTCTTCTTC (SEQ ID NO:3), TTCTTCTTCTTCTTCTTC (SEQ ID NO:4), and TTCTTCTTCTTCTTCTTCTTC (SEQ ID NO:5). In another example, the nucleic acid binding moiety (—B) may be a deoxyribonucleic acid (DNA) sequence comprising, consisting of, or consisting essentially of one or more repeats of a GAA sequence, including, but not limited to, GAAGAAGAA, GAAGAAGAAGAA (SEQ ID NO:6), GAAGAAGAAGAAGAA (SEQ ID NO:7), GAAGAAGAAGAAGAAGAA (SEQ ID NO:8), and GAAGAAGAAGAAGAAGAAGAA (SEQ ID NO:9). In another example, the nucleic acid binding moiety (—B) may be a ribonucleic acid (RNA) sequence comprising, consisting of, or consisting essentially of one or more repeats of a CUU sequence, including, but not limited to, CUUCUUCUU, CUUCUUCUUCUU (SEQ ID NO:10), CUUCUUCUUCUUCUU (SEQ ID NO:11), CUUCUUCUUC- UUCUUCUU (SEQ ID NO:12), and CUUCUUCUUCUUCUUCUUCUU (SEQ ID NO:13).

In some embodiments, the nucleic acid binding moiety (—B) may be a deoxyribonucleic acid (DNA) sequence comprising, consisting of, or consisting essentially of 1 to 10, 1 to 15, 1 to 20, 1 to 25, 1 to 30, 1 to 35, 1 to 40, 1 to 45, 1 to 50, 1 to 55, 1 to 60, 1 to 65, 1 to 70, 1 to 75, 1 to 80, 1 to 85, 1 to 90, 1 to 95, 1 to 100, 1 to 150, 1 to 200, 1 to 250, 1 to 300, 1 to 350, 1 to 400, 1 to 450, 1 to 500, 1 to 550, 1 to 600, 1 to 650, 1 to 700, 1 to 750, 1 to 800, 1 to 850, 1 to 900, 1 to 950, or 1 to 1000 repeats of a TTC sequence. In some embodiments, the nucleic acid binding moiety (—B) may be a DNA sequence of 5 to 10 repeats of a TTC sequence (e.g., 15 to 30 base pairs in length). In some embodiments, the nucleic acid binding moiety (—B) may be a DNA sequence of 5 to 10 repeats of a TTC sequence (e.g., 15 to 30 nucleotide bases in length). In some embodiments, the nucleic acid binding moiety (—B) may be a DNA sequence of 5 to 6 repeats of a TTC sequence. In some embodiments, the nucleic acid binding moiety (—B) may be a DNA sequence of 5 to 7 repeats of a TTC sequence. In some embodiments, the nucleic acid binding moiety (—B) may be a DNA sequence of 5 to 8 repeats of a TTC sequence. In some embodiments, the nucleic acid binding moiety (—B) may be a DNA sequence of 5 to 9 repeats of a TTC sequence.

In some embodiments, the nucleic acid binding moiety (—B) may be a deoxyribonucleic acid (DNA) sequence comprising, consisting of, or consisting essentially of 1 to 10, 1 to 15, 1 to 20, 1 to 25, 1 to 30, 1 to 35, 1 to 40, 1 to 45, 1 to 50, 1 to 55, 1 to 60, 1 to 65, 1 to 70, 1 to 75, 1 to 80, 1 to 85, 1 to 90, 1 to 95, 1 to 100, 1 to 150, 1 to 200, 1 to 250, 1 to 300, 1 to 350, 1 to 400, 1 to 450, 1 to 500, 1 to 550, 1 to 600, 1 to 650, 1 to 700, 1 to 750, 1 to 800, 1 to 850, 1 to 900, 1 to 950, or 1 to 1000 repeats of a GAA sequence. In some embodiments, the nucleic acid binding moiety (—B) may be a DNA sequence of 5 to 10 repeats of a GAA sequence (e.g., 15 to 30 base pairs in length). In some embodiments, the nucleic acid binding moiety (—B) may be a DNA sequence of 5 to 6 repeats of a GAA sequence. In some embodiments, the nucleic acid binding moiety (—B) may be a DNA sequence of 5 to 7 repeats of a GAA sequence. In some embodiments, the nucleic acid binding moiety (—B) may be a DNA sequence of 5 to 8 repeats of a GAA sequence. In some embodiments, the nucleic acid binding moiety (—B) may be a DNA sequence of 5 to 9 repeats of a GAA sequence.

In some embodiments, the nucleic acid binding moiety (—B) may be a ribonucleic acid (RNA) sequence comprising, consisting of, or consisting essentially of 1 to 10, 1 to 15, 1 to 20, 1 to 25, 1 to 30, 1 to 35, 1 to 40, 1 to 45, 1 to 50, 1 to 55, 1 to 60, 1 to 65, 1 to 70, 1 to 75, 1 to 80, 1 to 85, 1 to 90, 1 to 95, 1 to 100, 1 to 150, 1 to 200, 1 to 250, 1 to 300, 1 to 350, 1 to 400, 1 to 450, 1 to 500, 1 to 550, 1 to 600, 1 to 650, 1 to 700, 1 to 750, 1 to 800, 1 to 850, 1 to 900, 1 to 950, or 1 to 1000 repeats of a CUU sequence. In some embodiments, the nucleic acid binding moiety (—B) may be an RNA sequence of 5 to 10 repeats of a CUU sequence (e.g., 15 to 30 nucleotide bases in length). In some embodiments, the nucleic acid binding moiety (—B) may be an RNA sequence of 5 to 6 repeats of a CUU sequence. In some embodiments, the nucleic acid binding moiety (—B) may be an RNA sequence of 5 to 7 repeats of a CUU sequence. In some embodiments, the nucleic acid binding moiety (—B) may be an RNA sequence of 5 to 8 repeats of a CUU sequence. In some embodiments, the nucleic acid binding moiety (—B) may be an RNA sequence of 5 to 9 repeats of a CUU sequence.

In some embodiments, the nucleic acid binding moiety (—B) comprises a repeat-targeted duplex RNA, such as an anti-GAA duplex RNA that specifically targets GAA repeats. In some embodiments, the nucleic acid binding moiety (—B) comprises single-stranded locked nucleic acids (LNAs), such as anti-GAA LNA oligomers that specifically target GAA repeats.

In some embodiments, the present technology relates to methods and compositions for preventing or treating a genetic condition in a subject in need thereof, such as Friedreich's ataxia (FR or FRDA), Fragile X syndrome (FXS), Fragile X-associated tremor/ataxia syndrome (FXTAS), myotonic dystrophy type 1 (DM type 1), or myotonic dystrophy type 2 (DM type 2). In some embodiments, the methods and compositions of the present technology increase the level of mRNA levels in a cell. In some embodiments, the mRNA is FXN, FMR1, DMPK, or CNBP. In some embodiments, the methods and compositions of the present technology increase protein levels in a cell. In some embodiments, the protein is FXN, FMR1, DMPK, or CNBP. In some embodiments, the methods and compositions of the present technology prevent one or more signs or symptoms of a genetic condition in a subject. In some embodiments, the genetic condition is Friedreich's ataxia (FR or FRDA), Fragile X syndrome (FXS), Fragile X-associated tremor/ataxia syndrome (FXTAS), myotonic dystrophy type 1 (DM type 1), or myotonic dystrophy type 2 (DM type 2). In some embodiments, the methods and compositions of the present technology reduce the likelihood that a subject with risk factors for a genetic condition will develop one or more signs or symptoms of a genetic condition, or will delay the onset of a genetic condition. In some embodiments, the genetic condition is Friedreich's ataxia (FR or FRDA), Fragile X syndrome (FXS), Fragile X-associated tremor/ataxia syndrome (FXTAS), myotonic dystrophy type 1 (DM type 1), or myotonic dystrophy type 2 (DM type 2).

Figure 12:
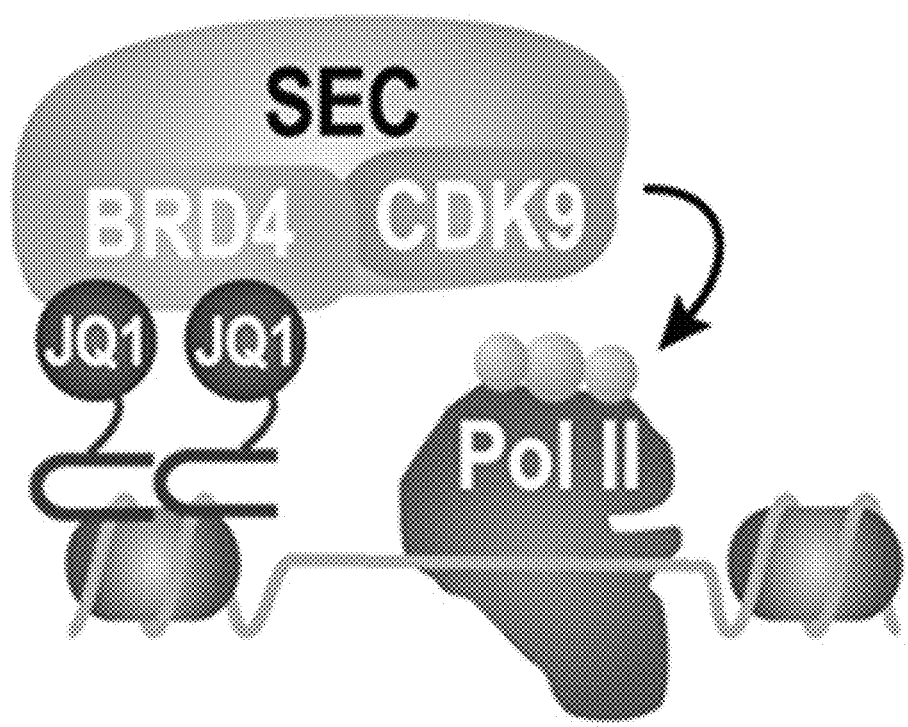
FIG. 12 shows Scheme 1, a model transcription elongation stimulator. Without wishing to be bound by any particular theory, the polyamide-JQ1 conjugate binds selectively to one or more repeats in an oligonucleotide sequence (e.g., one or more GAA trinucleotide repeats), and through the interaction of JQ1 with Brd4, recruits the super elongation complex (SEC) to stimulate and restart the paused RNA polymerase-II (Pol II) transcription complex, thereby resulting in transcription of frataxin (FXN) mRNA.

As described in more detail below, the agents disclosed herein combine a nucleic acid binding moiety, such as a DNA-binding polyamide subunit (—B) that specifically binds to one or more repeats of a GAA oligonucleotide sequence with a linker (-L-) and a Brd4 binding moiety (A-). In some embodiments, the Brd4 binding moiety is has a structure related to a bromodomain inhibitor (e.g., JQ1). Though not wishing to be bound by any particular theory, as depicted by the model transcription elongation stimulator in Scheme 1 (FIG. 12), it is believed that the polyamide-JQ1 conjugate binds selectively to one or more repeats in an oligonucleotide sequence (e.g., one or more GAA trinucleotide repeats), and through the interaction of JQ1 with Brd4, recruits the super elongation complex (SEC) to stimulate and restart the paused RNA polymerase-II (Pol II) transcription complex, thereby resulting in transcription of frataxin (FXN) mRNA.

Figure 13:
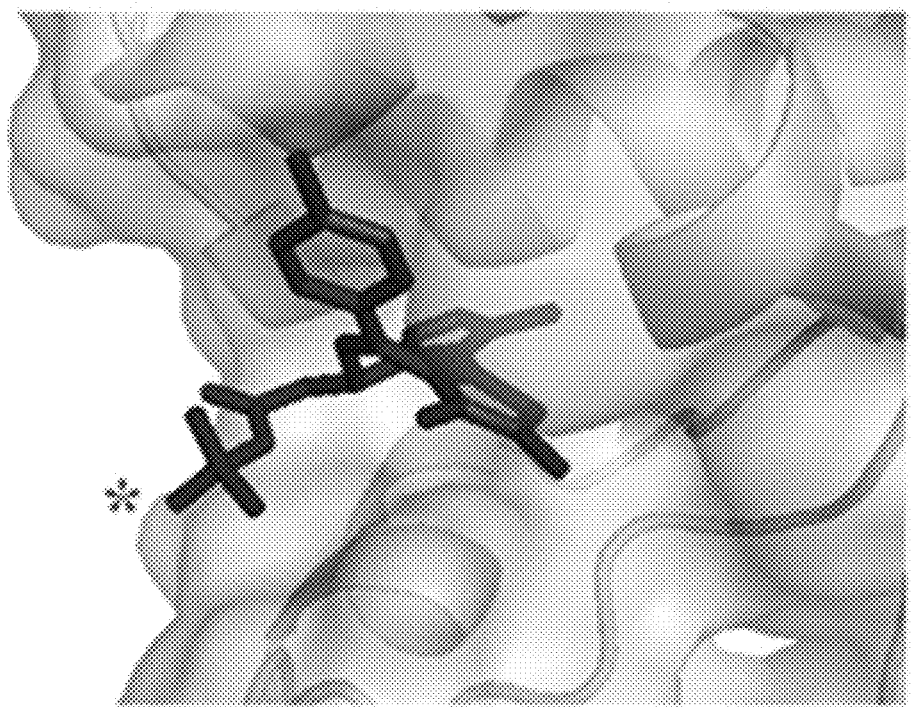
FIG. 13 shows Scheme 2 depicting a crystal structure showing (S)-JQ1 bound to Brd4.

JQ1 is one example of a selective small-molecule bromodomain inhibitor. Specifically, JQ1 is a thieno-triazolo-1,4-diazepine that displaces bromodomain and extra-terminal (BET) family members (e.g., Brd4) from chromatin by competitively binding to the acetyl-lysine recognition pocket. (Delmore, et al., *Cell*, 146(6):904-917 (2011)). Delmore, et al. have shown that Brd4 is strongly enriched at immunoglobulin heavy chain (IgH) enhancers in MM cells bearing IgH rearrangement at the MYC locus and that JQ1 depletes enhancer-bound Brd4 and inhibits MYC transcription in a dose- and time-dependent manner. In addition, JQ1 has been shown to bind and displace BRD4 from chromatin thereby inhibiting transcription of Brd4-dependent genes. (See Filippakopoulos, et al. *Nature* 468: 1067-1073). Accordingly, previous studies have established a role for JQ1 and related structures in binding Brd4 to inhibit transcription. Scheme 2 (FIG. 13) depicts a crystal structure showing (S)-JQ1 bound to Brd4 (Protein Data Bank accession 3MXF). The tert-butyl group, highlighted by an asterisk, projects out of the binding pocket of Brd4, indicating that chemical substitution at this position would likely be tolerated.

Figure 14:
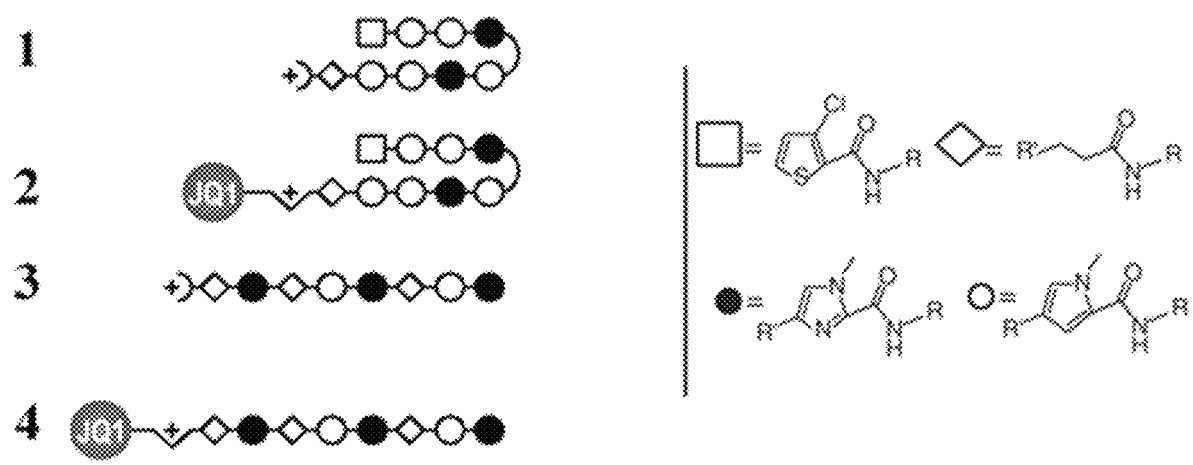
FIG. 14 shows Scheme 3 depicting examples of compounds (including controls) tested by the methods of the present technology to determine their ability to function as transcription elongation stimulators include Polyamide 1 ("1") Control Conjugate 2 ("2"), Polyamide 3 ("3") and Agent 4 ("4").

Examples of compounds (including controls) tested by the methods of the present technology to determine their ability to function as transcription elongation stimulators include Polyamide 1 ("1") Control Conjugate 2 ("2"), Polyamide 3 ("3") and Agent 4 ("4"), as depicted in Scheme 3 (FIG. 14).

Brd4 has been reported to play a role in mediating transcriptional elongation, functioning to recruit the positive transcription elongation factor (P-TEFb), which plays an essential role in the regulation of transcription by RNA polymerase-II (Pol II). In humans, there are multiple forms of P-TEFb, which contain the catalytic subunit, Cdk9, and together with several other cyclin subunits associate with Brd4 to form a complex of proteins called the super elongation complex (SEC). Without wishing to be bound by theory, it is believed that recruitment of this complex facilitates the transition of promoter-proximal paused Pol II into productive elongation.

Engineered polyamides have been shown to bind DNA with high affinity. For example, pyrrole-imidazole polyamides are cell-permeable small molecules that can be designed to bind a variety of DNA sequences. (Burnett et al. *PNAS* 103(31):11497-11502). Previous studies have reported that DNA sequence-specific polyamides that bind GAA trinucleotide repeats lead to an approximate 3-fold increase in transcription of frataxin in cell culture when provided at a concentration of 2 μM for 7 days (polyamide replenished on days 3 and 5). However, no significant changes in frataxin mRNA levels were observed with shorter incubation times. (Burnett et al.).

By contrast, the methods disclosed herein allow for the activation of FXN in a Friedreich's ataxia cell line with as little as a 100 nM concentration of the agents of the present technology after only 24 hours. For example, as shown in FIG. 1A, the agents of the present technology, which comprise JQ1, a general transcription inhibitor, potently activate FXN to produce a greater than 4-fold increase in mRNA levels when administered to FRDA cells at a concentration of 500 nM after only 24 hours. This approximate 4-fold increase returns mRNA levels to those typically present in asymptomatic heterozygotes. Also, as shown in FIG. 1A, the agents of the present technology activate FXN to produce a greater than 8-fold increase in mRNA levels when administered to FRDA cells at a concentration of 1 μM after only 24 hours, thereby returning FXN mRNA to near-wild-type levels (See FIG. 1C). The ability to activate FXN mRNA production with relatively low concentrations of the agents of the present technology may be particularly advantageous in the clinical setting.

Agents, such as those disclosed herein, may also be useful in therapeutic methods targeting additional transcription elongation-based diseases or disorders involving genes which include multiple repeats of a GAA oligonucleotide sequence. Other related agents may be useful in therapeutic methods targeting additional putative transcription elongation-based disorders involving genes having multiple repeats of other short oligonucleotide sequences (containing e.g., 3 to 10 nucleotides), such as Fragile X syndrome (FXS), Fragile X-associated tremor/ataxia syndrome (FXTAS), myotonic dystrophy type 1 (DM type 1), and myotonic dystrophy type 2 (DM type 2). The sites of expansion and the affected sequence underlying each of these disorders are shown in Table 1.

TABLE 1

| Disease | Repeat | Gene | Gene location of the Repeat |
|---|---|---|---|
| Fragile X syndrome (FXS) | CGG | Fragile X Mental Retardation 1 (FMR1) | 5' UTR |
| Fragile X-associated tremor/ataxia syndrome (FXTAS) | CGG | Fragile X Mental Retardation 1 (FMR1) | 5' UTR |
| Myotonic dystrophy type 1 (DM type 1) | CTG | Dystrophia myotonica protein kinase (DMPK) | 3' UTR |
| Myotonic dystrophy type 2 (DM type 2) | CCTG | CNBP (ZNF9 or Zinc finger 9) | Intron 1 |
| Friedreich's ataxia (FA or FRDA) | GAA | Frataxin (FXN) | Intron 1 |

The methods disclosed herein can be used to stimulate FXN, FMR1, DMPK, or CNBP mRNA transcription by culturing the cells under cell-type specific conditions known in the art and contacting cells with an effective amount of one or more of the agents of the present technology according to any method known to those in the art for contacting a cell. In some embodiments of the methods disclosed herein, dorsal root ganglion neurons are used. In some embodiments of the methods disclosed herein, cardiomyocytes are used. In some embodiments of the methods disclosed herein, pancreatic beta cells are used. In some embodiments of the methods disclosed herein, peripheral blood mononuclear cells (PBMCs) are used. In some embodiments of the methods disclosed herein, B-lymphocytes are used. In some embodiments of the methods disclosed herein, lymphoblastoid cell lines are used. In some embodiments of the methods disclosed herein, fibroblasts are used. In some embodiments, the cells are derived from a patient subject.

In some embodiments, of the methods disclosed herein, the cells are contacted with one or more agents of the present technology at a concentration of about 10 nM. In some embodiments, the cells are contacted with one or more agents at a concentration of about 50 nM. In some embodiments, the cells are contacted with one or more agents at a concentration of about 100 nM. In some embodiments, the cells are contacted with one or more agents at a concentration of about 200 nM. In some embodiments, the cells are contacted with one or more agents at a concentration of about 300 nM. In some embodiments, the cells are contacted with one or more agents at a concentration of about 400 nM. In some embodiments, the cells are contacted with one or more agents at a concentration of about 500 nM. In some embodiments, the cells are contacted with one or more agents at a concentration of about 600 nM. In some embodiments, the cells are contacted with one or more agents at a concentration of about 700 nM. In some embodiments, the cells are contacted with one or more agents at a concentration of about 800 nM. In some embodiments, the cells are contacted with one or more agents at a concentration of about 900 nM. In some embodiments, the cells are contacted with one or more agents at a concentration of about 1 μM. In some embodiments, the cells are contacted with one or more agents at a concentration of about 2 μM. In some embodiments, the cells are contacted with one or more agents at a concentration of about 3 µM. In some embodiments, the cells are contacted with one or more agents at a concentration of about 4 µM. In some embodiments, the cells are contacted with one or more agents at a concentration of about 5 µM.

In some embodiments, of the methods disclosed herein, the cells are harvested for subsequent measurement of mRNA and/or protein levels at about 6 hours after having been contacted with one or more doses of the agents of the present technology. In some embodiments, of the methods disclosed herein, the cells are harvested for subsequent measurement of mRNA and/or protein levels at about 12 hours after having been contacted with one or more doses of the agents of the present technology. In some embodiments, of the methods disclosed herein, the cells are harvested for subsequent measurement of mRNA and/or protein levels at about 24 hours after having been contacted with one or more doses of the agents of the present technology. In some embodiments, the cells are harvested at about 2 days after having been contacted with one or more doses of the agents of the present technology. In some embodiments, the cells are harvested at about 3 days after having been contacted with one or more doses of the agents of the present technology. In some embodiments, the cells are harvested at about 4 days after having been contacted with one or more doses of the agents of the present technology. In some embodiments, the cells are harvested at about 5 days or more after having been contacted with one or more doses of the agents of the present technology.

In some embodiments, the present disclosure provides a method for modulating transcription of a gene that includes multiple repeats of an oligonucleotide sequence containing 3 to 10 nucleotides, such as a GAA oligonucleotide repeat expansion. Without wishing to be bound by theory, the modulation of transcription is effected by contacting the gene with an agent of the present technology having a formula A-L-B, wherein -L- is a linker; A- is a Brd4 binding moiety; and —B is a polyamide that specifically binds to one or more repeats of the oligonucleotide sequence, thereby modulating the transcription of the gene. In some embodiments, the gene is a frataxin (FXN) gene. In some embodiments, the number of repeats in the oligonucleotide expansion is greater than 50, greater than 70, greater than 100, or in a range of 66-1700. In some embodiments, the gene is the Fragile X Mental Retardation 1 (FMR1) gene. In some embodiments, the number of repeats in the oligonucleotide expansion is greater than 50, greater than 70, greater than 100, or greater than 200. In some embodiments, the gene is the dystrophia myotonica protein kinase (DMPK) gene. In some embodiments, the number of repeats in the oligonucleotide expansion is greater than 50, greater than 70, or greater than 100. In some embodiments, the gene is the CNBP (ZNF9 or zinc finger 9) gene. In some embodiments, the number of repeats in the oligonucleotide expansion is greater than 75, greater than 100, greater than 200, or in a range of 75-11,000.

In some embodiments, the present disclosure provides a method for increasing frataxin (FXN) mRNA levels in a cell comprising contacting the cell with an effective amount of any one or more of the agents described in Section IV. In some embodiments, the present disclosure provides a method for increasing Fragile X Mental Retardation 1 (FMR1) mRNA levels in a cell comprising contacting the cell with an effective amount of any one or more of the agents described in Section IV. In some embodiments, the present disclosure provides a method for increasing dystrophia myotonica protein kinase (DMPK) mRNA levels in a cell comprising contacting the cell with an effective amount of any one or more of the agents described in Section IV. In some embodiments, the present disclosure provides a method for increasing CNBP (ZNF9 or zinc finger 9) mRNA levels in a cell comprising contacting the cell with an effective amount of any one or more of the agents described in Section IV.

In some embodiments, the present disclosure provides a method for increasing frataxin (FXN) protein levels in a cell comprising contacting the cell with an effective amount of any one or more of the agents described in Section IV. In some embodiments, the present disclosure provides a method for increasing FMRP protein levels in a cell comprising contacting the cell with an effective amount of any one or more of the agents described in Section IV. In some embodiments, the present disclosure provides a method for increasing DMPK protein levels in a cell comprising contacting the cell with an effective amount of any one or more of the agents described in Section IV. In some embodiments, the present disclosure provides a method for increasing CNBP protein levels in a cell comprising contacting the cell with an effective amount of any one or more of the agents described in Section IV.

In some embodiments, the present disclosure provides a method for treating a genetic condition associated with a gene comprising a plurality of repeats of a GAA oligonucleotide sequence, comprising administering to the subject a therapeutically effective amount of any one or more of the agents described in Section IV. In some embodiments, the disease is Friedreich's ataxia (FRDA). In some embodiments, the present disclosure provides a method for treating a genetic condition associated with a gene comprising a plurality of repeats of a CGG oligonucleotide sequence, comprising administering to the subject a therapeutically effective amount of any one or more of the agents described in Section IV. In some embodiments, the disease is Fragile X syndrome (FXS). In some embodiments, the disease is Fragile X-associated tremor/ataxia syndrome (FXTAS). In some embodiments, the present disclosure provides a method for treating a genetic condition associated with a gene comprising a plurality of repeats of a CTG oligonucleotide sequence, comprising administering to the subject a therapeutically effective amount of any one or more of the agents described in Section IV. In some embodiments, the disease is Myotonic dystrophy type 1 (DM type 1). In some embodiments, the present disclosure provides a method for treating a genetic condition associated with a gene comprising a plurality of repeats of a CCTG oligonucleotide sequence, comprising administering to the subject a therapeutically effective amount of any one or more of the agents described in Section IV. In some embodiments, the disease is Myotonic dystrophy type 2 (DM type 2).

In some embodiments of the present method, the cell may include a fusion gene comprising a heterologous nucleotide sequence fused to the 3'-end of a gene comprising at least about 30 repeats of an oligonucleotide sequence containing 3 to 10 nucleotides, (e.g., 30 GAA repeats). In some embodiments, the gene comprising at least about 30 repeats of an oligonucleotide sequence is a frataxin (FXN) gene, a Fragile X Mental Retardation 1 (FMR1) gene, a dystrophia myotonica protein kinase (DMPK) gene, or a CNBP gene. In some embodiments, the heterologous nucleotide sequence comprises a reporter gene. In some embodiments, the reporter gene comprises a luminescence-based reporter gene. In some embodiments the luminescence-based reporter gene is a luciferase reporter gene, e.g., a gene encoding firefly luciferase, *Renilla* luciferase, or the like. In other embodiments, the reporter gene may be a gene for a selectable marker, e.g., an antibiotic resistance gene.

IV. Agents for the Modulation of Gene Expression

The present technology discloses an agent of the formula A-L-B, wherein -L- is a linker; A- is a Brd4 binding moiety; and —B is a nucleic acid binding moiety.

In some embodiments, the nucleic acid binding moiety (—B) specifically binds to a target oligonucleotide sequence. In some embodiments, the nucleic acid binding moiety (—B) specifically binds to one or more repeats of a short oligonucleotide sequence such as a GAA oligonucleotide sequence. In some embodiments, the nucleic acid binding moiety (—B) is a nucleic acid binding moiety, such as a polyamide that specifically binds to one or more repeats of an oligonucleotide containing 3 to 10 nucleotides, such as CGG, CTG, CCTG, and GAA oligonucleotide sequences. In some embodiments, the one or more repeats of an oligonucleotide may contain 3 to 6 nucleotides.

In some embodiments, that nucleic acid binding moiety (—B) comprises an oligonucleotide sequence (e.g., containing about 15 to 30 nucleotides) that is complementary to a desired target oligonucleotide sequence. In some embodiments, the nucleic acid binding moiety (—B) may be a nucleic acid sequence capable of hybridizing to one or more repeats of a GAA oligonucleotide sequence or to one or more repeats of a TTC oligonucleotide sequence. In some embodiments, the nucleic acid binding moiety (—B) may be a deoxyribonucleic acid (DNA) sequence, a ribonucleic acid (RNA) sequence, or a peptide nucleic acid (PNA) sequence capable of hybridizing to one or more repeats of a GAA oligonucleotide sequence or to one or more repeats of a TTC oligonucleotide sequence. For example, the nucleic acid binding moiety (—B) may be a deoxyribonucleic acid (DNA) sequence comprising, consisting of, or consisting essentially of one or more repeats of a TTC sequence, including, but not limited to, TTCTTCTTC, TTCTTCTTCTTC (SEQ ID NO:2), TTCTTCTTCTTCTTC (SEQ ID NO:3), TTCTTCTTCTTCTTCTTC (SEQ ID NO:4), and TTCTTCTTCTTCTTCTTCTTC (SEQ ID NO:5). In another example, the nucleic acid binding moiety (—B) may be a deoxyribonucleic acid (DNA) sequence comprising, consisting of, or consisting essentially of one or more repeats of a GAA sequence, including, but not limited to, GAAGAAGAA, GAAGAAGAAGAA (SEQ ID NO:6), GAAGAAGAAGAAGAA (SEQ ID NO:7), GAAGAAGAAGAAGAAGAA (SEQ ID NO:8), and GAAGAAGAAGAAGAAGAAGAA (SEQ ID NO:9). In another example, the nucleic acid binding moiety (—B) may be a ribonucleic acid (RNA) sequence comprising, consisting of, or consisting essentially of one or more repeats of a CUU sequence, including, but not limited to, CUUCUUCUU, CUUCUUCUUCUU (SEQ ID NO:10), CUUCUUCUUCUUCUU (SEQ ID NO:11), CUUCUUCUUCUUCUUCUU (SEQ ID NO:12), and CUUCUUCUUCUUCUUCUUCUU (SEQ ID NO:13).

In some embodiments, the nucleic acid binding moiety (—B) may be a deoxyribonucleic acid (DNA) sequence comprising, consisting of, or consisting essentially of 1 to 10, 1 to 15, 1 to 20, 1 to 25, 1 to 30, 1 to 35, 1 to 40, 1 to 45, 1 to 50, 1 to 55, 1 to 60, 1 to 65, 1 to 70, 1 to 75, 1 to 80, 1 to 85, 1 to 90, 1 to 95, 1 to 100, 1 to 150, 1 to 200, 1 to 250, 1 to 300, 1 to 350, 1 to 400, 1 to 450, 1 to 500, 1 to 550, 1 to 600, 1 to 650, 1 to 700, 1 to 750, 1 to 800, 1 to 850, 1 to 900, 1 to 950, or 1 to 1000 repeats of a TTC sequence. In some embodiments, the nucleic acid binding moiety (—B) may be a DNA sequence of 5 to 10 repeats of a TTC sequence (e.g., 15 to 30 nucleotide bases in length). In some embodiments, the nucleic acid binding moiety (—B) may be a DNA sequence of 5 to 6 repeats of a TTC sequence. In some embodiments, the nucleic acid binding moiety (—B) may be a DNA sequence of 5 to 7 repeats of a TTC sequence. In some embodiments, the nucleic acid binding moiety (—B) may be a DNA sequence of 5 to 8 repeats of a TTC sequence. In some embodiments, the nucleic acid binding moiety (—B) may be a DNA sequence of 5 to 9 repeats of a TTC sequence.

In some embodiments, the nucleic acid binding moiety (—B) may be a deoxyribonucleic acid (DNA) sequence comprising, consisting of, or consisting essentially of 1 to 10, 1 to 15, 1 to 20, 1 to 25, 1 to 30, 1 to 35, 1 to 40, 1 to 45, 1 to 50, 1 to 55, 1 to 60, 1 to 65, 1 to 70, 1 to 75, 1 to 80, 1 to 85, 1 to 90, 1 to 95, 1 to 100, 1 to 150, 1 to 200, 1 to 250, 1 to 300, 1 to 350, 1 to 400, 1 to 450, 1 to 500, 1 to 550, 1 to 600, 1 to 650, 1 to 700, 1 to 750, 1 to 800, 1 to 850, 1 to 900, 1 to 950, or 1 to 1000 repeats of a GAA sequence. In some embodiments, the nucleic acid binding moiety (—B) may be a DNA sequence of 5 to 10 repeats of a GAA sequence (e.g., 15 to 30 nucleotide bases in length). In some embodiments, the nucleic acid binding moiety (—B) may be a DNA sequence of 5 to 6 repeats of a GAA sequence. In some embodiments, the nucleic acid binding moiety (—B) may be a DNA sequence of 5 to 7 repeats of a GAA sequence. In some embodiments, the nucleic acid binding moiety (—B) may be a DNA sequence of 5 to 8 repeats of a GAA sequence. In some embodiments, the nucleic acid binding moiety (—B) may be a DNA sequence of 5 to 9 repeats of a GAA sequence.

In some embodiments, the nucleic acid binding moiety (—B) may be a ribonucleic acid (RNA) sequence comprising, consisting of, or consisting essentially of 1 to 10, 1 to 15, 1 to 20, 1 to 25, 1 to 30, 1 to 35, 1 to 40, 1 to 45, 1 to 50, 1 to 55, 1 to 60, 1 to 65, 1 to 70, 1 to 75, 1 to 80, 1 to 85, 1 to 90, 1 to 95, 1 to 100, 1 to 150, 1 to 200, 1 to 250, 1 to 300, 1 to 350, 1 to 400, 1 to 450, 1 to 500, 1 to 550, 1 to 600, 1 to 650, 1 to 700, 1 to 750, 1 to 800, 1 to 850, 1 to 900, 1 to 950, or 1 to 1000 repeats of a CUU sequence. In some embodiments, the nucleic acid binding moiety (—B) may be an RNA sequence of 5 to 10 repeats of a CUU sequence (e.g., 15 to 30 nucleotide bases in length). In some embodiments, the nucleic acid binding moiety (—B) may be an RNA sequence of 5 to 6 repeats of a CUU sequence. In some embodiments, the nucleic acid binding moiety (—B) may be an RNA sequence of 5 to 7 repeats of a CUU sequence. In some embodiments, the nucleic acid binding moiety (—B) may be an RNA sequence of 5 to 8 repeats of a CUU sequence. In some embodiments, the nucleic acid binding moiety (—B) may be an RNA sequence of 5 to 9 repeats of a CUU sequence.

In some embodiments, the nucleic acid binding moiety (—B) comprises a repeat-targeted duplex RNA, such as an anti-GAA duplex RNA that specifically targets GAA repeats. In some embodiments, the nucleic acid binding moiety (—B) comprises single-stranded locked nucleic acids (LNAs), such as anti-GAA LNA oligomers that specifically target GAA repeats.

The A- subunit is typically a triazolodiazepine Brd4 binding moiety, such as a thienotriazolodiazepine Brd4 binding moiety. The A- subunit and the polyamide —B subunit are commonly joined together by a linker -L- that has a backbone chain having at least 10 atoms, and commonly at least about 15 atoms.

In one aspect, A- is a triazolodiazepine Brd4 binding moiety. In some embodiments A- is a triazolodiazepine Brd4 binding moiety which may have a formula:

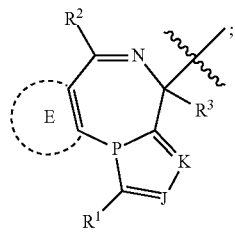

wherein J is N, O or $CR^{11}$; K is N, O or $CR^{11}$; with the proviso that J and K cannot both be —O—; P is N, except when one of J or K is O, then P is C; $R^1$ may be a hydrogen or optionally substituted alkyl, hydroxyalkyl, aminoalkyl, alkoxyalkyl, halogenated alkyl, hydroxyl, alkoxy, or —COOR$^4$; wherein $R^4$ may be a hydrogen, optionally substituted aryl, aralkyl, cycloalkyl, heteroaryl, heteroaralkyl, heterocycloalkyl, alkyl, alkenyl, alkynyl, or cycloalkylalkyl group optionally interrupted by one or more heteroatoms; $R^2$ may be an optionally substituted aryl, alkyl, cycloalkyl, or aralkyl group; $R^3$ may be a hydrogen, halogen, or optionally substituted alkyl group (e.g., —(CH$_2$)$_b$—C(O)N(R$^{20}$)(R$^{21}$), —(CH$_2$)$_b$—N(R$^{20}$)C(O)(R$^{21}$), or halogenated alkyl group, wherein b may be an integer from 1 to 10, and $R^{20}$ and $R^{21}$ may independently be a hydrogen or $C_1$-$C_6$ alkyl group (typically $R^{20}$ may be a hydrogen and $R^{21}$ may be a methyl)); $R^{11}$ may be a hydrogen or optionally substituted alkyl, cycloalkyl, heterocycloalkyl, aryl, or heteroaryl group; and Ring E may be an optionally substituted aryl or heteroaryl ring. In some embodiments, J may be N or $CR^{11}$. In some embodiments, P is N and J may be $CR^{11}$, where $R^{11}$ may be —CH$_3$. In some embodiments, both P and J may be N.

In some embodiments A- is a Brd4 binding moiety having a formula:

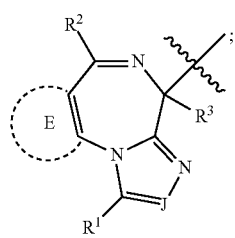

wherein $R^1$ may be a hydrogen or optionally substituted alkyl, hydroxyalkyl, aminoalkyl, alkoxyalkyl, halogenated alkyl, hydroxyl, alkoxy, or —COOR$^4$; wherein $R^4$ may be a hydrogen, optionally substituted aryl, aralkyl, cycloalkyl, heteroaryl, heteroaralkyl, heterocycloalkyl, alkyl, alkenyl, alkynyl, or cycloalkylalkyl group optionally interrupted by one or more heteroatoms; $R^2$ may be an optionally substituted aryl, alkyl, cycloalkyl, or aralkyl group; $R^3$ may be a hydrogen, halogen, or optionally substituted alkyl group (e.g., —(CH$_2$)$_b$—C(O)N(R$^{20}$)(R$^{21}$), —(CH$_2$)$_b$—N(R$^{20}$)C(O)(R$^{21}$), or halogenated alkyl group, wherein b may be an integer from 1 to 10, and $R^{20}$ and $R^{21}$ may independently be a hydrogen or $C_1$-$C_6$ alkyl group (typically $R^{20}$ may be a hydrogen and $R^{21}$ may be a methyl)); J may be N or $CR^{11}$, wherein $R^{11}$ may be a hydrogen or optionally substituted alkyl, cycloalkyl, heterocycloalkyl, aryl, or heteroaryl group; and Ring E may be an optionally substituted aryl or heteroaryl group. In some embodiments, J may be $CR^{11}$, wherein $R^{11}$ may be a —CH$_3$.

In some embodiments A- is a Brd4 binding moiety having a formula:

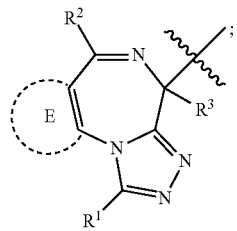

wherein $R^1$ may be a hydrogen or an optionally substituted alkyl, hydroxyalkyl, aminoalkyl, alkoxyalkyl, halogenated alkyl, hydroxyl, alkoxy, or —COOR$^4$; wherein $R^4$ may be a hydrogen, or optionally substituted aryl, aralkyl, cycloalkyl, heteroaryl, heteroaralkyl, heterocycloalkyl, alkyl, alkenyl, alkynyl, or cycloalkylalkyl group optionally interrupted by one or more heteroatoms; $R^2$ may be an optionally substituted aryl, alkyl, cycloalkyl, or aralkyl group; $R^3$ may be a hydrogen, halogen, or optionally substituted alkyl group (e.g., —(CH$_2$)$_x$—C(O)N(R$^{20}$)(R$^{21}$), —(CH$_2$)$_x$—N(R$^{20}$)C(O)(R$^{21}$), or halogenated alkyl group, wherein x may be an integer from 1 to 10, and $R^{20}$ and $R^{21}$ may independently be a hydrogen or $C_1$-$C_6$ alkyl group (typically $R^{20}$ may be a hydrogen and $R^{21}$ may be a methyl)); and Ring E may be an optionally substituted aryl or heteroaryl group. In some embodiments, x may be an integer from 1 to 6. In some embodiments, x may be an integer from 1 to 3.

In some embodiments, A- is a Brd4 binding moiety having a formula:

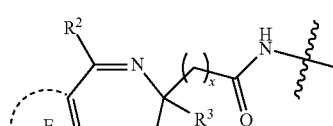

or

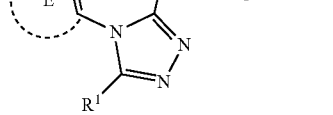

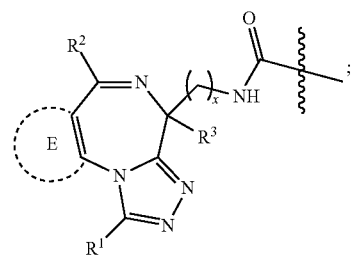

wherein x, $R^1$, $R^2$, $R^3$, and Ring E are as defined herein.

In some embodiments, A- is a thienotriazolodiazepine Brd4 binding moiety. In some embodiments A- is a Brd4 binding moiety having a formula:

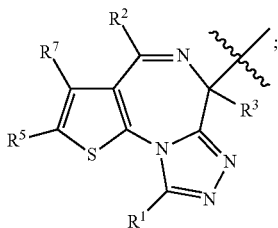

wherein $R^2$ may be an aryl group optionally substituted with halogen, $-OR^6$, $-SR^6$, $-N(R^6)_2$, $-N(R^6)COR^9$, or one or more optionally substituted alkyl, alkenyl, alkynyl, aryl, heteroaryl, amino, or amido groups, wherein $R^6$ and $R^9$ may independently be a hydrogen or alkyl group; $R^1$ and $R^3$ may independently be a hydrogen or optionally substituted alkyl group; and $R^5$ and $R^7$ may independently be a hydrogen, alkyl, alkenyl, alkynyl, halogen, $-OH$, $-SH$, or $-NH_2$. In some embodiments, $R^2$ may be a phenyl group optionally substituted with one or more alkyl, cyano, halogenated alkyl, alkoxy, hydroxyalkyl, and/or halogen substituents. In some embodiments, $R^2$ may be a phenyl group optionally substituted with one or more halogenated alkyl groups. In some embodiments, $R^2$ may be a phenyl group optionally substituted with one or more halogens. In some embodiments, $R^2$ may be a phenyl group substituted with one, two, three, four or five halogens.

In some embodiments, A- is a thienotriazolodiazepine Brd4 binding moiety having a formula:

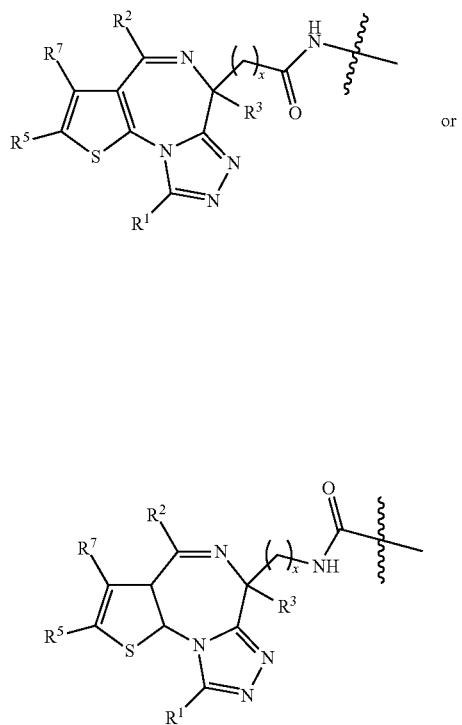

wherein x, $R^1$, $R^2$, $R^3$, $R^5$, and $R^7$ are as defined herein.

In some embodiments A- is a Brd4 binding moiety having a formula:

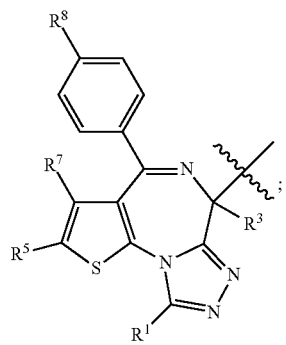

wherein $R^3$ may be a hydrogen or optionally substituted $C_1$-$C_6$ alkyl group; $R^1$, $R^5$, and $R^7$ are each independently hydrogen, methyl, ethyl, or halomethyl (e.g., trifluoromethyl); and $R^8$ may be a halogen, optionally substituted aryl, amino, or amido group. In some embodiments, $R^3$ may be a hydrogen or $-CH_3$. In some embodiments, $R^3$ may be $-CH_3$. In some embodiments, $R^1$, $R^5$, and $R^7$ are each independently hydrogen, methyl, ethyl, or trifluoromethyl. In some embodiments, $R^1$, $R^5$, and $R^7$ are each methyl or ethyl. In some embodiments, $R^1$, $R^5$, and $R^7$ are each ethyl. In some embodiments, $R^1$, $R^5$, and $R^7$ are each methyl. In some embodiments, $R^1$, $R^5$, and $R^7$ are each independently hydrogen. In some embodiments, $R^5$, and $R^7$ are each independently trifluoromethyl. In some embodiments, $R^3$ may be hydrogen or $-CH_3$; $R^1$, $R^5$, and $R^7$ may be methyl; and $R^8$ may be chloro. In some embodiments, $R^3$ may be hydrogen; $R^1$, $R^5$, and $R^7$ may be methyl; and $R^8$ may be chloro. In some embodiments, $R^1$ may be a hydrogen, methyl, ethyl, or halomethyl. In some embodiments, $R^1$ may be a trifluoromethyl.

In some embodiments, $R^8$ may be a halogen. In some embodiments, $R^8$ may be $-Cl$. In some embodiments, $R^8$ may be $-F$. In some embodiments, $R^8$ may be a phenyl group optionally substituted with one or more cyano and/or alkoxy groups. In some embodiments, $R^8$ may be a phenyl group substituted with a cyano group. In some embodiments, $R^8$ may be a phenyl group substituted with a methoxy group. In some embodiments, $R^8$ may be an optionally substituted amino group. In some embodiments, $R^8$ may be an amino group substituted with an optionally substituted phenyl, benzyl, or heteroaryl group and/or alkyl group. In some embodiments, $R^8$ may be an amino group substituted with a phenyl group. In some embodiments, $R^8$ may be an amino group substituted with a halogenated phenyl group. In some embodiments, $R^8$ may be an amino group substituted with a methyl and a halogenated phenyl group. In some embodiments, $R^8$ may be an amino group substituted with a heteroaryl group. In some embodiments, $R^8$ may be an amino group substituted with a pyridyl group. In some embodiments, $R^8$ may be an amino group substituted with a benzyl group. In some embodiments, $R^8$ may be an amido group substituted with an alkyl, aralkyl, or alkaryl group. In some embodiments, $R^8$ may be an amido group substituted with an aralkyl group. In some embodiments, $R^8$ may be an amido group substituted with $-(CH_2)_t$-phenyl group, wherein t is an integer from 1 to 10. In some embodiments, t may be 1 or 2.

In some embodiments A- is a Brd4 binding moiety having a formula:

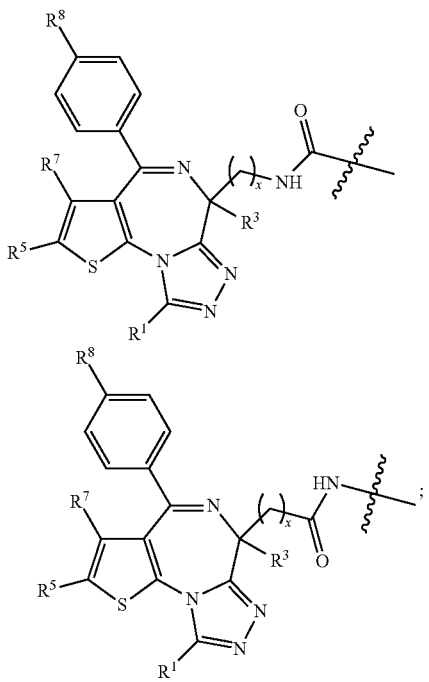

wherein x, $R^1$, $R^3$, $R^5$, $R^7$, and $R^8$ are as defined herein.

In some embodiments A- is a Brd4 binding moiety having a formula:

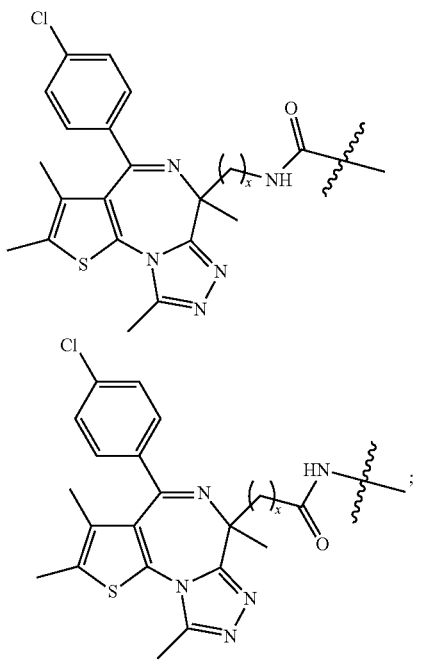

wherein x is as defined herein.

As an alternative to a triazolodiazepine Brd4 binding moiety, other Brd4 ligands may be used as the A- subunit of the present agent. For example, the agent may include a delta-carboline (5H-pyrido[3,2-b]indole) Brd4 ligand, such as compounds of the type represented by the structure shown below, as the Brd4 binding moiety. Suitable examples of such a delta-carboline Brd4 ligands are described in US 2016/0176864, the disclosure of which is herein incorporated by reference. Such Brd4 ligands may be attached to the linker subunit -L- of the present agents by a covalent bond to any ring or substituent of the delta-carboline ligand which does not substantially alter the binding of the ligand to Brd4.

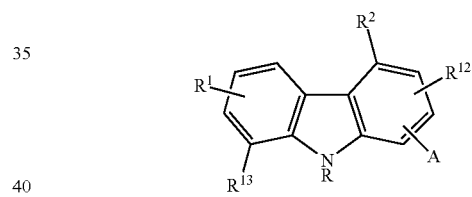

In some embodiments, the agent may include a carbazole Brd4 ligand, such as compounds of the type represented by the structure shown below, as the Brd4 binding moiety. Suitable examples of such a carbazole Brd4 ligands are described in U.S. Pat. No. 9,492,460 B2, the disclosure of which is herein incorporated by reference. Such Brd4 ligands may be attached to the linker subunit -L- of the present agents by a covalent bond to any ring or substituent of the carbazole ligand which does not substantially alter the binding of the ligand to Brd4.

In the carbazole structure shown above, $R^2$ is typically —COOH, or —CONR$^7$R$^8$; A is an optionally substituted heteroaryl or optionally substituted heterocyclo; such as an optionally substituted isoxazole, oxazole or triazole group, and R is 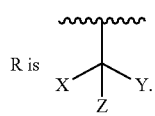

In some embodiments, the agent may include a pyrrolo[2,3-C]pyridine and pyrazolo[2,3-C]pyridine Brd4 ligand, such as compounds of the type represented by the structure shown below, as the Brd4 binding moiety. Suitable examples of such a pyrrolo[2,3-C]pyridine and pyrazolo[2,3-C]pyridine Brd4 ligands are described in U.S. Pat. No. 9,399,640, the disclosure of which is herein incorporated by reference. Such Brd4 ligands may be attached to the linker subunit -L- of the present agents by a covalent bond to any ring or substituent of the ligand which does not substantially alter the binding of the ligand to Brd4.

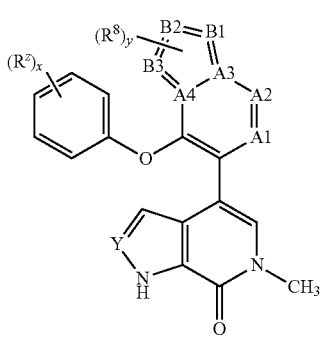

In the structure shown above, the 5-membered ring formed by A3, A4, B1, B2, and B3 is (1) an optionally substituted 5-membered heterocyclyl wherein B1 and B3 are NH, B2 is CH, N, or C(O), and A3 and A4 are C.

In some embodiments, the agent may include a triazolopyrazine Brd4 ligand, such as compounds of the type represented by the structure shown below (where $X_4$ is —CR═ and $X_5$ is —N═), as the Brd4 binding moiety. Suitable examples of such a triazolopyrazine Brd4 ligands are described in WO/2015/067770, the disclosure of which is herein incorporated by reference. Such Brd4 ligands may be attached to the linker subunit -L- of the present agents by a covalent bond to any ring or substituent of the ligand which does not substantially alter the binding of the ligand to Brd4.

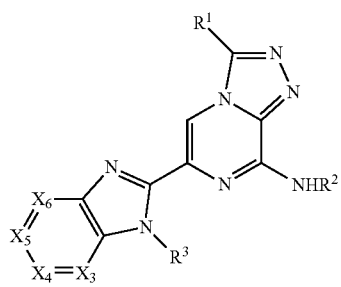

In some embodiments, the agent may include a pyridinone Brd4 ligand, such as compounds of the type represented by the structure shown below (where zero, one or two of $X_3$, $X_4$, $X_5$ and $X_6$ is —N═ and the remainder are —CR═), as the Brd4 binding moiety. Suitable examples of such a pyridinone Brd4 ligands are described in WO 2015/022332, the disclosure of which is herein incorporated by reference. Such Brd4 ligands may be attached to the linker subunit -L- of the present agents by a covalent bond to any ring or substituent of the pyridinone ligand which does not substantially alter the binding of the ligand to Brd4.

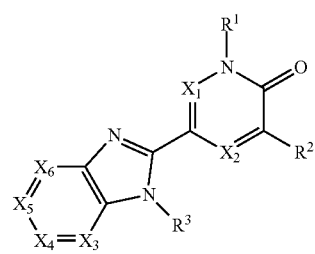

In some embodiments, the agent may include a quinazolinine Brd4 ligand, such as compounds of the type represented by the structure shown below (where X is N or CH; Y is —NH— and $R_6$ is hydrogen, alkoxy, alkyl, halogen, aminoalkyl, or thioalkyl), as the Brd4 binding moiety. Suitable examples of such a quinazolinine Brd4 ligands are described in WO 2015/015318, the disclosure of which is herein incorporated by reference. Such Brd4 ligands may be attached to the linker subunit -L- of the present agents by a covalent bond to any ring or substituent of the quinazolinine ligand which does not substantially alter the binding of the ligand to Brd4.

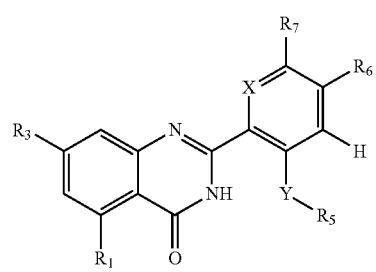

In some embodiments, the —B subunit of the present agent may comprise one or more of the following subunits:

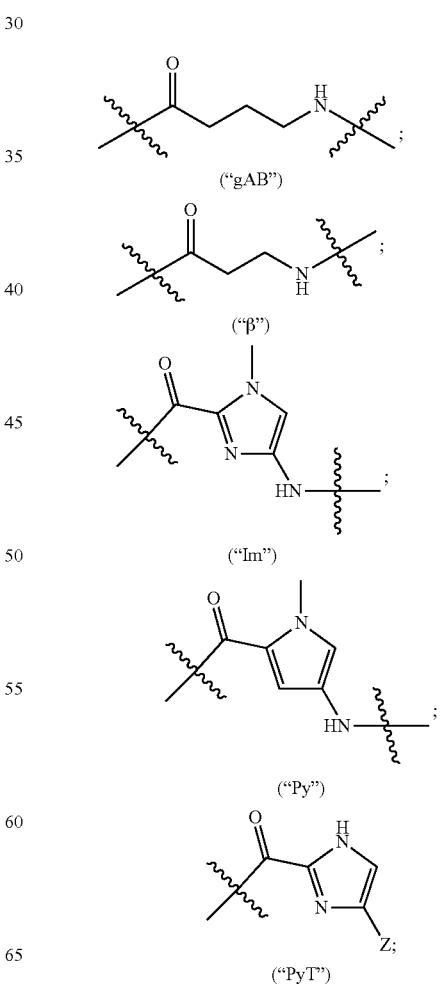

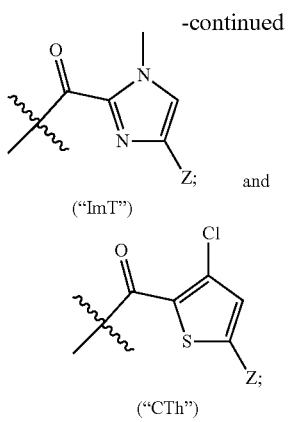

("ImT") and ("CTh")

wherein Z is typically hydrogen, amino, or an amido group.

In some embodiments, —B may specifically bind to one or more repeats of a CGG, CTG, CCTG, or GAA oligonucleotide sequence.

In some embodiments, —B may specifically bind to one or more repeats of a CGG oligonucleotide sequence. In some embodiments, —B may include a polyamide sequence selected from the group consisting of:

Im-Py-Py-Im-gAB-Py-Im-Im-Py-;  -Im-Py-Py-Im-gAB-Py-Im-Im-PyT;
Im-Py-Py-Im-gAB-Py-Im-Im-β-;  -Im-Py-Py-Im-gAB-Py-Im-Im-β-G;
Im-β-Py-Im-gAB-Py-Im-Im-β-;  -Im-β-Py-Im-gAB-Py-Im-Im-β-G;
Im-β-Py-Im-gAB-Py-Im-Im-Py-;  -Im-β-Py-Im-gAB-Py-Im-Im-PyT;
Py-Py-Im-β-gAB-Im-Py-Im-Im-;  -Py-Py-Im-β-gAB-Im-Py-Im-ImT;
Py-Py-Im-Py-gAB-Im-Py-Im-Im-;  -Py-Py-Im-Py-gAB-Im-Py-Im-ImT;
Py-Py-Im-β-gAB-Im-β-Im-Im-; -Py-Py-Im-β-gAB-Im-3-Im-ImT;
Py-Py-Im-Py-gAB-Im-β-Im-Im-;  -Py-Py-Im-Py-gAB-Im-β-Im-ImT;
Im-β-Py-gAB-Im-Im-Py-; -Im-β-Py-gAB-Im-Im-PyT;
Im-β-Py-gAB-Im-Im-β-; -Im-β-Py-gAB-Im-Im-β-G;
Im-Py-Py-gAB-Im-Im-β-; -Im-Py-Py-gAB-Im-Im-β-G;
Im-Py-Py-gAB-Im-Im-Py-; -Im-Py-Py-gAB-Im-Im-PyT;
Im-β-Py-gAB-Im-Im-Py-; and -Im-β-Py-gAB-Im-Im-PyT;

wherein G may be hydrogen, alkyl, alkenyl, alkynyl, or —C(O)—$R^B$; and $R^B$ may be a hydrogen, $C_1$-$C_6$ alkyl, $C_1$-$C_6$ alkenyl, or $C_1$-$C_6$ alkynyl group.

In some embodiments, —B may specifically bind to one or more repeats of a CTG oligonucleotide sequence. In some embodiments, —B may include a polyamide sequence selected from the group consisting of:

Im-Py-Py-Im-gAB-Py-Im-Py-Py-;  -Im-Py-Py-Im-gAB-Py-Im-Py-PyT;
Im-β-Py-Im-gAB-Py-Im-Py-Py-;  -Im-β-Py-Im-gAB-Py-Im-Py-PyT;
Im-Py-Py-Im-gAB-Py-Im-β-Py-;  -Im-Py-Py-Im-gAB-Py-Im-β-PyT;
Im-β-Py-Im-gAB-Py-Im-β-Py-;  -Im-β-Py-Im-gAB-Py-Im-β-PyT
Py-Im-β-Im-gAB-Py-Py-Py-Im-;  -Py-β-Im-gAB-Py-Py-Py-ImT;
Py-Im-Py-Im-gAB-Py-Py-Py-Im-;  -Py-Im-Py-Im-gAB-Py-Py-Py-ImT;
Py-Im-Py-Py-gAB-Im-Py-Py-Im-;  -Py-Im-Py-Py-gAB-Im-Py-Py-ImT;
Py-Im-β-Py-gAB-Im-Py-Py-Im-;  -Py-Im-β-Py-gAB-Im-Py-Py-ImT;
Py-Im-Py-Py-gAB-Im-β-Py-Im-;  -Py-Im-Py-Py-gAB-Im-β-Py-ImT;
Py-Im-β-Py-gAB-Im-β-Py-Im-; -Py-Im-β-Py-gAB-Im-β-Py-ImT;
Py-Im-Py-Py-gAB-Im-β-Py-Im-;  -Py-Im-Py-Py-gAB-Im-β-Py-ImT;
Im-β-Py-gAB-Im-Py-Py-; -Im-β-Py-gAB-Im-Py-PyT;
Im-β-Py-gAB-Im-β-PyT;
Im-Py-Py-gAB-Im-Py-Py-; -Im-Py-Py-gAB-Im-Py-PyT;
Im-Py-Py-gAB-Im-β-Py-;  and  -Im-Py-Py-gAB-Im-β-PyT.

In some embodiments, —B may specifically bind to one or more repeats of a CCTG oligonucleotide sequence. In some embodiments, —B may include a polyamide sequence selected from the group consisting of:

Py-Im-Im-β-gAB-Py-Py-Py-ImT;
Py-Im-Im-Py-gAB-Py-Py-Py-Im-;  -Py-Im-Im-Py-gAB-Py-Py-Py-ImT;
Py-Im-Im-gAB-Py-Py-Im-; -Py-Im-Im-gAB-Py-Py-ImT;
Py-Py-Im-Im-gAB-Py-Py-Im-Py-;  -Py-Py-Im-Im-gAB-Py-Py-Im-PyT;
Im-Py-Py-gAB-Im-β-PyT;
Im-β-Py-gAB-Im-Py-PyT;
Im-β-Py-gAB-Im-β-PyT;
Im-Py-Py-gAB-Im-Py-Py-; and -Im-Py-Py-gAB-Im-Py-PyT;

wherein G may be hydrogen, alkyl, alkenyl, alkynyl, or —C(O)—$R^B$; and $R^B$ may be a hydrogen, $C_1$-$C_6$ alkyl, $C_1$-$C_6$ alkenyl, or $C_1$-$C_6$ alkynyl group.

In some embodiments, the one or more repeats may be GAA. In some embodiments, —B may specifically bind to a one or more repeats of a GAA oligonucleotide sequence. In some embodiments, —B may include —X-(β-Py-Im)$_n$-β-Py-TRM; where X is -β-Im-, -β-Py-, -β-, or a bond; n is 1-10; and -TRM is -ImT or -CTh; with the proviso that one of the -β-Py-Im- trimers may be replaced by a -β-Im-Im- trimer. In some embodiments, —B may include —X-(β-Py-Im)$_n$-(β-Py-ImT); wherein: X is -β-Im-, -β-Py-, -β-, or a bond; Z is hydrogen, amino, or amido group; and n is 0 to 10; with the proviso that when n is at least 1, one of the -β-Py-Im- trimers may be replaced by a -β-Im-Im- trimer.

In some embodiments, Z may be —$NR^BR^B$ or —$N^+R^A R^BR^B$; wherein $R^A$ may be hydrogen; and $R^B$ may be a hydrogen, $C_1$-$C_6$ alkyl, $C_1$-$C_6$ alkenyl, or $C_1$-$C_6$ alkynyl group. In some embodiments, Z may be —$N(R^A)C(O)R^B$; wherein $R^A$ may be hydrogen; and $R^B$ may be a hydrogen, $C_1$-$C_6$ alkyl, $C_1$-$C_6$ alkenyl, or $C_1$-$C_6$ alkynyl group. In some embodiments, $R^B$ may be hydrogen or $C_1$-$C_6$ alkyl group. In some embodiments, $R^B$ may be hydrogen or —$CH_3$. In certain embodiments, Z may be —$NH_2$. In certain embodiments, Z may be —$NH_3^+$. In certain embodiments, Z may be hydrogen.

In some embodiments, n may be an integer from 1 to 10. In some embodiments, n may be 1, 2, 3, 4, or 5. In certain embodiments, n may be 1 or 2. In some embodiments, n may be 1 or 2 and none of the -β-Py-Im- trimers are replaced by a -β-Im-Im- trimer. In some embodiments, n may be 1 or 2 and one of the -β-Py-Im- trimers is replaced by a -β-Im-Im-timer.

In some embodiments, —B may be -(β-Py-Im)$_n$-(β-Py-ImT); where Z may be hydrogen or —$NH_3^+$ and n may be 1 or 2.

In some embodiments, —B may include -β-Im-β-Py-Im-β-Py-Im-β-Py-ImT, -β-β-Py-Im-β-Py-Im-β-Py-ImT, and/or -β-β-Py-Im-β-Py-Im-β-Py-ImT; in which Z may be hydrogen. In some embodiments, —B may include β-Im-β-Py-Im-β-Py-Im-β-Py-ImT, β-Im-β-Py-Im-β-Im-Im-β-Py-ImT, and/or (-β-Im-β-Im-Im-β-Py-Im-β-Py-ImT; in which Z may be hydrogen. In some embodiments, —B may include -β-Py-β-Py-Im-β-Py-ImT, -β-β-Py-Im-β-Py-ImT, -β-Im-β-Py-Im-β-Py-ImT, -β-Py-β-Py-Im-β-Py-Im-β-Py-ImT, -β-Py-Im-β-Py-Im-β-Py-ImT, -β-Py-β-Py-Im-β-Py-CTh and/or -β-β-Py-Im-β-Py-Im-β-Py-ImT, -β-Py-Im-β-Py-CTh.

Figure 15:
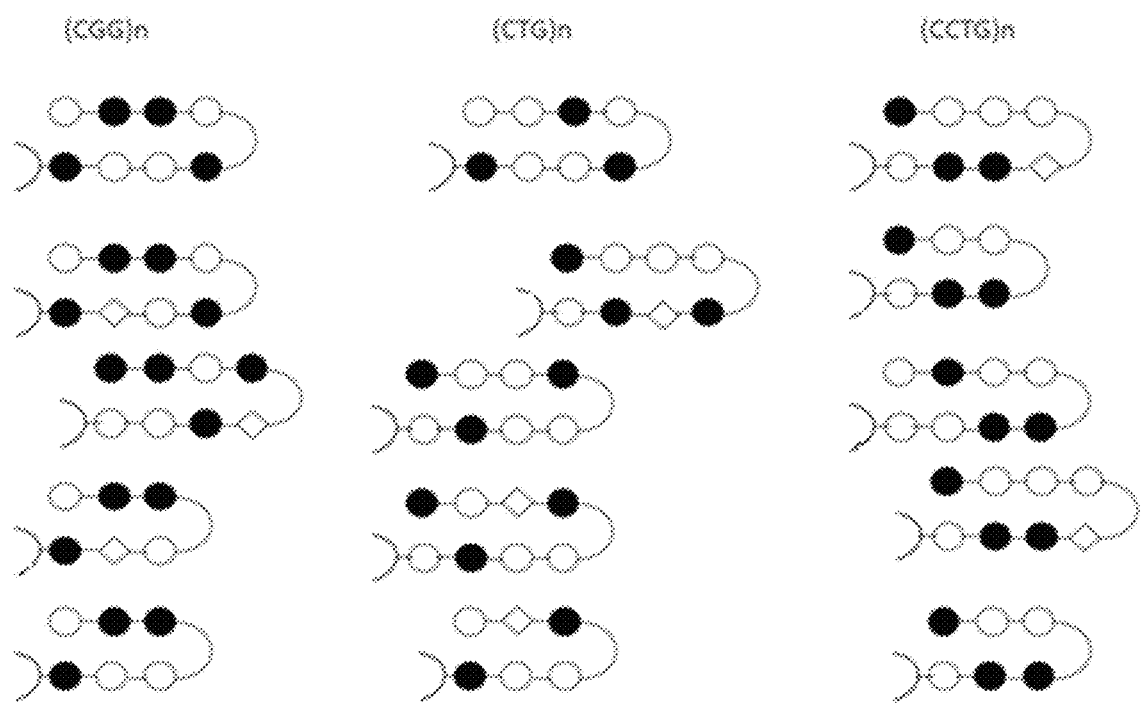
FIG. 15 shows Scheme 4 depicting exemplary polyamides used to bind CGG, CTG, and CCTG repeats.

Exemplary —B subunits include, but are not limited to, those in Scheme 4 (FIG. 15), wherein the open circle represents Py, the terminating open circle represents PyT, the filled circle represents Im, the terminating filled circle represents ImT, the open diamond represents β, and the turn represents gAB. In some embodiments, Py at any position may be replaced with β. In some embodiments, PyT may be replaced with β-H or β-alkyl. In some embodiments, β at any position may be replaced with Py.

Other —B subunits may be provided following Table 2 as provided below.

TABLE 2

| Pair | Base Pairing | | | |
|---|---|---|---|---|
| | G·C | C·G | T·A | A·T |
| Im/β | + | − | − | − |
| β/Im | − | + | − | − |
| Py/β | − | − | + | + |
| β/Py | − | − | + | + |
| β/β | − | − | + | + |
| Py/Py | − | − | + | + |
| Im/Im | − | − | − | − |

*a* Favored (+), disfavored (−)

The A- subunit and the —B subunit are commonly joined together by a linker -L- that has a chain having at least 10 contiguous atoms, and commonly at least about 15 contiguous atoms in the backbone chain of the linker. In some embodiments, -L- may have a backbone chain that includes about 15 to 250 atoms. In some embodiments, the linker -L- may desirably have a backbone chain that includes no more than about 50 contiguous atoms in the backbone of the linker, often no more than about 40 contiguous atoms, and in many instances no more than about 30 contiguous atoms in the backbone chain of the linker. It is quite common for the linker -L- to have a backbone chain that includes about 15 to 25 contiguous atoms in the backbone of the linker.

In some embodiments -L- may be a covalent linking group. In some embodiments, -L- may be a combination of one or more optionally substituted arylene, aralkylene, cycloalkylene, heteroarylene, heteroaralkylene, heterocycloalkylene, alkylene, alkenylene, alkynylene, or cycloalkylalkylene, optionally interrupted by one or more heteroatoms, amido, or carboxyl groups. In some embodiments, -L- may include a combination of one or more linking moieties selected from the group consisting of —O—, —(CH$_2$)$_x$—, —(CH$_2$CH$_2$CH$_2$O)$_y$—, —(OCH$_2$CH$_2$CH$_2$)$_y$—, —(CH$_2$CH$_2$O)$_y$—, —(OCH$_2$CH$_2$)$_y$—, —C(O)NR'—, —NR'C(O)—, —C(O)—, —NR*—, and

wherein R' and R* are each independently a hydrogen or C$_1$-C$_6$ alkyl; and x and y are each independently an integer from 1 to 10. In some embodiments, R' may be a hydrogen and R* may be —CH$_3$.

In some embodiments, -L- may include —(CH$_2$)$_x$—C(O)N(R')—(CH$_2$)$_Q$—N(R*)—(CH$_2$)$_Q$—N(R')C(O)—(CH$_2$)$_x$—C(O)N(R')—, —(CH$_2$)$_x$—C(O)N(R')—(CH$_2$CH$_2$O)$_y$—(CH$_2$)$_x$—C(O)N(R')—, —C(O)N(R')—(CH$_2$)$_y$—N(R*)—(CH$_2$)$_Q$—N(R')C(O)—(CH$_2$)$_x$—, —(CH$_2$)$_x$—O—(CH$_2$CH$_2$)$_y$—(CH$_2$)$_x$—N(R')C(O)— (CH$_2$)$_x$—, or —N(R')C(O)— (CH$_2$)$_x$—C(O)N(R')—(CH$_2$)$_x$—O—(CH$_2$CH$_2$O)$_y$—(CH$_2$)$_x$—, wherein R* may be methyl, R' may be hydrogen, Q may be an integer from 2 to 10, and x and y may independently be an integer from 1 to 10. In some embodiments, R' may be a hydrogen; R* may be —CH$_3$; x and y may independently be an integer from 1 to 3; and Q may be 2 or 3.

In some embodiments, -L- may include one or more linking moieties selected from Gly-Ser-Gly, (Gly-Ser-Gly)v (SEQ ID NOS:14 and 22-29), Gly-Gly-Ser, and (Gly-Gly-Ser)w (SEQ ID NOS:15 and 30-37), where v and w are typically an integer from 2 to about 10.

In one aspect, the present technology discloses an agent having a formula A-L-B, wherein -L- is a covalent linker having a backbone chain, which typically includes at least 10 atoms; —B is a polyamide that specifically binds to one or more repeats of a particular oligonucleotide sequence containing 3 to 10 nucleotides; and A- is a Brd4 binding moiety, such as a triazolodiazepine Brd4 binding moiety. In some embodiments, the one or more repeats of an oligonucleotide may contain 3 to 6 nucleotides. For example, the polyamide subunit may specifically bind to one or more repeats of a particular oligonucleotide sequence, which contains 3 or 4 nucleotides.

In one aspect, the present technology discloses an agent having a formula A-L-B, wherein -L- is a linker having a backbone chain which may include at least 10 atoms; —B is a polyamide that specifically binds to one or more repeats of a GAA oligonucleotide sequence; and A- is a triazolodiazepine Brd4 binding moiety having a structure:

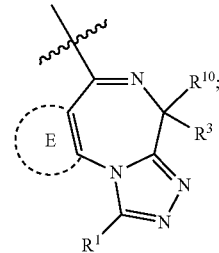

wherein R$^3$ and R$^{10}$ may independently be a hydrogen, halogen, or optionally substituted alkyl group (e.g., —(CH$_2$)$_x$—C(O)N(R$^{20}$)(R$^{21}$), —(CH$_2$)$_x$—N(R$^{20}$)C(O)(R$^{21}$), or halogenated alkyl group, wherein R$^{20}$ and R$^{21}$ may independently be a hydrogen or C$_1$-C$_6$ alkyl group (typically R$^{20}$ may be a hydrogen and R$^{21}$ may be a methyl), and x is as defined herein); R$^1$ may be a hydrogen or optionally substituted alkyl, hydroxyl, alkoxy, or —COOR$^4$; wherein R$^4$ may be a hydrogen, optionally substituted aryl, aralkyl, cycloalkyl, heteroaryl, heteroaralkyl, heterocycloalkyl, alkyl, alkenyl, alkynyl, or cycloalkylalkyl group optionally interrupted by one or more heteroatoms; and Ring E may be an optionally substituted aryl or heteroaryl group. In some embodiments, R$^1$ may be a hydroxyalkyl, aminoalkyl, alkoxyalkyl, or halogenated alkyl group. In some embodiments, $R^1$ may be a hydrogen, methyl, ethyl, or halomethyl. In some embodiments, $R^1$ may be a trifluoromethyl.

In some embodiments, $R^3$ and $R^{10}$ may independently be a hydrogen or optionally substituted alkyl. In some embodiments, $R^3$ and $R^{10}$ may independently be hydrogen or optionally substituted $C_1$-$C_6$ alkyl group. In some embodiments, $R^3$ and $R^{10}$ may independently be a —$(CH_2)_x$—C(O)N(R')R", wherein R' and R" are each independently a hydrogen or $C_1$-$C_6$ alkyl and x is an integer from 1 to 10. In some embodiments, R' is a hydrogen. In some embodiment R" is a —$CH_3$. In some embodiments, A- is a thienotriazolodiazepine Brd4 binding moiety. In some embodiment, -L- is a linker as defined herein and —B is a polyamide as defined herein.

V. Modes of Administration and Pharmaceutical Compositions

Any method known to those in the art for contacting a cell, organ, or tissue with compositions such as the agents of the present technology, or pharmaceutically acceptable salts thereof, may be employed. Suitable methods include in vitro, ex vivo, or in vivo methods.

In vitro methods typically include cultured samples. For example, a cell can be placed in a reservoir (e.g., tissue culture plate), and incubated with an agent under appropriate conditions suitable for obtaining the desired result. Suitable incubation conditions can be readily determined by those skilled in the art.

Ex vivo methods typically include cells, organs, or tissues removed from a mammal, such as a human. The cells, organs or tissues can, for example, be incubated with the agent under appropriate conditions. The contacted cells, organs, or tissues are typically returned to the donor, placed in a recipient, or stored for future use. Thus, the compound is generally in a pharmaceutically acceptable carrier.

In vivo methods typically include the administration of an agent such as those described herein, to a mammal such as a human. When used in vivo for therapy, an agent of the present technology is administered to a mammal in an amount effective in obtaining the desired result or treating the mammal.

An effective amount of an agent of the present technology useful in the present methods, such as in a pharmaceutical composition or medicament, may be administered to a mammal in need thereof by any of a number of well-known methods for administering pharmaceutical compositions or medicaments. The agents of the present technology may be administered systemically or locally.

The agents of the present technology may be formulated as a pharmaceutically acceptable salt. The term "pharmaceutically acceptable salt" means a salt prepared from a base or an acid which is acceptable for administration to a patient, such as a mammal (e.g., salts having acceptable mammalian safety for a given dosage regimen).

The agents of the present technology described herein can be incorporated into pharmaceutical compositions for administration, singly or in combination, to a subject for the treatment or prevention of a genetic condition comprising at least about 50 repeats of an oligonucleotide sequence having 3 to 10 nucleotides. The agents of the present technology described herein can be incorporated into pharmaceutical compositions for administration, singly or in combination, to a subject for the treatment or prevention of a genetic condition associated with a gene comprising a plurality of repeats of a GAA oligonucleotide sequence, such as Friedreich's ataxia (FR or FRDA). In addition, the agents of the present technology described herein can be incorporated into pharmaceutical compositions for administration, singly or in combination, to a subject for the treatment or prevention of genetic condition associated with a gene comprising a plurality of repeats of a CGG oligonucleotide sequence, such as Fragile X syndrome (FXS) or Fragile X-associated tremor/ataxia syndrome (FXTAS). In addition, the agents of the present technology described herein can be incorporated into pharmaceutical compositions for administration, singly or in combination, to a subject for the treatment or prevention of genetic condition associated with a gene comprising a plurality of repeats of a CTG oligonucleotide sequence, such as myotonic dystrophy type 1 (DM type 1). In addition, the agents of the present technology described herein can be incorporated into pharmaceutical compositions for administration, singly or in combination, to a subject for the treatment or prevention of genetic condition associated with a gene comprising a plurality of repeats of a CCTG oligonucleotide sequence, such as myotonic dystrophy type 2 (DM type 2). Such compositions typically include the active agent and a pharmaceutically acceptable carrier. As used herein the term "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

Pharmaceutical compositions are typically formulated to be compatible with the intended route of administration. Routes of administration include, for example, parenteral (e.g., intravenous, intradermal, intraperitoneal or subcutaneous), oral, respiratory (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates, and agents for the adjustment of tonicity, such as sodium chloride or dextrose. The pH can be adjusted with acids or bases, such as hydrochloric acid or sodium hydroxide. The preparation can be enclosed in ampoules, disposable syringes or multiple-dose vials made of glass or plastic. For convenience of the patient or treating physician, the dosing formulation can be provided in a kit containing all necessary equipment (e.g., vials of drug, vials of diluent, syringes and needles) for a course of treatment (e.g., 7 days of treatment).

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL® (BASF, Parsippany, N.J., USA) or phosphate buffered saline (PBS). In all cases, a composition for parenteral administration must be sterile and should be formulated for ease of syringeability. The composition should be stable under the conditions of manufacture and storage, and must be shielded from contamination by microorganisms such as bacteria and fungi.

The pharmaceutical compositions can include a carrier, which can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thiomerasol, and the like. Glutathione and other antioxidants can be included to prevent oxidation. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, aluminum monostearate or gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, typical methods of preparation include vacuum drying and freeze drying, which can yield a powder of the active ingredient plus any additional desired ingredient from a previously sterile-filtered solution thereof.

In one embodiment, agent of the present technology is administered intravenously. For example, an agent of the present technology may be administered via rapid intravenous bolus injection. In some embodiments, the agent of the present technology is administered as a constant-rate intravenous infusion.

The agent of the present technology may also be administered orally, topically, intranasally, intramuscularly, subcutaneously, or transdermally. In one embodiment, transdermal administration is by iontophoresis, in which the charged composition is delivered across the skin by an electric current.

Other routes of administration include intracerebroventricularly or intrathecally. Intracerebroventricularly refers to administration into the ventricular system of the brain. Intrathecally refers to administration into the space under the arachnoid membrane of the spinal cord. Thus, in some embodiments, intracerebroventricular or intrathecal administration is used for those diseases and conditions which affect the organs or tissues of the central nervous system.

For systemic, intracerebroventricular, intrathecal, topical, intranasal, subcutaneous, or transdermal administration, formulations of the agents of the present technology may utilize conventional diluents, carriers, or excipients etc., such as those known in the art to deliver the agents of the present technology. For example, the formulations may comprise one or more of the following: a stabilizer, a surfactant, such as a nonionic surfactant, and optionally a salt and/or a buffering agent. The agents of the present technology may be delivered in the form of an aqueous solution, or in a lyophilized form.

VI. Dosage

The dosage ranges described herein are exemplary and are not intended to be limiting.

Dosage, toxicity, and therapeutic efficacy of the agents of the present technology can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any agent of the present technology used in the methods described herein, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Typically, an effective amount of the agent of the present technology, sufficient for achieving a therapeutic or prophylactic effect, ranges from about 0.000001 mg per kilogram body weight per day to about 10,000 mg per kilogram body weight per day. In some embodiments, the dosage ranges will be from about 0.0001 mg per kilogram body weight per day to about 100 mg per kilogram body weight per day. For example dosages can be 1 mg/kg body weight or 10 mg/kg body weight every day, every two days or every three days or within the range of 1-10 mg/kg every week, every two weeks or every three weeks. In one embodiment, a single dosage of the agent of the present technology ranges from 0.1-10,000 micrograms per kg body weight. An exemplary treatment regimen entails administration once per day or once a week. Intervals can also be irregular as indicated by measuring blood levels of glucose or insulin in the subject and adjusting dosage or administration accordingly. In some methods, dosage is adjusted to achieve a desired fasting glucose or fasting insulin concentration. In therapeutic applications, a relatively high dosage at relatively short intervals is sometimes required until progression of the disease is reduced or terminated, or until the subject shows partial or complete amelioration of symptoms of disease. Thereafter, the patient can be administered a prophylactic regimen.

In some embodiments, a therapeutically effective amount of the agent of the present technology is defined as a concentration of the agent of the present technology at the target tissue of $10^{-11}$ to $10^{-6}$ molar, e.g., approximately $10^{-7}$ molar. This concentration may be delivered by systemic doses of 0.01 to 100 mg/kg or equivalent dose by body surface area. The schedule of doses is optimized to maintain the therapeutic concentration at the target tissue, such as by single daily or weekly administration, but also including continuous administration (e.g., parenteral infusion or transdermal application).

The skilled artisan will appreciate that certain factors may influence the dosage and timing required to effectively treat a subject, including but not limited to, the severity of the disease or disorder, previous treatments, the general health and/or age of the subject, and the presence of other diseases. Moreover, treatment of a subject with a therapeutically effective amount of the therapeutic compositions described herein can include a single treatment or a series of treatments.

VII. Therapeutic Applications

The methods and compositions described herein have a variety of applications and therapeutic uses. In some embodiments, the methods and compositions disclosed herein are directed to the use of any one or more of the agents described in Section IV to stimulate gene transcription. In some embodiments, the present technology relates to methods and compositions for preventing or treating Friedreich's ataxia in a subject in need thereof. In some embodiments, the methods and compositions of the present technology increase the level of frataxin (FXN) mRNA levels in a cell. In some embodiments, the methods and compositions of the present technology increase frataxin protein levels in a cell. In some embodiments, the methods and compositions of the present technology prevent or treat one or more signs or symptoms of Friedreich's ataxia including, but not limited to, e.g., muscle weakness, loss of coordination, lack of reflexes in lower limbs, loss of ability to feel vibrations in lower limbs, vision impairment, color vision changes, involuntary eye movements, pes cavus, hearing impairment, slurred speech, scoliosis, diabetes, heart disorders (hypertrophic cardiomyopathy), elevated serum or plasma high sensitive troponin-T (hsTNT) (>14 ng/L), and reduced serum or plasma frataxin protein levels (≤19 ng/mL for pediatric and ≤21 ng/mL for adult patients). In some embodiments, the methods and compositions of the present technology reduce the likelihood that a subject with risk factors for Friedreich's ataxia will develop one or more signs or symptoms of Friedreich's ataxia, or will delay the onset of Friedreich's ataxia.

In some embodiments, the present technology relates to methods and compositions for preventing or treating Fragile X syndrome (FXS) in a subject in need thereof. In some embodiments, the methods and compositions of the present technology increase the level of Fragile X Mental Retardation 1 (FMR1) mRNA levels in a cell. In some embodiments, the methods and compositions of the present technology increase FMRP protein levels in a cell. In some embodiments, the methods and compositions of the present technology prevent or treat one or more signs or symptoms of Fragile X syndrome (FXS) including, but not limited to, e.g., intellectual disability, physical features in males include long face, soft skin, macroorchidism, ear infections, flat feet, high arched palate, double-jointed fingers, and hyper-flexible joints. Behavioral features may include ADD, ADHD, autism and autistic behaviors, autism spectrum disorder (ASD), social anxiety, hand-biting and/or flapping, poor eye contact, sensory disorders, seizures, Premature Ovarian Insufficiency (FXPOI), and increased aggression. In some embodiments, the methods and compositions of the present technology reduce the likelihood that a subject with risk factors for Fragile X syndrome (FXS) will develop one or more signs or symptoms of Fragile X syndrome (FXS), or will delay the onset of Fragile X syndrome (FXS).

In some embodiments, the present technology relates to methods and compositions for preventing or treating Fragile X-associated tremor/ataxia syndrome (FXTAS) in a subject in need thereof. In some embodiments, the methods and compositions of the present technology increase the level of Fragile X Mental Retardation 1 (FMR1) mRNA levels in a cell. In some embodiments, the methods and compositions of the present technology increase FMRP protein levels in a cell. In some embodiments, the methods and compositions of the present technology prevent or treat one or more signs or symptoms of Fragile X-associated tremor/ataxia syndrome (FXTAS) including, but not limited to, e.g., Parkinsonian tremor, ataxia, cognitive decline, mood disorders, abnormal MRI, and eosinophilic nuclear inclusions in neurons and glial cells that contain ubiquitin and various proteins involved in proteasome degradation. In some embodiments, the methods and compositions of the present technology reduce the likelihood that a subject with risk factors for Fragile X-associated tremor/ataxia syndrome (FXTAS) will develop one or more signs or symptoms of Fragile X-associated tremor/ataxia syndrome (FXTAS), or will delay the onset of Fragile X-associated tremor/ataxia syndrome (FXTAS).

In some embodiments, the present technology relates to methods and compositions for preventing or treating myotonic dystrophy type 1 (DM type 1) in a subject in need thereof. In some embodiments, the methods and compositions of the present technology increase the level of DMPK mRNA levels in a cell. In some embodiments, the methods and compositions of the present technology increase DMPK protein levels in a cell. In some embodiments, the methods and compositions of the present technology prevent or treat one or more signs or symptoms of myotonic dystrophy type 1 (DM type 1) including, but not limited to, e.g., myotonia (hyperexcitability of skeletal muscle or sustained muscle contraction), muscle wasting of skeletal, cardiac and smooth muscle, insulin resistance, defects in cardiac conduction, cataracts, cognitive dysfunction, central nervous system involvement, and mental retardation. In some embodiments, the methods and compositions of the present technology reduce the likelihood that a subject with risk factors for myotonic dystrophy type 1 (DM type 1) will develop one or more signs or symptoms of myotonic dystrophy type 1 (DM type 1), or will delay the onset of myotonic dystrophy type 1 (DM type 1).

In some embodiments, the present technology relates to methods and compositions for preventing or treating myotonic dystrophy type 2 (DM type 2) in a subject in need thereof. In some embodiments, the methods and compositions of the present technology increase the level of CNBP (ZNF9 or zinc finger 9) mRNA levels in a cell. In some embodiments, the methods and compositions of the present technology increase CNBP protein levels in a cell. In some embodiments, the methods and compositions of the present technology prevent or treat one or more signs or symptoms of myotonic dystrophy type 2 (DM type 2) including, but not limited to, e.g., myotonia (hyperexcitability of skeletal muscle or sustained muscle contraction), muscle wasting of skeletal, cardiac and smooth muscle, insulin resistance, defects in cardiac conduction, cataracts, cognitive dysfunction, and central nervous system involvement. In some embodiments, the methods and compositions of the present technology reduce the likelihood that a subject with risk factors for myotonic dystrophy type 2 (DM type 2) will develop one or more signs or symptoms of myotonic dystrophy type 2 (DM type 2), or will delay the onset of myotonic dystrophy type 2 (DM type 2).

In practicing the present technology, many conventional techniques in molecular biology, protein biochemistry, cell biology, immunology, microbiology, and recombinant DNA are used. These techniques are well-known and are explained in, e.g., *Current Protocols in Molecular Biology*, Vols. I-III, Ansubel, Ed. (1997); Sambrook et al., *Molecular Cloning: A Laboratory Manual*, Second Ed. (Cold Spring Harbor Laboratory Press, Cold Spring Harbor, N.Y., 1989); *DNA Cloning: A Practical Approach*, Vols. I and II, Glover, Ed. (1985); *Oligonucleotide Synthesis*, Gait, Ed. (1984); *Nucleic Acid Hybridization*, Hames & Higgins, Eds. (1985); *Transcription and Translation*, Hames & Higgins, Eds. (1984); *Animal Cell Culture*, Freshney, Ed. (1986); *Immo-* bilized *Cells and Enzymes* (IRL Press, 1986); Perbal, *A Practical Guide to Molecular Cloning*; the series, *Meth. Enzymol.*, (Academic Press, Inc., 1984); *Gene Transfer Vectors for Mammalian Cells*, Miller & Calos, Eds. (Cold Spring Harbor Laboratory, N Y, 1987); and *Meth. Enzymol.*, Vols. 154 and 155, Wu & Grossman, and Wu, Eds., respectively. Methods to detect and measure levels of polypeptide gene expression products (i.e., gene translation level) are well-known in the art and include the use polypeptide detection methods such as antibody detection and quantification techniques. (See also, Strachan & Read, *Human Molecular Genetics*, Second Edition. (John Wiley and Sons, Inc., NY, 1999)).

The definitions of certain terms as used in this specification are provided below. Unless defined otherwise, all technical and scientific terms used herein generally have the same meaning as commonly understood by one of ordinary skill in the art to which this present technology belongs.

As used in this specification and the appended claims, the singular forms "a", "an" and "the" include plural referents unless the content clearly dictates otherwise. For example, reference to "a cell" includes a combination of two or more cells, and the like.

As used herein, the term "about" indicates values that may deviate up to 1%, 5%, 10%, 15%, and in some cases up to 20% higher or lower than the value referred to, the deviation range including integer values, and, if applicable, non-integer values as well, constituting a continuous range.

As used herein, the "administration" of an agent to a subject includes any route of introducing or delivering to a subject a compound to perform its intended function. Administration can be carried out by any suitable route, including orally, intranasally, parenterally (intravenously, intramuscularly, intraperitoneally, or subcutaneously), intrathecally, topically, iontophoretically and the like. Administration includes self-administration and the administration by another.

The term "binds" refers to formation of a complex between two or more molecules to a statistically greater degree than would be expected for non-interacting molecules; complexes so formed may include covalent bonding or non-covalent bonding (e.g., hydrogen bonding) between two or more of the molecules of the complex. Methods for the detection of complexes involving DNA are well known in the art. Binding is characterized by a dissociation constant ($K_D$), well known in the art.

As used herein, "bromodomain" refers a portion of a polypeptide that recognizes acetylated lysine residues. In one embodiment, a bromodomain of a BET family member polypeptide comprises approximately 110 amino acids and shares a conserved fold comprising a left-handed bundle of four alpha helices linked by diverse loop regions that interact with chromatin.

By "BET family polypeptide" is meant a polypeptide comprising two bromodomains and an extraterminal (ET) domain or a fragment thereof having transcriptional regulatory activity or acetylated lysine binding activity. Exemplary BET family members include Brd2, Brd3, Brd4 and BrdT. Brd4 is a member of the BET family of bromodomain-containing proteins that bind to acetylated histones to influence transcription. As used herein, "Brd4 polypeptide" refers to a protein or fragment thereof having at least 85% identity to NP 055114 that is capable of binding chromatin or regulating transcription. The sequence (SEQ ID NO: 1) of the exemplary Brd4 polypeptide NP 055114 is shown below:

```
  1  msaesgpgtr lrnlpvmgdg letsqmsttq aqaqpqpana astnppppet snpnkpkrqt
 61  nqlqyllrv  lktlwkhqfa wpfqqpvdav klnlpdyyki iktpmdmgti kkrlennyyw
121  naqeciqdfn tmftncyiyn kpgddivlma ealeklflqk inelpteete imivqakgrg
181  rgrketgtak pgvstvpntt qastppqtqt pqpnppvqa  tphpfpavtp dlivqtpvmt
241  vppqplqtp  ppvppqpqpp papapqpvqs hppiiaatpq pvktkkgvkr kadtttptti
301  dpiheppslp pepkttklgq rressrpvkp pkkdvpdsqq hpapeksskv seqlkccsgi
361  lkemfakkha ayawpfykpv dvealglhdy cdiikhpmdm stiksklear eyrdaqefga
421  dvrlmfsncy kynppdhevv amarklqdvf emrfakmpde peepvvayss pavppptkvv
481  appsssdsss dsssdsdsst ddseeeraqr laelqeqlka vheqlaalsq pqqnkpkkke
541  kdkkekkkek hkrkeeveen kkskakeppp kktkknnssn snvskkepap mkskppptye
601  seeedkckpm syeekrqlsl dinklpgekl grvvhiiqsr epslknsnpd eieidfetlk
661  pstlrelery vtsclrkkrk pqaekvdvia gsskmkgfss sesesssess ssdsedsetg
```

As used herein, the term "Brd4 binding moiety" refers to compounds or subportion(s) of an agent that are capable of specifically binding a Brd4 polypeptide.

As used herein, a "control" is an alternative sample used in an experiment for comparison purpose. A control can be "positive" or "negative."

As used herein, the term "effective amount" refers to a quantity sufficient to achieve a desired therapeutic and/or prophylactic effect, e.g. an amount that reduces, ameliorates, or delays the onset of the physiological symptoms of Friedreich's ataxia. In the context of therapeutic or prophylactic applications, in some embodiments, the amount of a composition administered to the subject will depend on the type and severity of the disease and on the characteristics of the individual, such as general health, age, sex, body weight, and tolerance to drugs. In some embodiments, it will also depend on the degree, severity, and type of disease. The skilled artisan will be able to determine appropriate dosages depending on these and other factors. The compositions can also be administered in combination with one or more additional therapeutic compounds. In the methods described herein, agents having a formula A-L-B, wherein -L- is a linker; A- is a Brd4 binding moiety; and —B is a polyamide that specifically binds to one or more repeats of a GAA oligonucleotide sequence, or a pharmaceutically acceptable salts thereof, such as acetate or trifluoroacetate salts, may be administered to a subject having one or more signs, symptoms, or risk factors of Friedreich's ataxia, such as, e.g., ataxia, gait ataxia, muscle weakness, loss of coordination, loss of balance, lack of reflexes in lower limbs, loss of tendon reflexes, loss of ability to feel vibrations in lower limbs, loss of sensation in the extremities, loss of upper body strength, weakness in the arms, spasticity, loss of tactile sensation, impairment of position sense, impaired perception of light touch, impaired perception of pain, impaired perception of temperature, vision impairment, color vision changes, involuntary eye movements, pes cavus, inversion of the feet, hearing impairment, dysarthria, dysphagia, impaired breathing, scoliosis, diabetes, glucose intolerance, carbohydrate intolerance, hypertrophic cardiomyopathy, arrhythmia, myocardial fibrosis, cardiac failure, elevated serum or plasma high sensitive troponin-T (hsTNT) (>14 ng/L), and reduced serum or plasma frataxin protein levels (≤19 ng/mL for pediatric and ≤21 ng/mL for adult patients). For example, a "therapeutically effective amount" of agents having a formula A-L-B wherein -L- is a linker; A- is a Brd4 binding moiety; and —B is a polyamide that specifically binds to one or more repeats of a GAA oligonucleotide sequence includes levels at which the presence, frequency, or severity of one or more signs, symptoms, or risk factors of Friedreich's ataxia are reduced or eliminated. In some embodiments, a therapeutically effective amount reduces or ameliorates the physiological effects of Friedreich's ataxia, and/or the risk factors of Friedreich's ataxia, and/or delays the progression or onset of Friedreich's ataxia.

As used herein, the terms "expansion" and "repeat expansion" refer to the presence of contiguously repeated oligonucleotide sequences in a gene. The term "hyper-expansion" refers to a level of expansion greater than typically observed in a population. For example, whereas typical alleles may have an expansion of 6-34 repeats, a hyper-expanded allele may include from 66-1700 repeats, or even more.

As used herein, "expression" includes, but is not limited to one or more of the following: transcription of the gene into precursor mRNA; splicing and other processing of the precursor mRNA to produce mature mRNA; mRNA stability; translation of the mature mRNA into protein (including codon usage and tRNA availability); and glycosylation and/or other modifications of the translation product, if required for proper expression and function.

As used herein, the term "oligonucleotide sequence" refers to a plurality of nucleic acids having a defined sequence and length (e.g., 2, 3, 4, 5, 6, or even more nucleotides). Oligonucleotide sequences may be present, for example, within genomic nucleotide sequences. Oligonucleotide sequences may also be present, for example, within nucleotide sequences of genes. Oligonucleotide sequences may also be present, for example, within recombinant nucleotide sequences such as plasmids or vectors. The term "oligonucleotide repeat sequence" or "repeats of an oligonucleotide sequence" refers to a continguous expansion of oligonucleotide sequences. The terms "nucleic acid" and "nucleotide" refer to ribonucleotide and deoxyribonucleotide, and analogs thereof, well known in the art.

As used herein, the term "predisposed to having" Friedreich's ataxia refers to subjects with a family history of Friedreich's ataxia such that there is a possibility that the subject has inherited one or more genetic loci comprising disease loci and will at some point develop a diagnosable disorder. The term also encompasses subjects heterozygous or homozygous at a single disease locus or multiple disease loci.

As used herein, the term "predisposed to having" Fragile X syndrome (FXS) refers to subjects with a family history of Fragile X syndrome (FXS) such that there is a possibility that the subject has inherited one or more genetic loci comprising disease loci and will at some point develop a diagnosable disorder.

As used herein, the term "predisposed to having" Fragile X-associated tremor/ataxia syndrome (FXTAS) refers to subjects with a family history of Fragile X syndrome (FXS) and/or Fragile X-associated tremor/ataxia syndrome (FXTAS) such that there is a possibility that the subject has inherited one or more genetic loci comprising disease loci and will at some point develop a diagnosable disorder.

As used herein, the term "predisposed to having" myotonic dystrophy type 1 (DM type 1) refers to subjects with a family history of myotonic dystrophy type 1 (DM type 1) such that there is a possibility that the subject has inherited one or more genetic loci comprising disease loci and will at some point develop a diagnosable disorder.

As used herein, the term "predisposed to having" myotonic dystrophy type 2 (DM type 2) refers to subjects with a family history of myotonic dystrophy type 2 (DM type 2) such that there is a possibility that the subject has inherited one or more genetic loci comprising disease loci and will at some point develop a diagnosable disorder.

As used herein, "specifically binds" means a compound or agent that recognizes and binds a particular polypeptide, but which does not substantially recognize and bind other molecules in a sample, for example, a biological sample, which naturally includes the particular polypeptide.

The term "suspected of having" refers to subjects who present with clinical or biochemical symptoms associated with Friedreich's ataxia, regardless of whether they have been diagnosed as having the disorder.

As used herein, the term "subject" refers to an organism administered one or more compositions of the present technology. Typically, the subject is a mammal, such as an animal, e.g., domestic animals (e.g., dogs, cats and the like), farm animals (e.g., cows, sheep, pigs, horses and the like) and laboratory animals (e.g., monkey, rats, mice, rabbits, guinea pigs and the like). In some embodiments, the subject is a human.

The term "transcription," well known in the art, refers to the synthesis of RNA (i.e., ribonucleic acid) by DNA-directed RNA polymerase. The term "modulate transcription" and similar terms refer to a change in transcriptional level that can be measured by methods well known in the art, e.g., methods directed at the assay of mRNA, the product of transcription. In some embodiments, modulation is an increase in transcription. In other embodiments, modulation is a decrease in transcription.

As used herein, the term "transcriptional pausing-based genetic disease" results from a reduction in gene expression from the gene whose repression underlies the cause of the disease. At the genomic location of transcription of the gene, RNA polymerase II initiates transcription, but fails to elongate through the entire open reading frame to produce full-length pre-mRNA. Splicing is unaffected, allowing for the production of normal full-length protein, albeit at reduced levels.

As used herein, the terms "treat," treating," "treatment," and the like refer to preventing or ameliorating a disorder or condition and/or symptoms associated therewith. By "ameliorate" is meant decrease, suppress, attenuate, diminish, arrest, or stabilize the development or progression of a disease or condition. It will be appreciated that, although not precluded, treating a disorder or condition does not require that the disorder, condition or symptoms associated therewith be completely eliminated. As used herein, the terms "prevent," "preventing," "prevention," "prophylactic treatment" and the like refer to reducing the probability of developing a disorder or condition in a subject, who does not have, but is at risk of or susceptible to developing a disorder or condition.

As referred to herein, in the therapeutic treatment of Friedreich's ataxia, the object is typically to reduce, alleviate or slow down (lessen) the pathologic condition or disorder. By way of example, but not by way of limitation, a subject is successfully "treated" for Friedreich's ataxia if, after receiving a therapeutic amount of an agent having a formula A-L-B, wherein -L- is a linker; A- is a Brd4 binding moiety; and —B is a polyamide that specifically binds to one or more repeats of a GAA oligonucleotide sequence, or a pharmaceutically acceptable salt thereof, such as acetate or trifluoroacetate salt, according to the methods described herein, the subject shows observable and/or measurable reduction in or absence of one or more signs and symptoms of Friedreich's ataxia, such as but not limited to, e.g., ataxia, gait ataxia, muscle weakness, loss of coordination, loss of balance, lack of reflexes in lower limbs, loss of tendon reflexes, loss of ability to feel vibrations in lower limbs, loss of sensation in the extremities, loss of upper body strength, weakness in the arms, spasticity, loss of tactile sensation, impairment of position sense, impaired perception of light touch, impaired perception of pain, impaired perception of temperature, vision impairment, color vision changes, involuntary eye movements, pes cavus, inversion of the feet, hearing impairment, dysarthria, dysphagia, impaired breathing, scoliosis, diabetes, glucose intolerance, carbohydrate intolerance, hypertrophic cardiomyopathy, arrhythmia, myocardial fibrosis, cardiac failure, elevated serum or plasma high sensitive troponin-T (hsTNT) (>14 ng/L), and reduced serum or plasma frataxin levels (≤19 ng/mL for pediatric and ≤21 ng/mL for adult patients). It is also to be appreciated that the various modes of treatment of medical conditions as described are intended to mean "substantial," which includes total but also less than total treatment, and wherein some biologically or medically relevant result is achieved. Treating Friedreich's ataxia, as used herein, also refers to treating the signs and symptoms related to reduced frataxin activity or frataxin expression levels characteristic of Friedreich's ataxia. For example, treating Friedreich's ataxia may refer to increasing frataxin mRNA levels in a patient having Friedreich's ataxia relative to the patient prior to treatment. Treating Friedreich's ataxia may also refer to increasing frataxin protein levels in a patient having Friedreich's ataxia relative to the patient prior to treatment.

As used herein, Friedreich's ataxia (FA or FRDA) refers to a disease or condition such that a subject has reduced levels of frataxin relative to an unaffected subject or a healthy carrier having a Friedreich's ataxia (FRDA)-associated allele and where the subject has at least about 50 GAA trinucleotide repeats in the frataxin (FXN) gene.

As used herein, a "triplet repeat" or "trinucleotide repeat" refers to a polymeric form of deoxyribonucleic acid (DNA) comprising a sequence unit that is three nucleotides in length such that each sequence unit is multiply repeated in a contiguous region in a gene. For example, a "triplet repeat" or "trinucleotide repeat" includes GAA trinucleotide repeats that may be found in the frataxin gene.

Generally, reference to a certain element such as hydrogen or H is meant to include all isotopes of that element. For example, if an R group is defined to include hydrogen or H, it also includes deuterium and tritium. Compounds comprising radioisotopes such as tritium, $C^{14}$, $P^{32}$ and $S^{35}$ are thus within the scope of the present technology. Procedures for inserting such labels into the compounds of the present technology will be readily apparent to those skilled in the art based on the disclosure herein.

In general, "substituted" refers to an organic group as defined below (e.g., an alkyl, cycloalkyl, and aryl groups) in which one or more bonds to a hydrogen atom contained therein are replaced by a bond to non-hydrogen atoms. Substituted groups also include groups in which one or more bonds to a carbon(s) or hydrogen(s) atom are replaced by one or more bonds, including double or triple bonds, to a heteroatom. Thus, a substituted group may be substituted with one or more substituents, unless otherwise specified. Examples of substituent groups include: halogens (i.e., F, Cl, Br, and I); alkyl, alkenyl, alkynyl, cycloalkyl, aryl, heteroaryl; hydroxyls; alkoxy, alkenoxy, aryloxy, cycloalkyloxy, aralkyloxy, heterocyclyl, heterocyclylalkyl, heterocyclyloxy, and heterocyclylalkoxy groups; carbonyls (oxo); carboxylates; esters; urethanes; oximes; hydroxylamines; alkoxyamines; aralkoxyamines; thiols; sulfides; sulfoxides; sulfones; sulfonyls; pentafluorosulfanyl (i.e., $SF_5$), sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like. Alkyl, cycloalkyl, cycloalkylalkyl, alkenyl, alkynyl, aryl, aralkyl, heterocyclyl, heteroaralkyl, alkoxy, amido, and amino groups may all be substituted one or more times with non-hydrogen groups. If possible, groups may be substituted at the alkyl, cycloalkyl, aryl, heterocyclyl, and/or heteroaryl group(s) of the group.

Alkyl groups include straight chain and branched chain alkyl groups having from 1 to 12 carbon atoms, and typically from 1 to 10 carbons or, in some embodiments, from 1 to 8, 1 to 6, or 1 to 4 carbon atoms. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. Exemplary substituted alkyl groups include, but are not limited to, halogenated alkyl (e.g., trifluoromethyl), hydroxyalkyl, thioalkyl, aminoalkyl, alkylaminoalkyl, dialkylaminoalkyl, alkoxyalkyl, carboxyalkyl, and the like.

Cycloalkyl groups include mono-, bi- or tricyclic alkyl groups having from 3 to 12 carbon atoms in the ring(s), or, in some embodiments, 3 to 10, 3 to 8, or 3 to 4, 5, or 6 carbon atoms. Exemplary monocyclic cycloalkyl groups include, but are not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Bi- and tricyclic ring systems include both bridged cycloalkyl groups and fused rings.

Cycloalkylalkyl groups are alkyl groups as defined above in which a hydrogen or carbon bond of an alkyl group is replaced with a bond to a cycloalkyl group as defined above. In some embodiments, cycloalkylalkyl groups have from 4 to 16 carbon atoms, 4 to 12 carbon atoms, and typically 4 to 10 carbon atoms.

Alkenyl groups include straight and branched chain alkyl groups as defined above, except that at least one double bond exists between two carbon atoms. Alkenyl groups may have from 2 to 12 carbon atoms, and typically from 2 to 10 carbons or, in some embodiments, from 2 to 8, 2 to 6, or 2 to 4 carbon atoms. In some embodiments, the alkenyl group has one, two, or three carbon-carbon double bonds.

Alkynyl groups include straight and branched chain alkyl groups as defined above, except that at least one triple bond exists between two carbon atoms. Alkynyl groups have from 2 to 12 carbon atoms, and typically from 2 to 10 carbons or, in some embodiments, from 2 to 8, 2 to 6, or 2 to 4 carbon atoms. In some embodiments, the alkynyl group has one, two, or three carbon-carbon triple bonds.

Aryl groups are cyclic aromatic hydrocarbons that do not contain heteroatoms. Aryl groups herein include monocyclic, bicyclic and tricyclic ring systems. Thus, aryl groups include, but are not limited to, phenyl, azulenyl, heptalenyl, biphenyl, fluorenyl, phenanthrenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. In some embodiments, the aryl groups are phenyl or naphthyl.

Aralkyl groups are alkyl groups as defined above in which a hydrogen or carbon bond of an alkyl group is replaced with a bond to an aryl group as defined above. In some embodiments, aralkyl groups contain 7 to 16 carbon atoms, 7 to 14 carbon atoms, or 7 to 10 carbon atoms. Exemplary aralkyl groups include, but are not limited to, benzyl and phenethyl groups.

Heterocyclyl groups include aromatic (also referred to as heteroaryl) and non-aromatic (also referred to as heterocycloalkyl or heterocyclylalkyl) ring compounds containing 3 or more ring members, of which one or more is a heteroatom such as, but not limited to, N, O, and S. In some embodiments, the heterocyclyl group contains 1, 2, 3 or 4 heteroatoms. In some embodiments, heterocyclyl groups include mono-, bi- and tricyclic rings having 3 to 16 ring members. Heterocyclyl groups encompass aromatic, partially unsaturated and saturated ring systems, such as, for example, imidazolyl, imidazolinyl and imidazolidinyl groups. The phrase "heterocyclyl group" includes fused ring species including those comprising fused aromatic and non-aromatic groups. However, the phrase does not include heterocyclyl groups that have other groups, such as alkyl, oxo or halo groups, bonded to one of the ring members. Rather, these are referred to as "substituted heterocyclyl groups". Heterocyclyl groups include, but are not limited to, aziridinyl, azetidinyl, pyrrolidinyl, imidazolidinyl, pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, thiazolyl, thiazolinyl, isothiazolyl, thiadiazolyl, oxadiazolyl, piperidyl, piperazinyl, morpholinyl, thiomorpholinyl, tetrahydropyranyl, tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolyl, azaindolyl (pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, pyrazolopyridyl, imidazopyridyl (azabenzimidazolyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, tetrahydroquinolinyl, 1,2-diazepanyl, 1,3-diazepanyl, and 1,4-diazepanyl groups. Exemplary heterocyclyl group include, but are not limited to, pyridyl and thiazolyl groups.

Heteroaralkyl groups are alkyl groups as defined above in which a hydrogen or carbon bond of an alkyl group is replaced with a bond to a heteroaryl group as defined above.

Heteroatom as used herein refers to an atom of any element other than carbon or hydrogen. Exemplary heteroatoms include, but are not limited to, nitrogen, oxygen, sulfur, and phosphorus.

Groups described herein having two or more points of attachment (i.e., divalent, trivalent, or polyvalent) within the compound of the present technology are designated by use of the suffix, "ene." For example, divalent alkyl groups are alkylene groups, divalent aryl groups are arylene groups, divalent heteroaryl groups are divalent heteroarylene groups, and so forth.

Alkoxy groups are hydroxyl groups (—OH) in which the bond to the hydrogen atom is replaced by a bond to a carbon atom of an alkyl group as defined above. Examples of linear alkoxy groups include but are not limited to methoxy, ethoxy, propoxy, butoxy, pentoxy, hexoxy, and the like. Alkoxyalkyl groups are alkoxy groups in which the oxygen is bonded to both an alkyl group and an alkylene group.

The term "amide" (or "amido") includes C- and N-amide groups, i.e., —C(O)NR$^{71}$R$^{72}$, and —NR$^{71}$C(O)R$^{72}$ groups, respectively. R$^{71}$ and R$^{72}$ are independently hydrogen, or a substituted or unsubstituted alkyl, alkenyl, alkynyl, cycloalkyl, aryl, aralkyl, heterocyclylalkyl or heterocyclyl group as defined herein.

The term "nitrile" or "cyano" as used herein refers to the —CN group.

The term "amine" (or "amino") as used herein refers to —NR$^{75}$R$^{76}$ groups, wherein R$^{75}$ and R$^{76}$ are independently hydrogen, or a substituted or unsubstituted alkyl, alkenyl, alkynyl, cycloalkyl, aryl, aralkyl, heterocyclylalkyl or heterocyclyl group as defined herein. In some embodiments, the amine may be alkylamino, dialkylamino, arylamino, or alkylarylamino. In some embodiments, the amino group may be positively charged (e.g., —NH$_3^+$).

The term "halogen" or "halo" as used herein refers to bromine, chlorine, fluorine, or iodine. In some embodiments, the halogen is fluorine. In other embodiments, the halogen is chlorine or bromine.

The term "halogenated alkyl" or "haloalkyl" as used herein refers to alkyl groups as defined above that are mono-, di-, or polysubstituted by halogen. Exemplary halogenated alkyl groups include, but are not limited to, fluoromethyl and trifluoromethyl.

EXAMPLES

The present technology is further illustrated by the following examples, which should not be construed as limiting in any way.

Unless otherwise noted, starting materials were purchased from standard chemical suppliers and used without further purification. Water was purified with a NANOPURE® water purification system (18.2 MΩ). All buffers were filtered (0.2

μm) before use. Oligonucleotide oligomers were purchased from Integrated DNA Technologies Inc. Cell culture media and reagents were purchased from Invitrogen.

Example 1: Synthesis of Subunit —B Polyamide

Polyamide 1 (see Polyamide 1 formula below) and polyamide 3 (see Polyamide 3 formula below) were synthesized by manual solid-phase synthesis using Boc-beta-alanine PAM resin following established procedures (Boc=tert-butoxycarbonyl) in Baird, E. E. et al., *J. Am. Chem. Soc.* 118, 6141-6146 (1996), which is incorporated herein by reference. After synthesis was complete, the polyamides were cleaved from the support by aminolysis with 3,3'-diamino-N-methyldipropylamine (55° C., 12 h). The polyamides were precipitated twice with diethyl ether, dissolved in 15% acetonitrile/$H_2O$+0.1% trifluoroacetic acid (TFA), and purified by reverse-phase preparative HPLC on a $C_{18}$ column. The clean polyamide fractions were frozen and lyophilized to afford a white or off-white powder. The quantity of each polyamide was measured by UV/Vis spectroscopy with a molar extinction coefficient of 8650 $M^{-1}$ $cm^{-1}$ at a $\lambda_{max}$ near 310 nm for each N-methylpyrrole, N-methylimidazole, or 3-chlorothiophene.

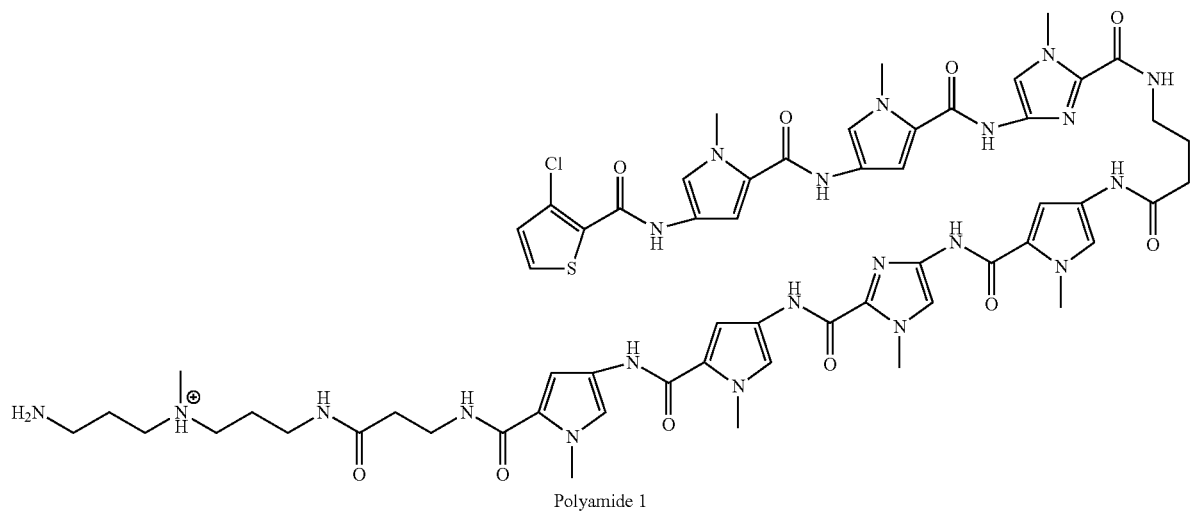

Polyamide 1

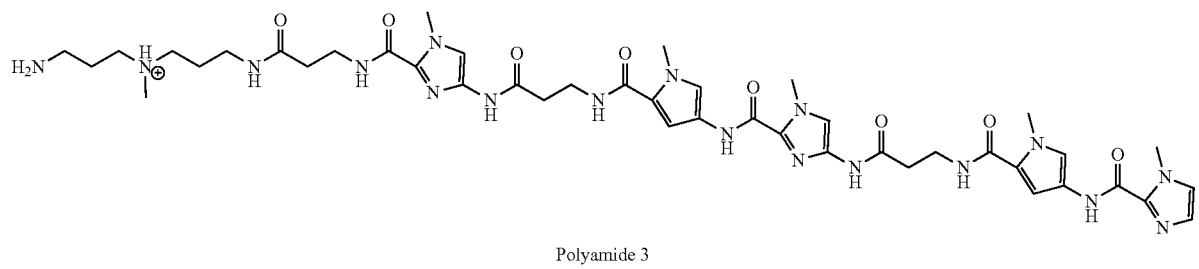

Polyamide 3

Table 3 illustrates the identity and purity of control polyamides 1 and 3 using MALDI-TOF mass spectrometry and analytical HPLC.

TABLE 3

Mass spectrometric of polyamides 1 and 3.

| Molecule | Molecular formula | Mass Calculated | Mass Observed |
| --- | --- | --- | --- |
| Control polyamide 1 | $C_{59}H_{73}ClN_{21}O_{10}S$ | 1302.53 | 1303.14 |
| Control polyamide 3 | $C_{43}H_{61}N_{18}O_8$ | 957.49 | 958.11 |

Example 2: Synthesis of A-L-B Agent

Figure 16:
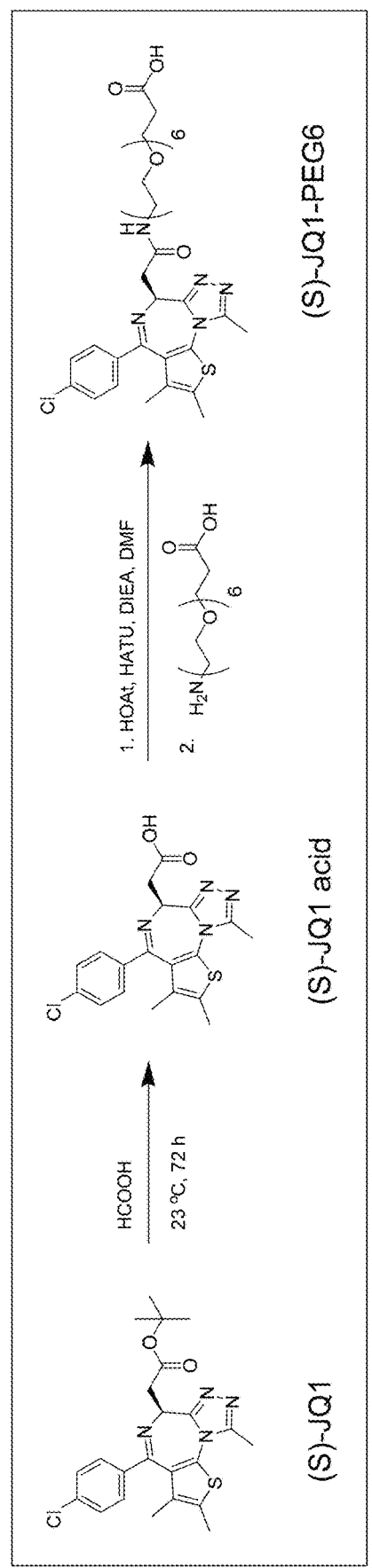
FIG. 16 shows Scheme 5 which shows coupling of subunit A- and linker -L-.

Exemplary subunit A-, (S)-JQ1, was synthesized as previously described in Filippakopoulos, P. et al., *Nature* 468, 1067-1073 (2010), which is incorporated herein by reference. As shown in Scheme 5 (FIG. 16), following the synthesis of (S)-JQ1, the tert-butyl group was hydrolyzed with formic acid (23° C., 72 h) to afford (S)-JQ1 acid. The JQ1 acid was then activated using HOAt (1-Hydroxy-7-azabenzotriazole) and HATU (1-[Bis(dimethylamino)methylene]-1H-1,2,3-triazolo[4,5-b]pyridinium 3-oxid hexafluorophosphate), then coupled to linker $H_2N$-PEG6-$CH_2CH_2COOH$ (23° C., 4 h) to afford (S)-JQ1-PEG6. The resulting molecule was purified by reverse-phase HPLC and verified by MALDI-TOF mass spectrometry. Fractions that showed clean molecule were frozen and lyophilized to afford an oil.

Table 4 illustrates the identity and purity of (S)-JQ1-PEG6 using MALDI-TOF mass spectrometry and analytical HPLC.

TABLE 4

Mass spectrometric of (S)-JQ1-PEG6.

| Molecule | Molecular formula | Mass Calculated | Mass Observed |
|---|---|---|---|
| (S)-JQ1-PEG6 | $C_{34}H_{47}ClN_5O_9S^+$ | 736.28 | 736.95 |

Figure 17:
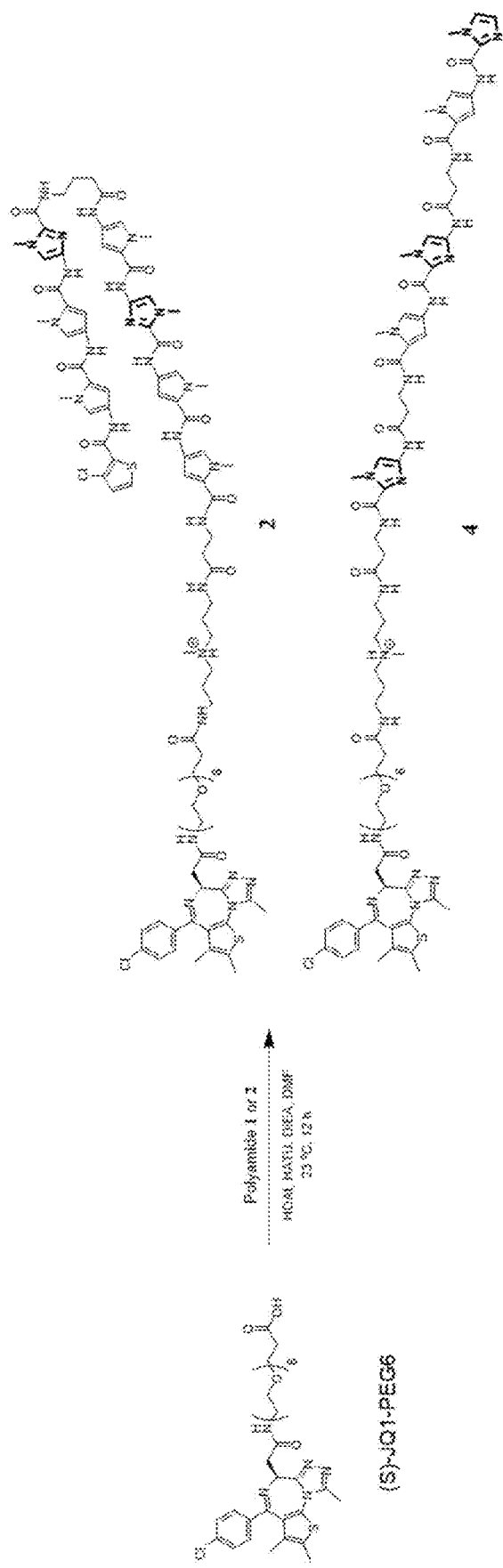
FIG. 17 shows Scheme 6 which shows coupling of subunit A-L- and subunit —B.

As shown in Scheme 6 (FIG. 17), (S)-JQ1-PEG6 was activated with HOAt and HATU in N,N-diisopropyethylamine (DIEA) and dimethylformamide (DMF), then coupled to control polyamides 1 or 3 to yield the control polyamide 1-PEG6-JQ1 (control conjugate 1) and control polyamide 3-PEG6-JQ1 (Agent 4), respectively. The conjugates were purified by reverse-phase HPLC and analyzed by MALDI-TOF mass spectrometry (Table 5). Fractions that showed clean conjugate without contaminants were frozen in liquid nitrogen and lyophilized to afford a white or off white powder.

Table 5 illustrates the identity and purity of control conjugate 2 and Agent 4 using MALDI-TOF mass spectrometry and analytical HPLC.

TABLE 5

Mass spectrometric of control conjugate 2 and Agent 4.

| Molecule | Molecular formula | Mass Calculated | Mass Observed |
|---|---|---|---|
| Control conjugate 2 | $C_{93}H_{117}Cl_2N_{26}O_{18}S_2$ | 2019.79 | 2020.27 |
| Agent 4 | $C_{77}H_{105}ClN_{23}O_{16}S$ | 1674.75 | 1675.32 |

Example 3: Agents of the Present Technology Increase Frataxin Levels in FRDA Patient Cells A. Cell Culture GM15850 and GM15851 cell lines (Epstein Barr virus transformed human B-lymphocytes) were obtained from the National Institute of General Medical Sciences (NIGMS) Human Genetic Cell Repository at the Coriell Institute for Medical Research, Camden, N.J. The GM15850 cell line was derived from a clinically affected 13 year old Friedreich's ataxia patient ataxia displaying scoliosis, hypertrophic cardiomyopathy, and slurred speech, and characterized as homozygous for the GAA expansion in the frataxin gene with alleles of approximately 650 and 1030 repeats. The GM15851 cell line was derived from a clinically unaffected individual having two FRDA alleles in the normal range of GAA trinucleotide repeats (from about 6 to about 34 repeats). This clinically unaffected individual is a brother of the clinically affected patient from which the GM15850 cell line was derived.

Cells were maintained in RPMI 1640 supplemented with 2 mM L-glutamine and 15% fetal bovine serum (FBS) at 37° C. in a humidified atmosphere of 5% $CO_2$. Cell density was maintained between 200,000 cells/mL and 1,000,000 cells/mL. Cell growth and morphology were monitored by phase contrast microscopy and cell viability by trypan blue exclusion. To maintain cell density, cells were passaged by centrifuging at 500 g for 3 minutes and resuspending the cells in fresh media. To avoid cross-contamination, cells were handled separately with separate bottles of media. Relevant data were obtained from cell lines passaged between P9 and P12.

B. RT-PCR

To prepare agents for treatment of cells, each agent or agent mixture tested was dissolved in DMSO. The final concentration of DMSO was 0.1% except where JQ1 and Polyamide 3 combined were added to the same cells. For that treatment (JQ1+3), the final concentration of DMSO was 0.2%. 500,000 cells ells were seeded at 500,000 cells/mL and treated 24 h with agents in DMSO (0.1-0.2% DMSO final concentration). For the 24 hour treatment, cell media was changed immediately before treatment with agent and agent was added at the zero time point. The media was not changed during the 24 hour treatment time period.

After treatment with the agents or agent mixtures, cells were harvested and total RNA was purified with the RNeasy Mini Kit (Qiagen, Valencia, Calif.), including on-column DNase I treatment (ZYMO Research, Catalog number E1010), according to manufacturer's directions. The optional drying step, according to the manufacturer's instructions, was performed prior to elution of the purified RNA, and the RNeasy spin column was placed in a new collection tube and centrifuged at full speed for 1 min to remove residual buffers. cDNA was synthesized from 250 ng purified RNA via the iScript cDNA synthesis kit according to manufacturer's instructions (Bio-Rad, Hercules, Calif.). qPCR was performed with iTaq Universal SYBR Green Supermix (Bio-Rad) on a CFX Connect 96 instrument (Bio-Rad). cDNA was analyzed with PCR parameters as follows: 1 cycle of 95° C. 2 min and 40 cycles of 95° C. 5 s, 54° C. 30 s. Primer pairs for TATA-box binding protein (TBP) and FXN were used. The following primers were used for TBP: 5'-CCACTCACAGACTCTCACAAC-3' (forward) (SEQ ID NO:16) and 5'-CTGCGGTA-CAATCCCAGAACT-3' (reverse) (SEQ ID NO:17). The following primers for FXN were: 5'-AGCCAGAT-TTGCTTGTTTGG-3' (forward) (SEQ ID NO:18) and 5'-CAGAGGAAACGCTGGACTCT-3' (reverse) (SEQ ID NO:19). The following primers were used for BRWD1: 5'-CCAGCGCATCGGTCCTAT-3' (forward) (SEQ ID NO:20) and 5'-CTTCCTGCACCAAGTAAAGAAGT-3' (reverse) (SEQ ID NO:21). Expression was normalized to TBP. Error bars represent standard error of the mean for n=4 biological replicates.

C. Results

Figure 1B:
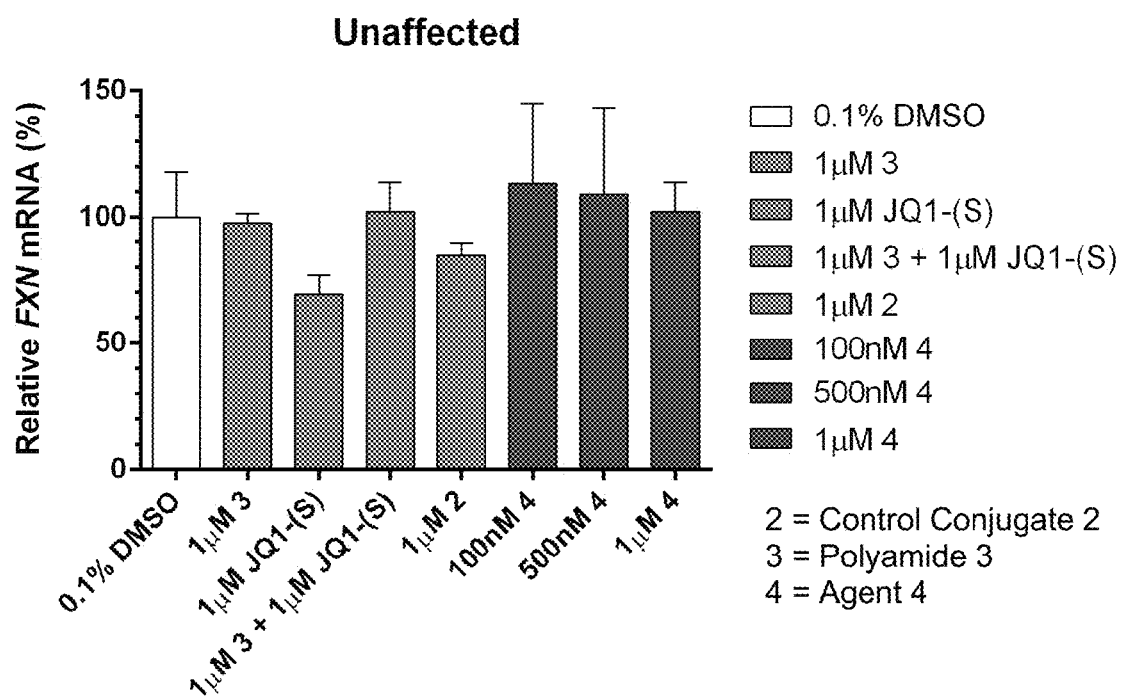
Figure 1C:
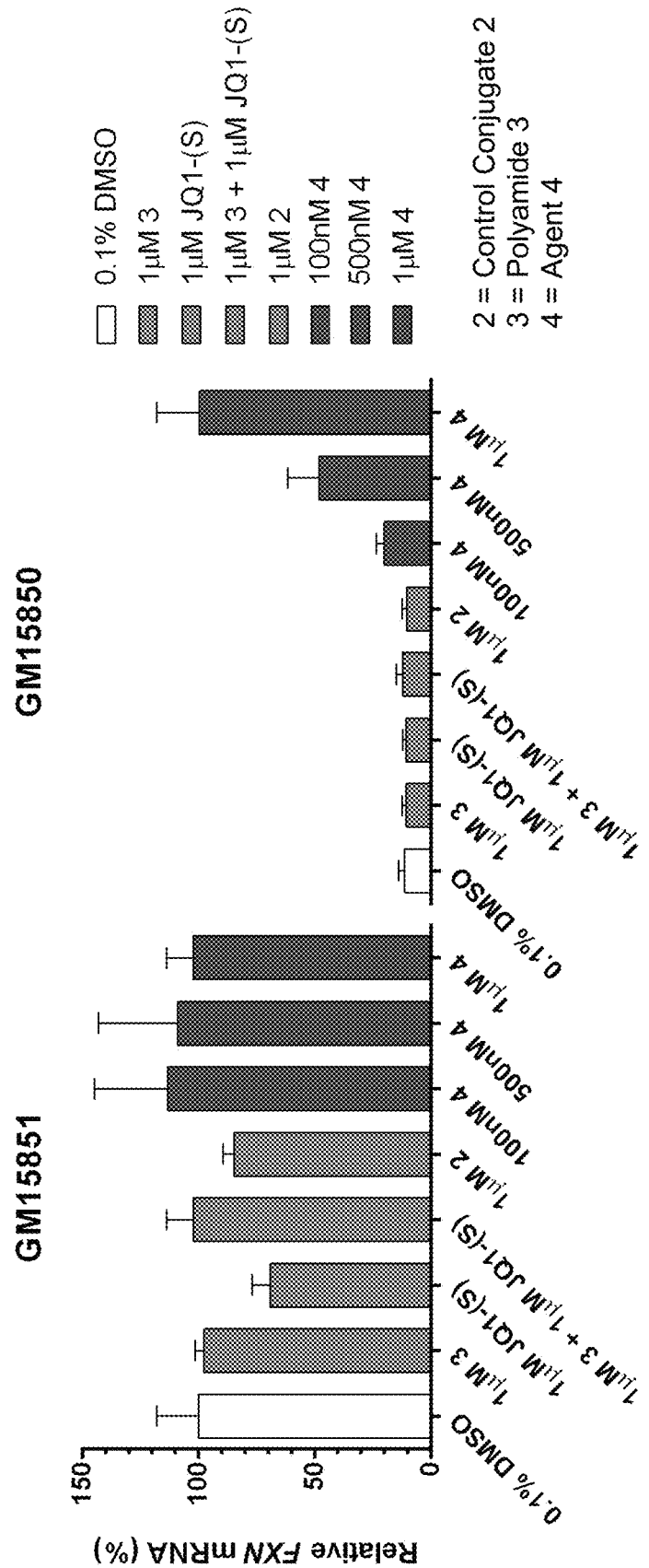

Agent 4 increases frataxin (FXN) mRNA levels in a cell line derived from a patient with Friedreich's ataxia (FRDA). As shown in FIG. 1A, frataxin (FXN) mRNA was measured by RT-PCR, relative to that of TATAA-box binding protein (TBP) mRNA, in a cell line derived from a patient with Friedreich's ataxia (GM15850). 24 hour treatment of FRDA patient cells (GM15850) with 0.1% DMSO served as a control. Additional control treatments for 24 hours with 0.1% DMSO, 1 µM Polyamide 3, 1 µM unconjugated JQ1, 1 µM Polyamide 3 and 1 µM unconjugated JQ1 (combination treatment), or 1 µM Control Conjugate 2 resulted in no increase in FXN mRNA levels. Treatment for 24 hours with 100 nM Agent 4 resulted in a slight (1.77-fold) increase in FXN mRNA levels. Treatment for 24 hours with 500 nM Agent 4 resulted in a 4.2-fold increase in FXN mRNA levels. Surprisingly, treatment for 24 hours with 1 µM Agent 4 resulted in an 8.5-fold increase in FXN mRNA levels. A 3-fold increase in FXN mRNA levels was observed after 6 hours treatment with 1 µM Agent 4 (data not shown). As shown in FIG. 1B, no changes in FXN mRNA levels were observed when treatment was performed using the GM15851 clinically unaffected cell line. As expected, the GM15850 FRDA patient cell line had a lower level of FXN mRNA compared to the GM15851 clinically unaffected cell line.

Example 4: Luciferase Reporter Assay

Figure 2:
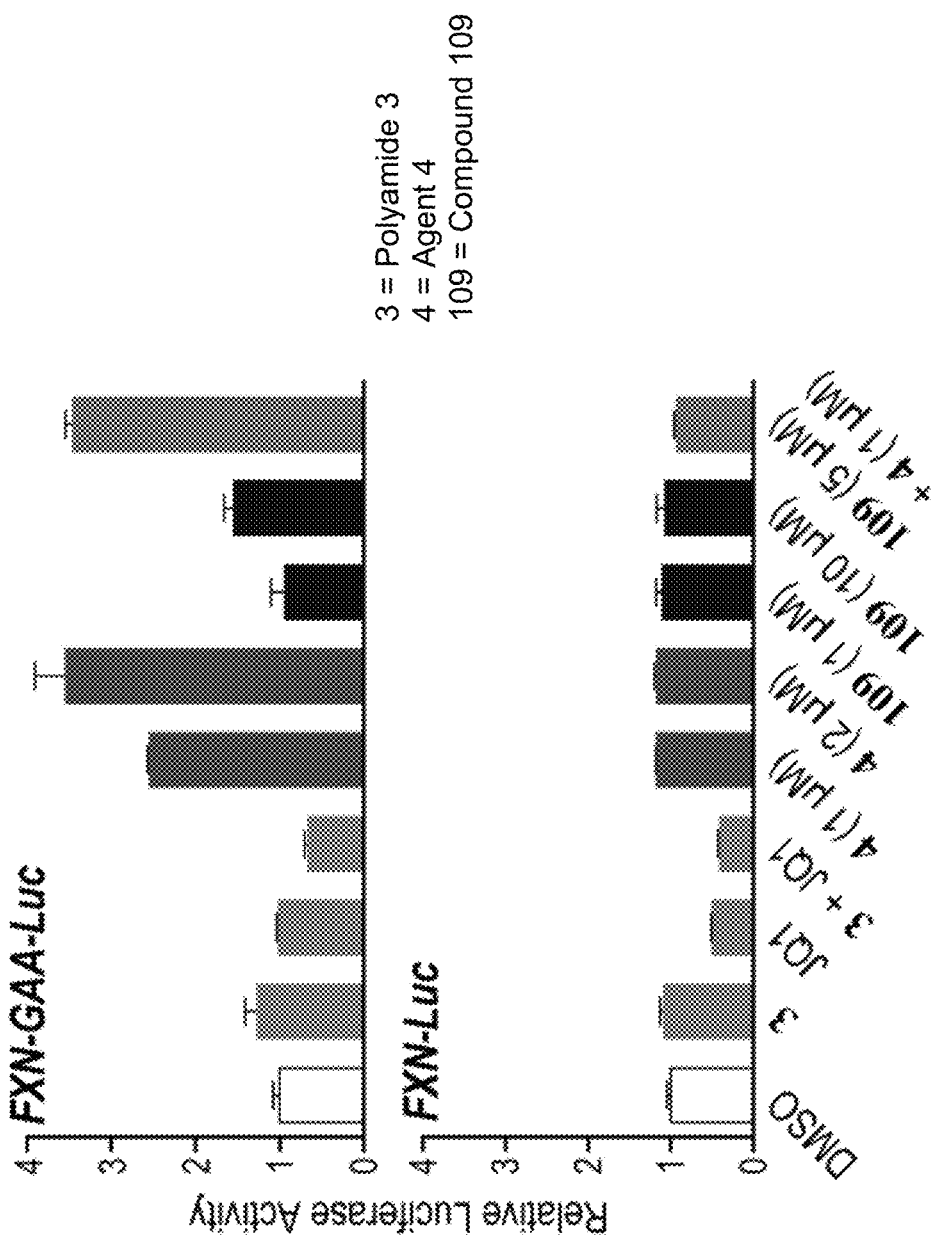
FIG. 2 is a bar graph showing luciferase activity of treated reporter cell lines FXN-Luc and FXN-GAA-Luc treated with Agent 4 and various controls, including Polyamide 3 ("3"), JQ1, and Compound 109.

The cellular consequence of Agent 4 on frataxin (FXN) expression was examined using a luciferase reporter assay. The luciferase reporter assay is described in Lufino et al., *Hum. Mol. Genet.*, 22(25): 5173-5187 (2013), the disclosure of which is herein incorporated by reference. This reporter, which includes a ~310 GAA repeat, recapitulates both the transcriptional repression and the heterochromatin formation at the endogenous FXN locus that are hallmarks of the FRDA disease. After 24 hours of treatment with Agent 4 (at 1 or 2 or control treatments (Control Conjugate 2 ("2"), Polyamide 3 ("3") or JQ1), cells were harvested and luciferase activity was measured. FIG. 2 shows a bar graph of luciferase activity for treated reporter cell lines FXN-Luc and FXN-GAA-Luc. The FXN-GAA-Luc line, containing ~310 GAA repeats in the first intron of FXN, was treated for 24 hours with the indicated molecules. Treatments are 2 µM unless otherwise indicated. Results are mean±SEM (n=4). The FXN-Luc line, containing 6 GAA repeats, was treated with the same conditions as for the FXN-GAA-Luc line.

A dose-dependent increase in luciferase activity was observed after treatment with Agent 4, exceeding the activity of Compound 109, a histone deacetylase inhibitor that recently completed a Phase Ib clinical trial for the treatment of Friedreich's ataxia (see Jacoby, D. et al., (PL1.003) *Neurology*, 82 (2014). The chemical structure of Compound 109 is shown below.

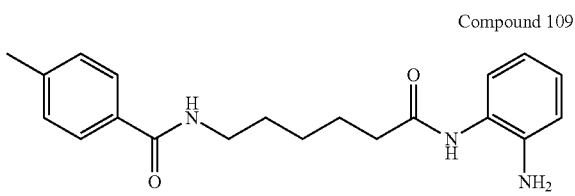 [SMILES: Cc1ccc(C(=O)NCCCCCC(=O)Nc2ccccc2N)cc1]

Compound 109

Significant activation was not observed for any of the control treatments, including treatment with Polyamide 3, JQ1, and the unconjugated combination of Polyamide 3 and JQ1. As an orthogonal test of specificity, we profiled the same compounds in a reporter cell line with just 6 GAA repeats in the first intron of FXN. Neither Agent 4, nor any of the controls, increased luciferase activity in the control line, confirming that the mechanism of action for Agent 4 is dependent on the GAA-repeat expansion (See FIG. 2). These results confirm that a polyamide-JQ1 conjugate can induce a robust increase of frataxin expression.

Methods

Cells containing FXN-Luc or FXN-GAA-Luc were seeded onto 24-well plates at a confluency of 20%. The next day, media was refreshed and cells were treated 24 hours with the indicated compound at the indicated concentration. Next, cell lysates were harvested and analyzed with the Luciferase Assay System (Promega, Madison, Wis.) per manufacturer's directions on a Synergy $H_4$ Hybrid Reader (BioTek, Winooski, Vt.).

Example 5: Immunoblot Assay

To assess the effects of treatment with a polyamide-JQ1 conjugate (e.g., Agent 4) on FXN protein, endogenous FXN levels were measured by immunoblot. After 24 hours of treatment, a dose-dependent increase in FXN protein was observed in GM15850 cells treated with Agent 4 (FIG. 3A). Neither polyamide alone (3), nor JQ1, nor the unconjugated treatment induced increased production of FXN protein. Furthermore, we did not detect overt increase in FXN protein in the unaffected GM15851 cells treated with Agent 4, consistent with this molecule targeting GAA repeats (FIG. 3B).

Figure 3B:
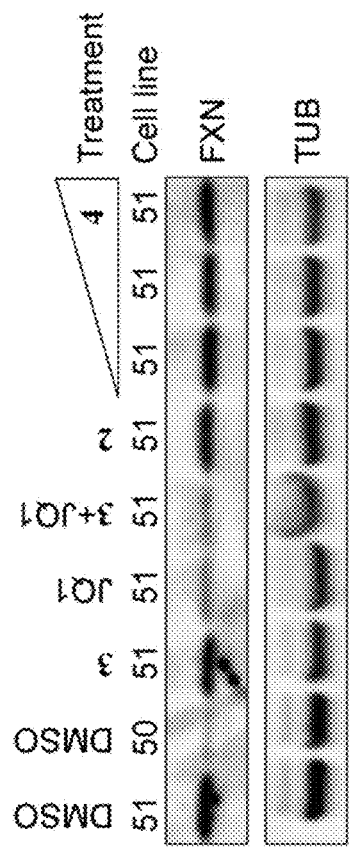
FIGS. 3A-3B show immunoblots for FXN and α-tubulin (TUB) in GM15850 cells (FIG. 3A) or GM15851 cells (FIG. 3B) treated with varying concentrations of Control Conjugate 2 ("2"), Polyamide 3 ("3"), JQ1, or Agent 4 ("4").
Figure 3A:
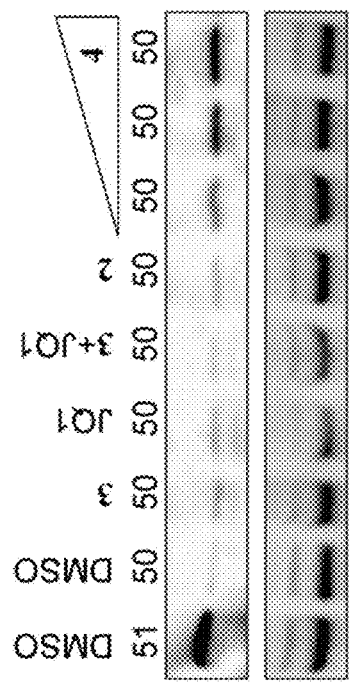
Figure 5:
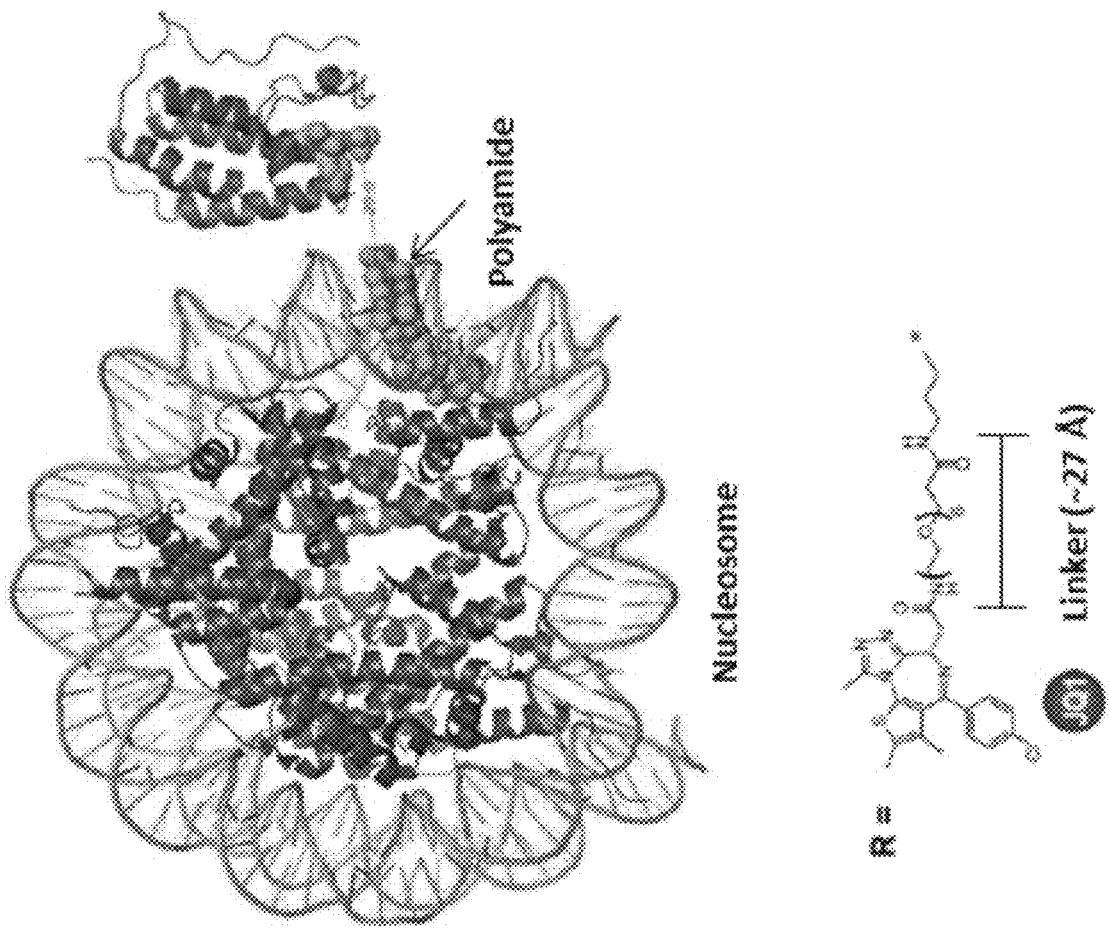
FIG. 5 is an image of a PyMOL structure modeling the design of the linker of the present technology (PEG6). The PyMOL structure shows a polyamide bound to a nucleosome and JQ1-(S) bound to Brd4. The minimal distance between these structures is measured and the length of the linker is shown. Two different .pdb files were opened in the same window and brought together to illustrate the importance of -L in the design of the full molecule.

FIG. 3 shows immunoblots for FXN and α-tubulin (TUB) in GM15850 cells (FIG. 3A) or GM15851 cells (FIG. 3B) treated with varying concentrations of Control Conjugate 2 ("2"), Polyamide 3 ("3"), JQ1 or Agent 4 ("4"). In FIG. 3A, "50" refers to GM15850 cells and in FIG. 3B, "51" refers to GM15851 cells. Cells were treated as in Example 4. All treatments are 24 hours in duration with 1 µM of the indicated molecule, except DMSO (0.1%) and Agent 4 (0.1, 0.5, or 1 µM). The results confirm an increase in FXN protein after treatment of GM15850 cells with Agent 4 and treatment of GM15851 cells with Agent 4 or Control Conjugate 2.

Methods

Total cell extracts from cell lines were used for immunoblot analysis. Antibodies to frataxin (abcam ab110328, 1:250 dilution) or alpha-Tubulin (Cell Signaling Technologies 2144, 1:1000 dilution) were used. Signal was detected by chemiluminescence with HRP-conjugated secondary antibodies (Bio-Rad 172-1011, 1:2000 for anti-mouse frataxin and GE NA934V, 1:2000 for anti-rabbit alpha-Tubulin).

Example 6: mRNA Levels Measure Viability

To assess the effects of treatment with the compositions of the present technology on cell viability, RNA concentrations of GM15850 cells were measured after 24 hours of treatment with each molecule (Control conjugate 2 ("2"), unconjugated JQ1-(S), Control polyamide 3 ("3"), Control polyamide 3 and JQ1-(S) (unconjugated), Agent 4 ("4"), and Control polyamide 3 bound to JQ1 without a linker ("3-JQ1-(S)")).

FIG. 4 is a graph showing relative RNA concentrations of cells harvested after 24 hours of treatment with each of the molecules described above. The results show that, without a linker, 3-JQ1-(S) is cytotoxic. The results also show that cells treated with the conjugate molecules (Agent 4) have higher RNA concentrations than those treated with JQ1-(S) or unconjugated Control polyamide 3+JQ1-(S). JQ1-(S) is known to cause cell cycle arrest.

Methods

GM15850 cells were passaged into fresh medium at a concentration of 500,000 cells/mL. The cells were seeded into a 24-well plate and treated with the described compounds for 24 hours in quadruplicate. After 24 hours, the cells were collected, media was removed, and RNA was harvested with a Qiagen RNeasy Mini-Kit (Qiagen, Valencia, Calif.). RNA concentrations were then measured by nanodrop UV-Vis spectrophotometry.

Example 7: Lymphoblastoid Cell Line (LCL) Data

To assess the effects of treatment with the compositions of the present technology on frataxin (FXN) mRNA levels in lymphoblastoid cells, mRNA levels from three different lymphoblastoid cell lines (LCL) derived from FRDA patient samples were measured after 24 hours of treatment with the Control polyamide 3 and JQ1 (unconjugated) ("3+JQI") or Agent 4 ("4").

Figure 6:
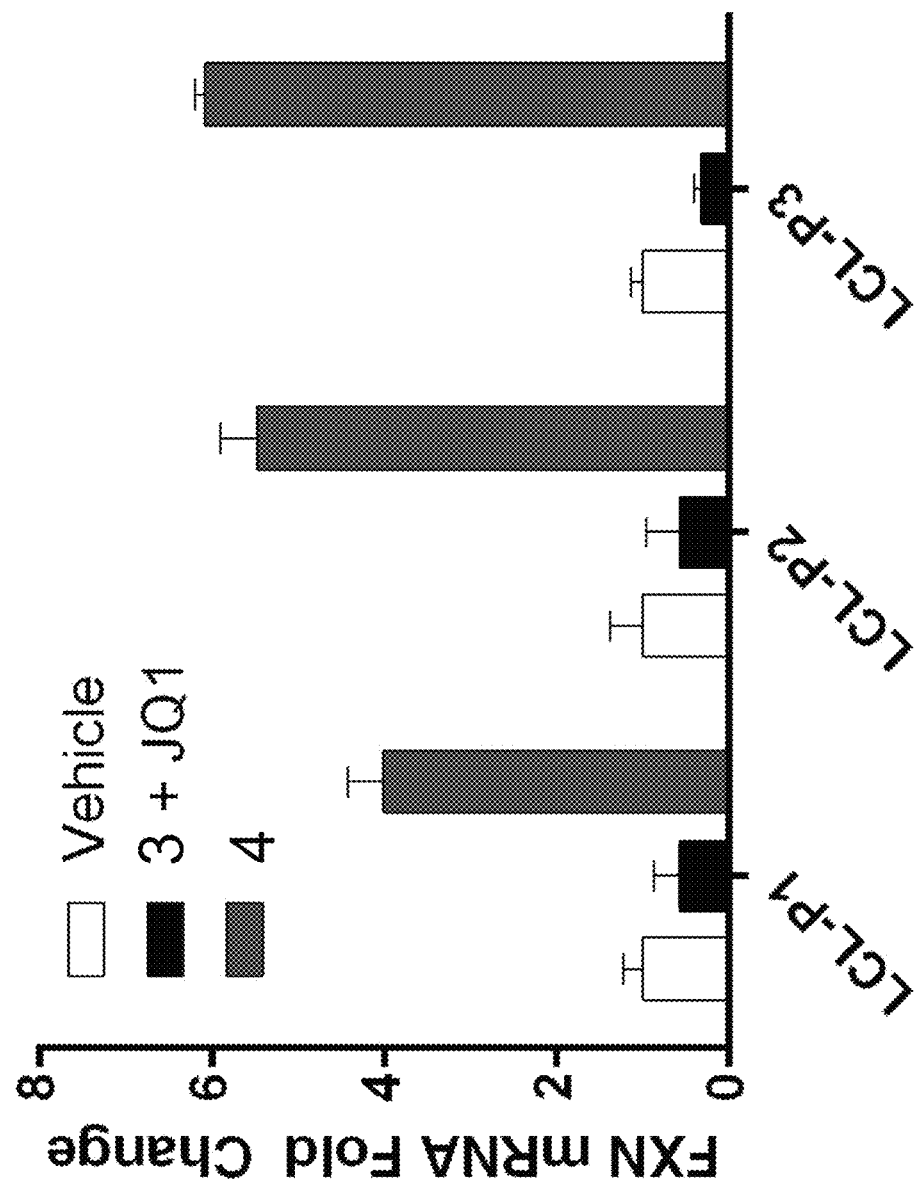
FIG. 6 is a bar graph showing relative frataxin (FXN) mRNA levels produced in lymphoblastoid cell lines derived from three FRDA patients (P1-P3) following incubation for 24 hours with 1 μM Control polyamide 3 and unbound JQ1 ("3+JQ1") or 1 μM Agent 4 ("4").

FIG. 6 is a graph showing relative frataxin (FXN) mRNA levels from three different lymphoblastoid cell lines that were derived from patient samples (LCL-P1, LCL-P2, and LCL-P3). Treatments were fore 24 hours with the described molecules. The results demonstrate an increase in FXN mRNA after treatment of lymphoblastoid cells from FRDA patients with Agent 4.

Methods

FRDA patients (n=3), LCL generation was carried out by Epstein Barr Virus (EBV) induced transduction of B cells, isolated from healthy individuals and patients. The following steps were taken: (a) 2-3×10$^6$ cells/ml were seeded into T25 flask (Nunc) in RPMI 1640 medium (Himedia) containing 15% FBS (Gibco), 2 mM glutamine (Invitrogen) with the presence of antibiotics, Penicillin (100 I.U./mL) and Streptomycin (100 µg/mL) (Invitrogen); (b) 3 mL of EBV supernatant was added in the flask and kept upright for 3 hours in an incubator (Eppendort) set at 37° C. with 5% $CO_2$); (c) after 3 hours, 3 mL of 20% RPMI-1640 containing 2 ug/mL of cyclosporine A (Sigma) was added and incubated upright for 6 days without feeding (cells started showing small clumps and changes in morphology from the 5-6th day onwards depending on the cell line); (d) on the 6th day complete medium change was done by spinning down cells at 1000 rpm for 3 minutes and re-suspending the pellet in 15% fresh complete RPMI medium; and (e) after 2-3 weeks of incubation, appearance of rosette/clump morphology of cells indicate the transformed phenotype of PBMCs.

The treatments and data collection were performed as follows. Compound treatments were given in quadruplicate. Each cell line was further divided into DMSO/Unconjugated/Conjugate categories (Total 6×10$^6$ cells were seeded in 12-well plate (Nunc, Delta Surface) at density of 0.5×10$^6$ cells per well in a final volume of 1 mL medium). In vehicle control (DMSO treated group) 1.0 µL DMSO (Sigma) i.e., 0.1% v/v was added, whereas for Unconjugated and Conjugate categories the final concentration of respective compounds were kept 1.0 µM. After 24 hours of incubation, treated cells were further taken for RNA isolation. RNA was harvested with Qiagen RNeasy mini-kit per manufacturer's instructions. RT was done with Applied Biosystem's cDNA synthesis kit. Standard qPCR was performed, normalizing to GAPDH.

Example 8: Peripheral Blood Mononuclear (PBMC) Data

Figure 7:
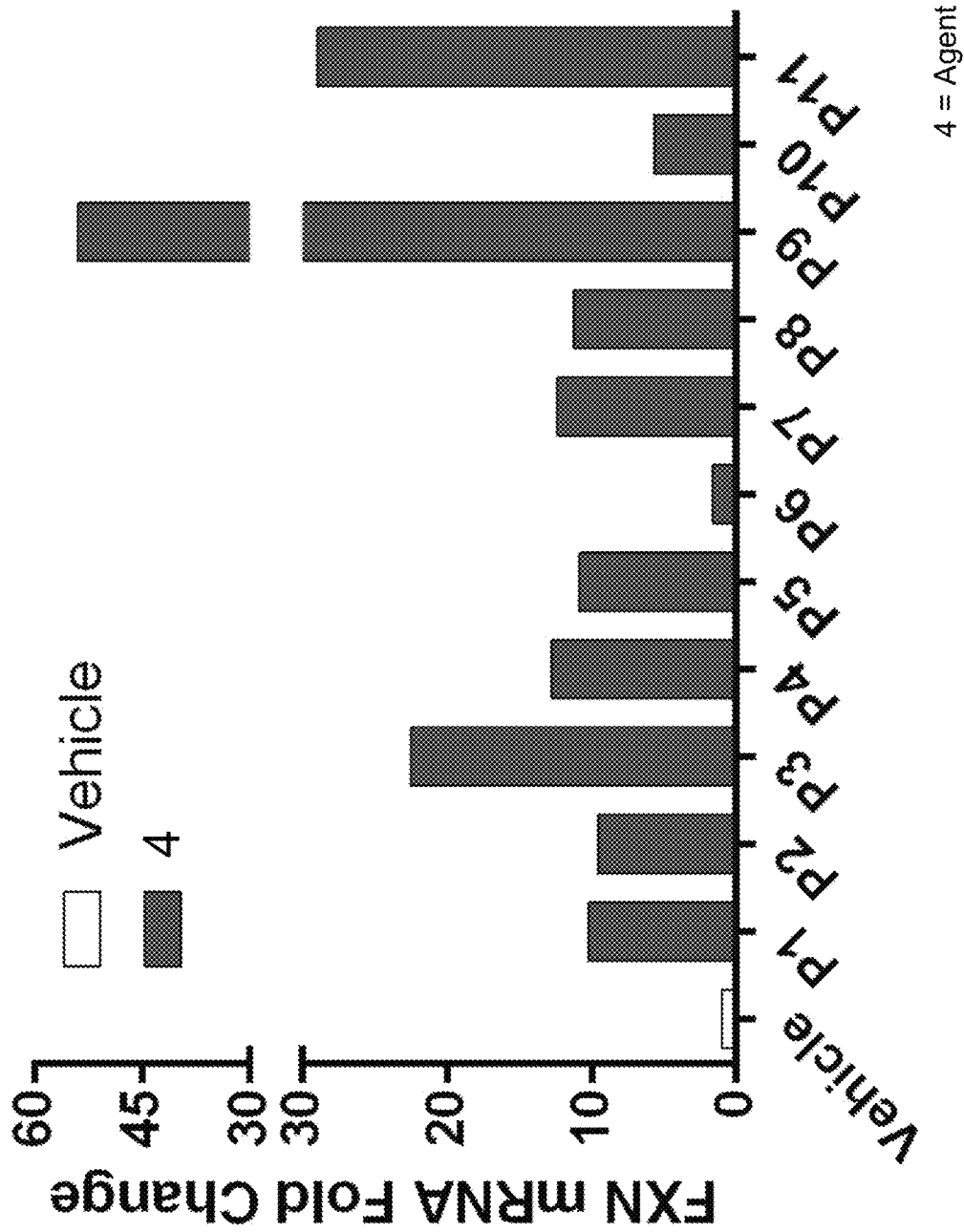
FIG. 7 is a bar graph showing relative frataxin (FXN) mRNA levels produced in primary samples of peripheral blood mononuclear cells (PBMCs) derived from eleven FRDA patients (P1-P11) following incubation for 24 hours with 1 µM Agent 4 ("4").

To assess the effects of treatment with the compositions of the present technology on frataxin (FXN) mRNA levels in primary patient peripheral blood mononuclear cells (PBMCs), mRNA levels from eleven different PBMC samples derived from FRDA patients (P1-P11) were measured after 24 hours of treatment with Agent 4 ("4") (FIG. 7).

FIG. 7 is a graph showing relative FXN mRNA levels from eleven different PBMC samples derived from FRDA patients following 24-hour treatment with Agent 4. The results demonstrate an increase in FXN mRNA after treatment of PBMCs from FRDA patients with Agent 4.

Methods

PBMC isolation was done using Ficoll Histopaque gradient (Sigma-Aldrich) and the number of cells present were counted using hemocytometer. Peripheral blood was drawn from FRDA patients into ACD Buffer vial and stored at room temperature. Biological safety cabinet (ESCO Class II BSC) and required materials were cleaned thoroughly with 70% ethanol (Merck KGaA). Meanwhile, 1×DPBS (Gibco Life technology Ref. 14190-144), Ficoll Histopaque (Sigma Lot #RNBF-2365), 15% RPMI-1640 (HIMEDIA Ref.- AL060), HIFBS (Gibco Cat. no. 10082147) were warmed in water bath set at 37° C. (Sun Scientific Industries). 8 mL of blood was diluted with 8 mL 1×DPBS (1:1), and mixed properly to make it a homogeneous solution. Carefully, 8 mL diluted blood cell suspension was layered over 4 mL of Histopaque (1:2 ratio) in a 15 mL falcon tube. The falcons were spun at 400×g for 40 minutes in swing out bucket rotor without break (Heraceus Megafuge-16R Centrifuge), at room temperature. After centrifugation, the upper layer leaving the whitish buffy coat (lymphocyte layer) was transferred into new 15 mL falcon and brought up to 4 mL with 1×DPBS. The falcons were spun at 400×g for 12 minutes with breaks on. The previous step was repeated. The supernatant was discarded and cell pellet was re-suspended in 15% RPMI. Cell count was performed using Hemocytometer.

The treatments and data collection were performed as follows. Compound treatments were given in quadruplicate. Each cell line was further divided into DMSO/Unconjugated/Conjugate categories (Total 6×10$^6$ cells were seeded in 12-well plate (Nunc, Delta Surface) at density of 0.5×10$^6$ cells per well in a final volume of 1 mL medium). In vehicle control (DMSO treated group) 1.0 µL DMSO (Sigma) i.e., 0.1% v/v was added, whereas for Unconjugated and Conjugate categories the final concentration of respective compounds were kept 1.0 µM. After 24 hours of incubation, treated cells were further taken for RNA isolation. RNA was harvested with Qiagen RNeasy mini-kit per manufacturer's instructions. RT was done with Applied Biosystem's cDNA synthesis kit. Standard qPCR was performed, normalizing to GAPDH.

Example 9: Binding of the Agents of the Present Technology to Brd4

Figure 8:
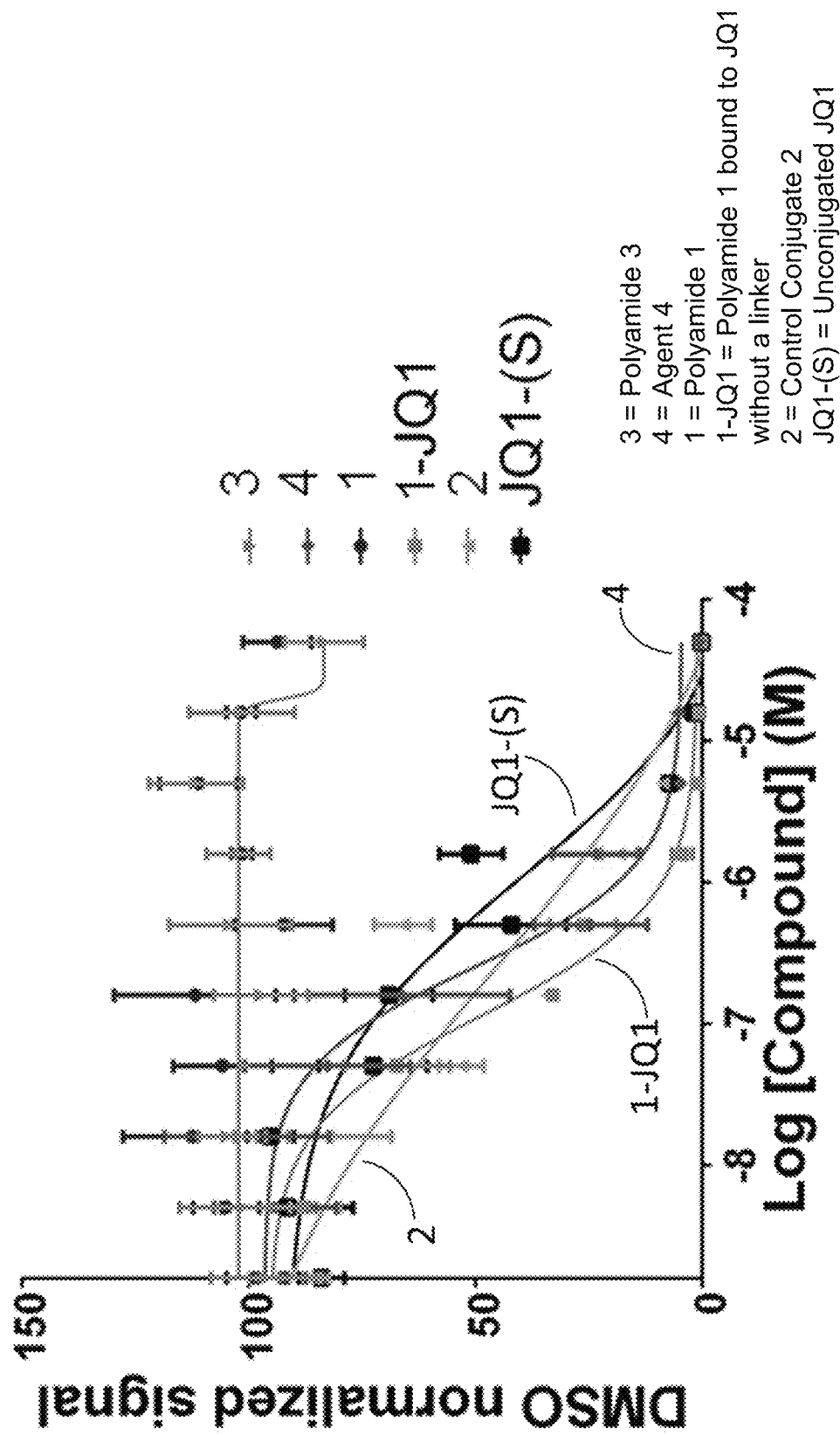
FIG. 8 is a chart showing the results of an AlphaScreen™ assay of the binding of Control polyamide 3 ("3"), Agent 4 ("4"), Control polyamide 1 ("1"), Control polyamide 1 bound to JQ1 without a linker ("1-JQ1"), and unconjugated JQ1 ("JQ1-(S)") to Bdr4.
Figure 9A:
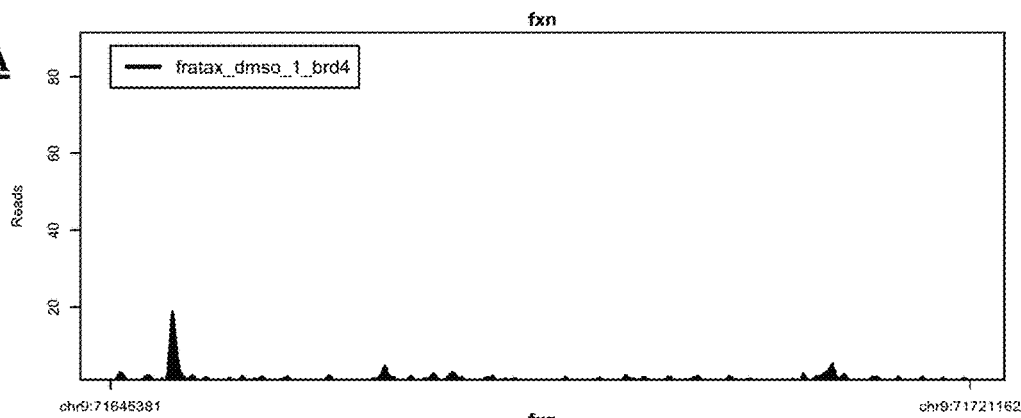
FIGS. 9A-9D show ChIP-seq data plots of read density over the entire frataxin (FXN) gene body (FIG. 9D) for Brd4 (FIGS. 9A-9C) following incubation for 24 hours with a control solution (0.1% DMSO, FIG. 9A) or 1 µM Control polyamide 3 and unbound JQ1 ("3+JQ1", FIG. 9B) or 1 µM Agent 4 ("4", FIG. 9C).
Figure 9B:
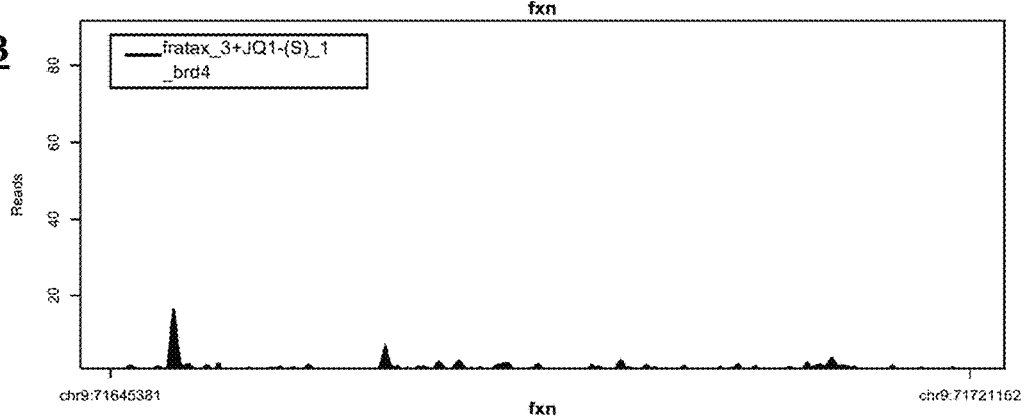
Figure 9C:
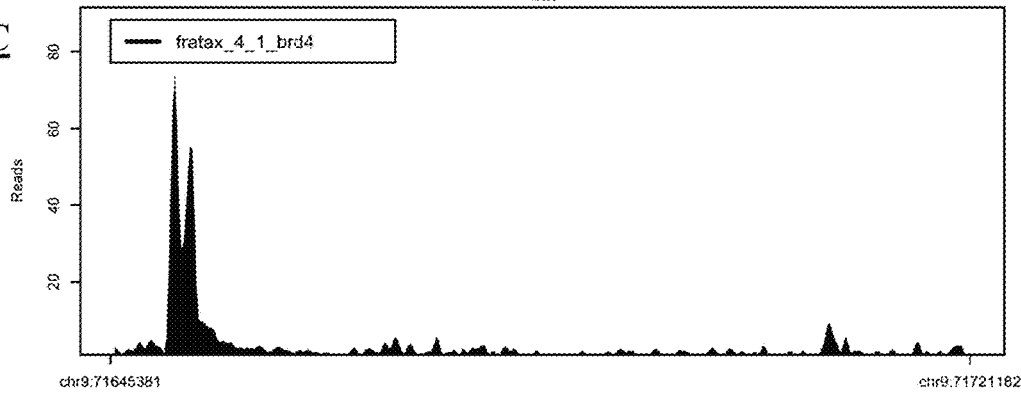
Figure 9D:
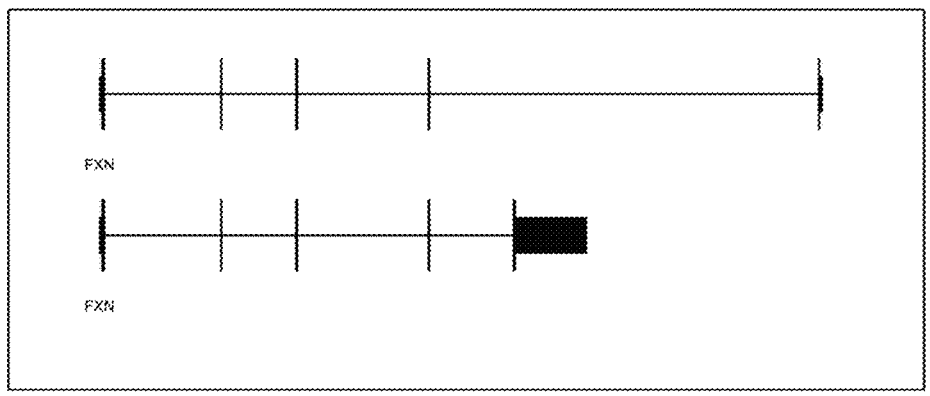
Figure 10A:
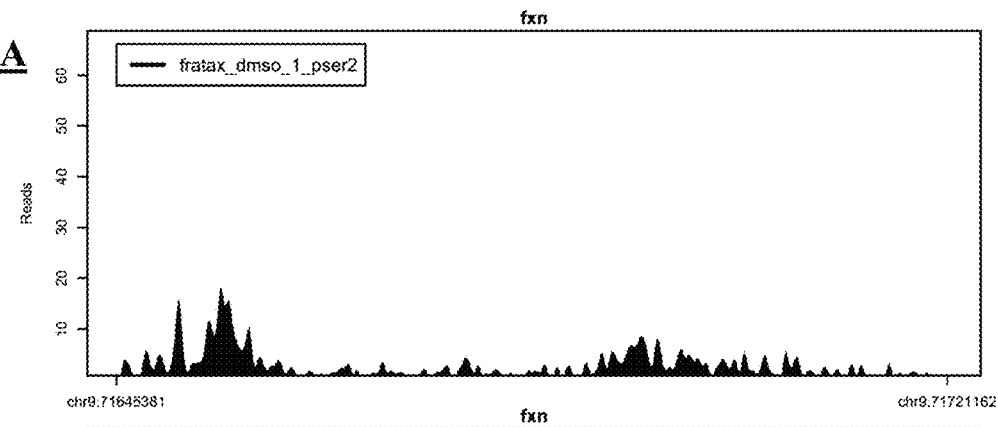
FIGS. 10A-10D show ChIP-seq data plots of read density over the entire frataxin (FXN) gene body (FIG. 10D) for pSer2 (phosphorylated Ser2 of the carboxy-terminal domain (CTD) of RNA polymerase II) (FIGS. 10A-10C) following incubation for 24 hours with a control solution (0.1% DMSO, FIG. 10A) or 1 µM Control polyamide 3 and unbound JQ1 ("3+JQ1", FIG. 10B) or 1 µM Agent 4 ("4", FIG. 10C).
Figure 10B:
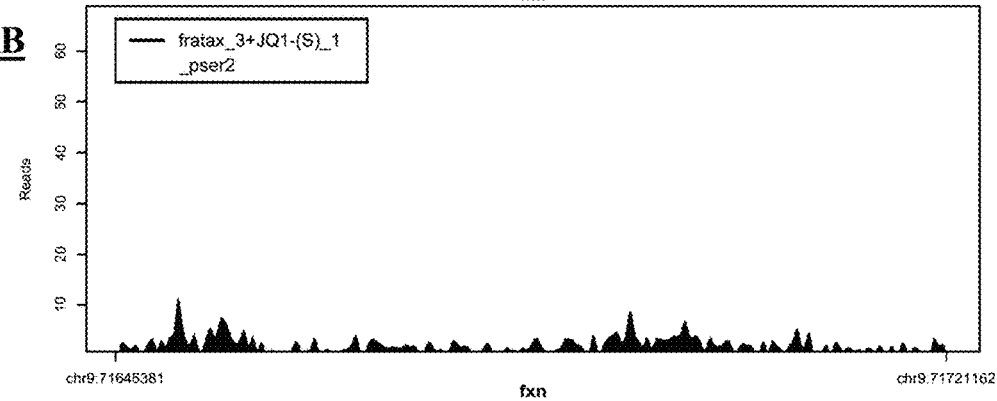
Figure 10C:
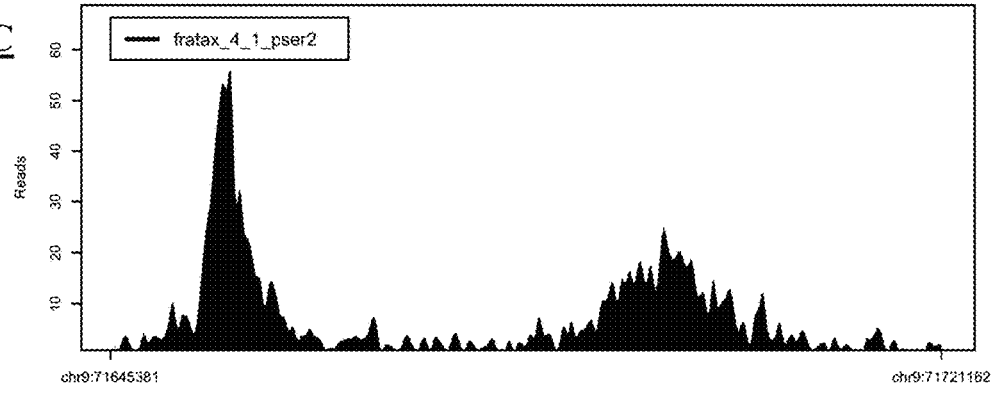
Figure 10D:
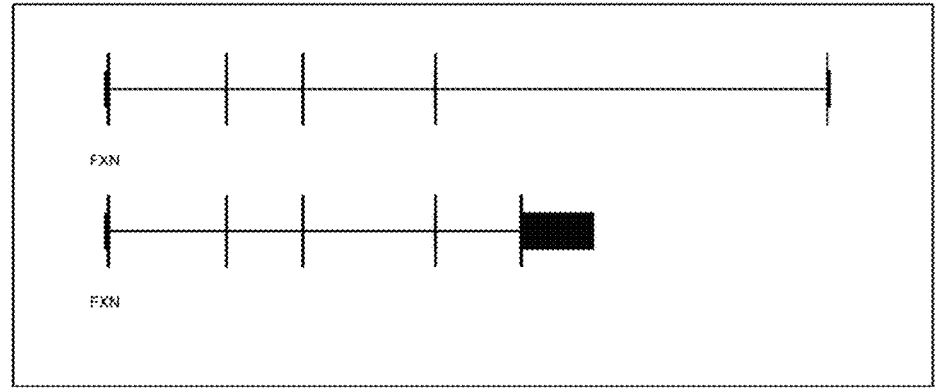
Figure 11A:
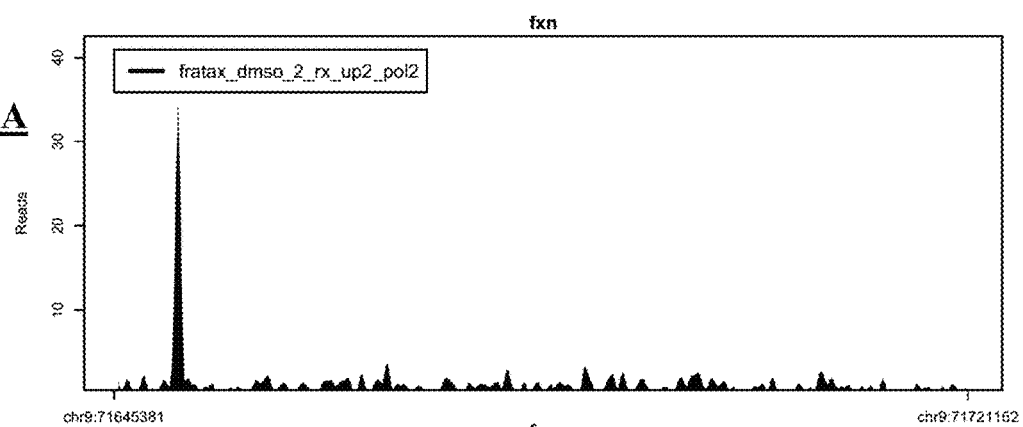
FIGS. 11A-11D show ChIP-seq data plots of read density over the entire frataxin (FXN) gene body (FIG. 11D) for pol2 (RNA polymerase II) (FIGS. 11A-11C) following incubation for 24 hours with a control solution (0.1% DMSO, FIG. 11A) or 1 µM Control polyamide 3 and unbound JQ1 ("3+JQ1", FIG. 11B) or 1 µM Agent 4 ("4", FIG. 11C).
Figure 11B:
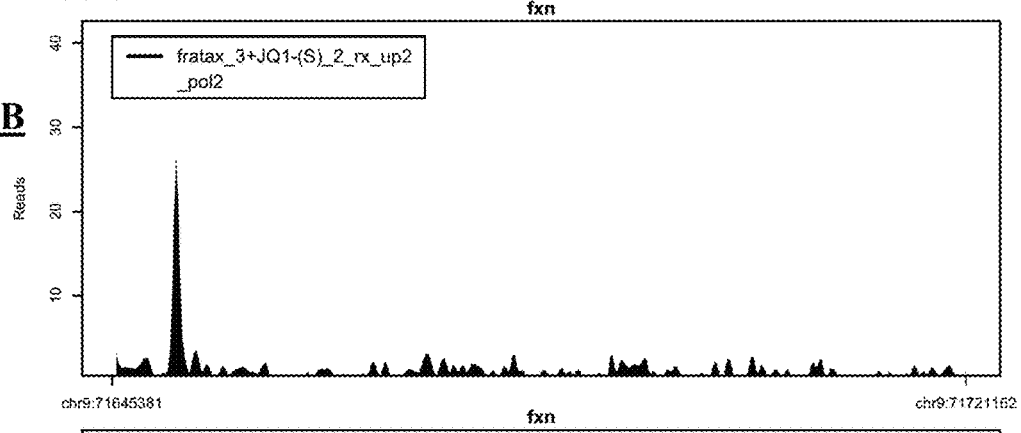
Figure 11C:
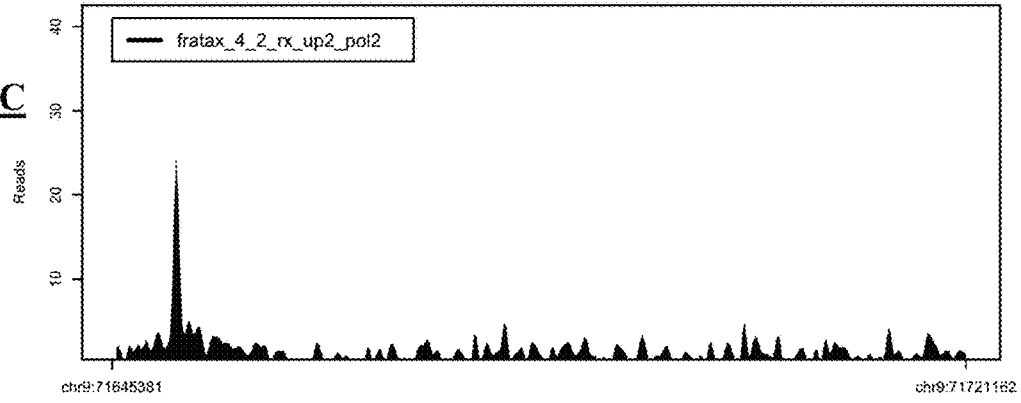
Figure 11D:
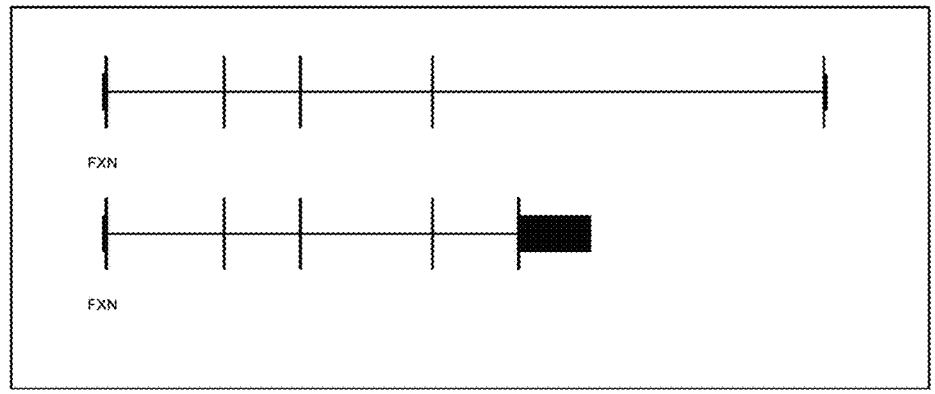

To confirm that the conjugates of the present technology bind to Brd4, an AlphaScreen™ assay (Amplified Luminescent Proximity Homogeneous assay) was performed. FIG. 8 is a graph showing the binding of the molecules of the present technology to Brd4 (the target of JQ1-(S)). The results demonstrate that the conjugates bind to Brd4 as well as JQ1-(S) does independently.

Methods

The AlphaScreen™ assay is a bead-based proximity assay. There are acceptor and donor beads that, when proximal, amplify a chemiluminescent signal via reaction with a singlet oxygen species. For this assay, Brd4 and acetylated lysine are each bound to one type of bead. Then, as compounds are titrated, signal disappears due to out competing the acetylated lysine residues. Compounds ranged in concentration from 10 nM to 1 µM.

Example 10: ChIP-Sequencing at the FXN Locus

To confirm that the conjugates of the present technology recruit Brd4, the super elongation complex, and a Cdk9 kinase that phosphorylates Ser2 of the CTD of RNA Polymerase II, a series of ChIP-seq experiments were performed. FIGS. 9-10 show an FXN locus increase in Brd4 (FIG. 9C) and pSer2 (FIG. 10 Co-occupancy in the Agent 4-treated GM15850 cells relative to DMSO- and 3+JQ1-(S)-treated GM15850 cells. In the case of RNAPol2 (pol2) (FIG. 11C), FIG. 11 shows an increase in elongating RNAPol2 moving through the FXN locus gene body in the Agent 4-treated GM15850 cells relative to DMSO- and 3+JQ1-(S)-treated GM15850 cells.

Methods

This is an example of a typical ChIP-Rx experiment. It is ChIP-seq but with a *drosophila* spike-in for better normalization. According to methods known in the art, three different IPs were done (Total RNAPol2, phospho-Ser2 of the CTD of RNAPol2, and Brd4). Brd4 required more cells (~$10^8$ per treatment) compared to the others (~$2.5 \times 10^7$). Three treatments were performed for 24 hours in GM15850 cells (DMSO, unconjugated 3+JQ1-(S), and Agent 4, both at 1 µM). The plots shown in FIGS. 9A-9C, FIGS. 10A-10C, and FIGS. 11A-11C are of read density over the entire frataxin gene body.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the appended claims. The present technology is to be limited only by the terms of the appended claims, along with the full scope of equivalents to which such claims are entitled. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. As will also be understood by one skilled in the art all language such as "up to," "at least," and the like, include the number recited.

What is claimed is:

1. An agent having a formula A-L-B, wherein:
-L- is a linker;
A- is a Brd4 binding moiety selected from the group consisting of triazolodiazepines having a structure

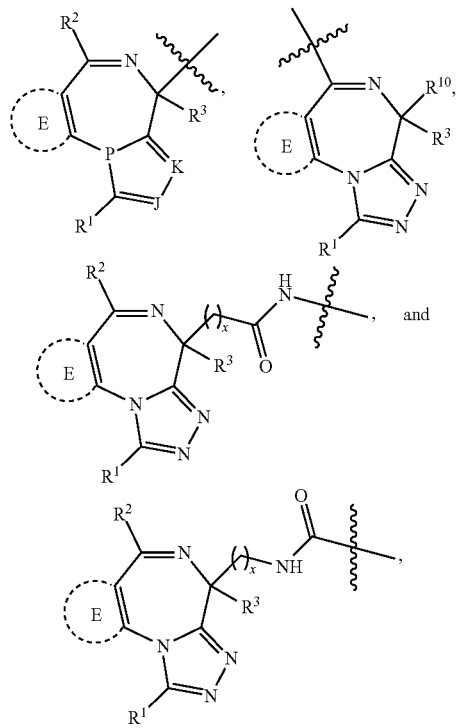

wherein:

J is N, O or CR[11]; K is N, O or CR[11]; with the proviso that J and K cannot both be —O—; P is N, except when one of J or K is —O—, P is C, wherein R[11] is a hydrogen or optionally substituted alkyl, cycloalkyl, heterocycloalkyl, aryl, or heteroaryl group, R[1] is a hydrogen or optionally substituted alkyl, hydroxyalkyl, aminoalkyl, alkoxyalkyl, halogenated alkyl, hydroxyl, alkoxy, or —COOR[4], wherein R[4] is a hydrogen, substituted or unsubstituted arylene, aralkylene, cycloalkylene, heteroarylene, heteroaralkylene, heterocycloalkylene, alkylene, alkenylene, alkynylene, or cycloalkylalkylene group optionally interrupted by one or more heteroatoms, R[2] is an optionally substituted aryl, alkyl, cycloalkyl, or aralkyl group, R3 and R10 are each independently a hydrogen, halogen, or optionally substituted alkyl group, "x" is an integer of from 1 to 10, and Ring E is an optionally substituted aryl or heteroaryl ring; and thienotriazolodiazepines having a structure

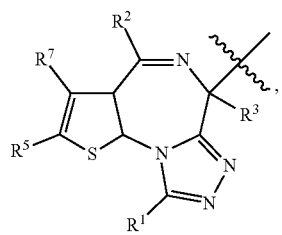

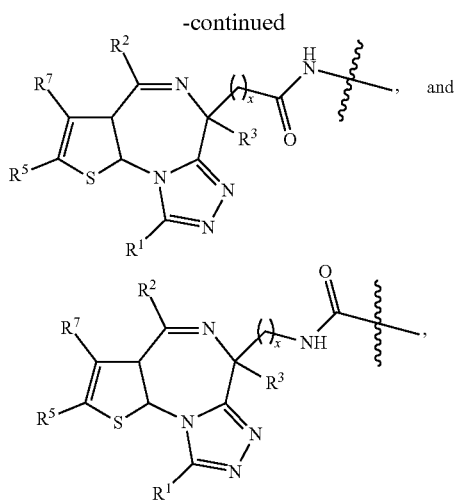

wherein:
R² is an aryl group optionally substituted with one or more substituted or unsubstituted alkyl, alkenyl, alkynyl, halogen, —OR⁶, —SR⁶, —N(R⁶)₂, —N(R⁶)COR⁹ groups, wherein R⁶ and R⁹ are independently a hydrogen or alkyl group, R¹ and R³ are independently a hydrogen or optionally substituted alkyl group, R⁵ and R⁷ are each independently a hydrogen, alkyl, alkenyl, alkynyl, halogen, halogenated alkyl, —OH, —SH, or —NH₂, and "x" is an integer of from 1 to 10; and —B is a nucleic acid binding moiety that specifically binds to one or more repeats of a target oligonucleotide sequence selected from the group consisting of CGG, CTG, and CCTG.

2. The agent of claim 1, wherein the nucleic acid binding moiety —B is a polyamide that specifically binds to the one or more repeats of the target oligonucleotide sequence.

3. The agent of claim 1, wherein the nucleic acid binding moiety —B is a second oligonucleotide sequence that specifically binds to the target oligonucleotide sequence.

4. A pharmaceutical composition comprising a therapeutically effective amount of the agent of claim 1 and a pharmaceutically acceptable carrier.

5. A method for modulating mRNA levels produced from a gene in a cell comprising contacting the cell with an effective amount of the agent of claim 1, wherein the gene comprises more than one repeat of the target oligonucleotide sequence.

6. The method of claim 5, wherein the gene comprises at least about 30 repeats of the target oligonucleotide sequence.

7. The method of claim 5, wherein the mRNA levels are increased by at least about 2.5-fold relative to an untreated cell.

8. A method for increasing levels of a protein in a cell, comprising contacting the cell with an effective amount of the agent of claim 1, wherein the protein is encoded by a gene, wherein the gene comprises more than one repeat of the target oligonucleotide sequence.

9. The agent of claim 2, wherein the nucleic acid binding moiety —B comprises a subunit selected from the group consisting of:

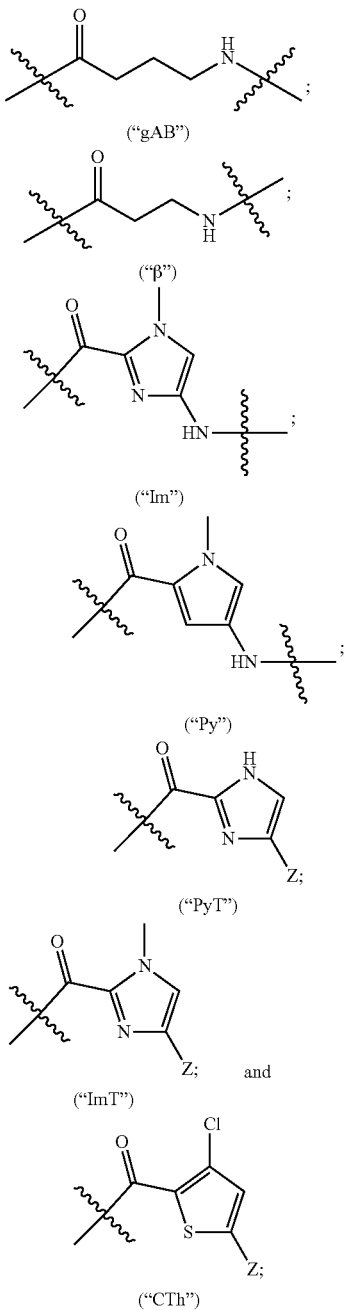

wherein Z is hydrogen, amino, or amido.

10. The agent of claim 9, wherein Z is —H, —NR^B R^B, —N⁺R^A R^B R^B, or —N(R^A)C(O)R^B; wherein R^A is hydrogen; and R^B is selected from the group consisting of hydrogen, C₁-C₆ alkyl, C₁-C₆ alkenyl, and C₁-C₆ alkynyl group.

11. The agent of claim 10, wherein R^B is hydrogen or —CH₃.

12. The agent of claim 1, wherein the linker -L- has a backbone chain comprising at least about 10 contiguous atoms.

13. The agent of claim 12, wherein the linker -L- has a backbone chain comprising 15 to 30 contiguous atoms.

14. The agent of claim 13, wherein the linker -L- comprises a combination of one or more optionally substituted arylene, aralkylene, cycloalkylene, heteroarylene, heteroaralkylene, heterocycloalkylene, alkylene, alkenylene, alkynylene, or cycloalkylalkylene groups, optionally interrupted by one or more heteroatoms, amido, or carboxyl groups.

15. The agent of claim 13, wherein the linker -L- comprises a combination of one or more linking moieties selected from the group consisting of —O—, —(CH$_2$)$_x$—, —(CH$_2$CH$_2$O)$_y$—, —(OCH$_2$CH$_2$)$_y$—, —C(O)NR'—, —NR'C(O)—, —C(O)—, —NR*—,

—(CH$_2$CH$_2$CH$_2$O)$_y$—, and —(OCH$_2$CH$_2$CH$_2$)$_y$—,
wherein R' and R* are each independently a hydrogen or C$_1$-C$_6$ alkyl; and
x and y are each independently an integer from 1-10.

16. The agent of claim 13, wherein the linker -L- comprises
—(CH$_2$)$_x$—C(O)N(R')—(CH$_2$)$_Q$—N(R*)—(CH$_2$)$_Q$—N(R')C(O)—(CH$_2$)$_x$—C(O)N(R')—,
—(CH$_2$)$_x$—C(O)N(R')—(CH$_2$CH$_2$O)$_y$—(CH$_2$)$_x$—C(O)N(R')—,
—C(O)N(R')—(CH$_2$)$_Q$—N(R*)—(CH$_2$)$_Q$—N(R')C(O)—(CH$_2$)$_x$—,
—(CH$_2$)$_x$—O—(CH$_2$CH$_2$O)$_y$—(CH$_2$)$_x$—N(R')C(O)—(CH$_2$)$_x$—, or
—N(R')C(O)—(CH$_2$)$_x$—C(O)N(R')—(CH$_2$)$_x$—O—(CH$_2$CH$_2$O)$_y$—(CH$_2$)$_x$—;
wherein R* is methyl, R' is hydrogen; y is an integer from 1 to 10; Q is an integer from 2 to 10; and x is an integer from 1 to 10.

17. The agent of claim 13, wherein the linker -L- comprises one or more linking moieties selected from, Gly-Ser-Gly, (Gly-Ser-Gly)v (SEQ ID NOS:14 and 22-29), Gly-Gly-Ser, and (Gly-Gly-Ser)w (SEQ ID NOS:15 and 30-37), where v and w are independently integers from 2 to about 10.

18. The agent of claim 1, wherein the Brd4 binding moiety A- has the structure:

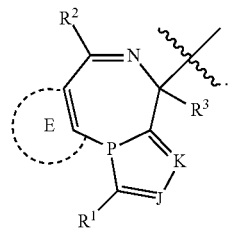

19. The agent of claim 1, wherein the Brd4 binding moiety A- is a thienotriazolodiazepine.

20. The agent of claim 1, wherein the Brd4 binding moiety A- has the structure:

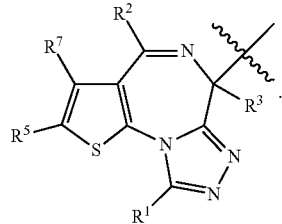

21. The agent of claim 1, wherein R$^2$ is a phenyl group optionally substituted with one or more alkyl, halogenated alkyl, alkoxy, hydroxyalkyl, cyano, and/or halogen substituents.

22. The agent of claim 1, wherein R$^2$ is a phenyl group optionally substituted with one or more halogens.

23. The agent of claim 1, wherein the Brd4 binding moiety A- has the structure:

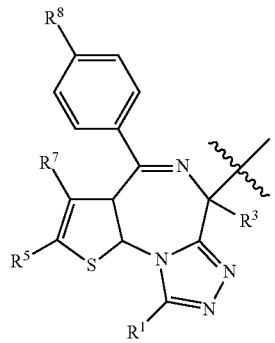

wherein R$^3$ is hydrogen or —CH$_3$;
R$^1$, R$^5$, and R$^7$ are each independently hydrogen, methyl, ethyl, or halomethyl group; and
R$^8$ is a halogen.

24. The agent of claim 23, wherein R$^3$ is hydrogen or —CH$_3$; R$^1$, R$^5$, and R$^7$ are —CH$_3$; and R$^8$ is chloro.

25. The agent of claim 1, wherein
L- comprises a backbone chain which includes at least about 10 contiguous atoms;
—B is a polyamide that specifically binds to one or more repeats of the target oligonucleotide sequence; and
A- is

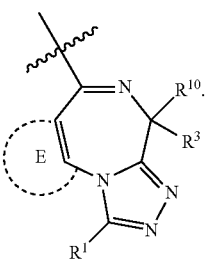

26. The agent of claim 9, wherein the target oligonucleotide sequence is CGG; and —B comprises a polyamide sequence selected from the group consisting of:
-Im-Py-Py-Im-gAB-Py-Im-Im-Py-; -Im-Py-Py-Im-gAB-Py-Im-Im-PyT;
Im-Py-Py-Im-gAB-Py-Im-Im-β-; -Im-β-Py-Im-gAB-Py-Im-Im-β-;

-Im-β-Py-Im-gAB-Py-Im-Im-Py-; -Im-β-Py-Im-gAB-Py-Im-Im-PyT;
-Py-Py-Im-β-gAB-Im-Py-Im-Im-; -Py-Py-Im-β-gAB-Im-Py-Im-ImT;
-Py-Py-Im-Py-gAB-Im-Py-Im-Im-; -Py-Py-Im-Py-gAB-Im-Py-Im-ImT;
-Py-Py-Im-β-gAB-Im-β-Im-Im-; -Py-Py-Im-β-gAB-Im-β-Im-ImT;
-Py-Py-Im-Py-gAB-Im-β-Im-Im-; -Py-Py-Im-Py-gAB-Im-β-Im-ImT;
-Im-β-Py-gAB-Im-Im-Py-; -Im-β-Py-gAB-Im-Im-PyT;
-Im-β-Py-gAB-Im-Im-β-; -Im-Py-Py-gAB-Im-Im-β-;
-Im-Py-Py-gAB-Im-Im-Py-; and -Im-Py-Py-gAB-Im-Im-PyT.

27. The agent of claim 9, wherein the oligonucleotide sequence is CCTG; and —B comprises a polyamide sequence selected from the group consisting of:
-Py-Im-Im-β-gAB-Py-Py-Py-Im-; -Py-Im-Im-β-gAB-Py-Py-Py-ImT;
-Py-Im-Im-Py-gAB-Py-Py-Py-Im-; -Py-Im-Im-Py-gAB-Py-Py-Py-ImT;
-Py-Im-Im-gAB-Py-Py-Im-; -Py-Im-Im-gAB-Py-Py-ImT;
-Py-Py-Im-Im-gAB-Py-Py-Im-Py-; -Py-Py-Im-Im-gAB-Py-Py-Im-PyT;
-Py-Py-Im-Im-gAB-Py-Py-Im-β-;
-Im-Py-Py-gAB-Im-β-Py-; -Im-Py-Py-gAB-Im-β-PyT;
-Im-β-Py-gAB-Im-Py-Py-; -Im-β-Py-gAB-Im-Py-PyT;
-Im-β-Py-gAB-Im-β-Py-; -Im-β-Py-gAB-Im-β-PyT;
-Im-Py-Py-gAB-Im-Py-Py-; and -Im-Py-Py-gAB-Im-Py-PyT.

28. The agent of claim 9, wherein the oligonucleotide sequence is CTG; and —B comprises a polyamide sequence selected from the group consisting of:
-Im-Py-Py-Im-gAB-Py-Im-Py-Py-; -Im-Py-Py-Im-gAB-Py-Im-Py-PyT;
-Im-β-Py-Im-gAB-Py-Im-Py-Py-; -Im-β-Py-Im-gAB-Py-Im-Py-PyT;
-Im-Py-Py-Im-gAB-Py-Im-β-Py-; -Im-Py-Py-Im-gAB-Py-Im-β-PyT;
-Im-β-Py-Im-gAB-Py-Im-β-Py-; -Im-β-Py-Im-gAB-Py-Im-β-PyT
-Py-Im-β-Im-gAB-Py-Py-Py-Im-; -Py-Im-β-Im-gAB-Py-Py-Py-ImT;
-Py-Im-Py-Im-gAB-Py-Py-Py-Im-; -Py-Im-Py-Im-gAB-Py-Py-Py-ImT;
-Py-Im-Py-Py-gAB-Im-Py-Py-Im-; -Py-Im-Py-Py-gAB-Im-Py-Py-ImT;
-Py-Im-β-Py-gAB-Im-Py-Py-Im-; -Py-Im-β-Py-gAB-Im-Py-Py-ImT;
-Py-Im-Py-Py-gAB-Im-β-Im-Im-; -Py-Im-Py-Py-gAB-Im-β-Py-ImT;
-Py-Im-β-Py-gAB-Im-β-Py-Im-; -Py-Im-β-Py-gAB-Im-β-Py-ImT;
-Py-Im-Py-Py-gAB-Im-β-Py-Im-; -Py-Im-Py-Py-gAB-Im-β-Py-ImT;
-Im-β-Py-gAB-Im-Py-Py-; -Im-β-Py-gAB-Im-Py-PyT;
-Im-β-Py-gAB-Im-β-Py-; -Im-β-Py-gAB-Im-β-PyT;
-Im-Py-Py-gAB-Im-Py-Py-; -Im-Py-Py-gAB-Im-Py-PyT;
-Im-Py-Py-gAB-Im-β-Py-; and -Im-Py-Py-gAB-Im-β-PyT.

29. The method of claim 5, wherein the gene is selected from the group consisting of Fragile X Mental Retardation 1 (FMR1), dystrophia myotonica protein kinase (DMPK), and zinc finger 9 (ZNF9).

30. The method of claim 8, wherein the gene is selected from the group consisting of Fragile X Mental Retardation 1 (FMR1), dystrophia myotonica protein kinase (DMPK), and zinc finger 9 (ZNF9).

* * * * *

SEQUENCE LISTING

```
<160> NUMBER OF SEQ ID NOS: 37

<210> SEQ ID NO 1
<211> LENGTH: 718
<212> TYPE: PRT
<213> ORGANISM: Homo sapiens

<400> SEQUENCE: 1

Met Ser Ala Glu Ser Gly Pro Gly Thr Arg Leu Arg Asn Leu Pro Val
1               5                   10                  15

Met Gly Asp Gly Leu Glu Thr Ser Gln Met Ser Thr Thr Gln Ala Gln
                20                  25                  30

Ala Gln Pro Gln Pro Ala Asn Ala Ala Ser Thr Asn Pro Pro Pro Pro
            35                  40                  45

Glu Thr Ser Asn Pro Asn Lys Pro Lys Arg Gln Thr Asn Gln Leu Gln
    50                  55                  60

Tyr Leu Leu Arg Val Leu Lys Thr Leu Trp Lys His Gln Phe Ala Trp
65                  70                  75                  80

Pro Phe Gln Gln Pro Val Asp Ala Val Lys Leu Asn Leu Pro Asp Tyr
                85                  90                  95

Tyr Lys Ile Ile Lys Thr Pro Met Asp Met Gly Thr Ile Lys Lys Arg
            100                 105                 110

Leu Glu Asn Asn Tyr Tyr Trp Asn Ala Gln Glu Cys Ile Gln Asp Phe
        115                 120                 125

Asn Thr Met Phe Thr Asn Cys Tyr Ile Tyr Asn Lys Pro Gly Asp Asp
    130                 135                 140
```

-continued

```
Ile Val Leu Met Ala Glu Ala Leu Glu Lys Leu Phe Leu Gln Lys Ile
145                 150                 155                 160

Asn Glu Leu Pro Thr Glu Glu Thr Glu Ile Met Ile Val Gln Ala Lys
            165                 170                 175

Gly Arg Gly Arg Gly Arg Lys Glu Thr Gly Thr Ala Lys Pro Gly Val
        180                 185                 190

Ser Thr Val Pro Asn Thr Thr Gln Ala Ser Thr Pro Gln Thr Gln
    195                 200                 205

Thr Pro Gln Pro Asn Pro Pro Val Gln Ala Thr Pro His Pro Phe
    210                 215                 220

Pro Ala Val Thr Pro Asp Leu Ile Val Gln Thr Pro Val Met Thr Val
225                 230                 235                 240

Pro Pro Gln Pro Leu Gln Thr Pro Pro Val Pro Pro Gln Pro Gln
                245                 250                 255

Pro Pro Pro Ala Pro Ala Pro Gln Pro Val Gln Ser His Pro Pro Ile
            260                 265                 270

Ile Ala Ala Thr Pro Gln Pro Val Lys Thr Lys Lys Gly Val Lys Arg
        275                 280                 285

Lys Ala Asp Thr Thr Thr Pro Thr Thr Ile Asp Pro Ile His Glu Pro
290                 295                 300

Pro Ser Leu Pro Pro Glu Pro Lys Thr Thr Lys Leu Gly Gln Arg Arg
305                 310                 315                 320

Glu Ser Ser Arg Pro Val Lys Pro Pro Lys Lys Asp Val Pro Asp Ser
                325                 330                 335

Gln Gln His Pro Ala Pro Glu Lys Ser Ser Lys Val Ser Glu Gln Leu
            340                 345                 350

Lys Cys Cys Ser Gly Ile Leu Lys Glu Met Phe Ala Lys Lys His Ala
        355                 360                 365

Ala Tyr Ala Trp Pro Phe Tyr Lys Pro Val Asp Val Glu Ala Leu Gly
    370                 375                 380

Leu His Asp Tyr Cys Asp Ile Ile Lys His Pro Met Asp Met Ser Thr
385                 390                 395                 400

Ile Lys Ser Lys Leu Glu Ala Arg Glu Tyr Arg Asp Ala Gln Glu Phe
                405                 410                 415

Gly Ala Asp Val Arg Leu Met Phe Ser Asn Cys Tyr Lys Tyr Asn Pro
            420                 425                 430

Pro Asp His Glu Val Val Ala Met Ala Arg Lys Leu Gln Asp Val Phe
        435                 440                 445

Glu Met Arg Phe Ala Lys Met Pro Asp Glu Pro Glu Glu Pro Val Val
    450                 455                 460

Ala Val Ser Ser Pro Ala Val Pro Pro Thr Lys Val Val Ala Pro
465                 470                 475                 480

Pro Ser Ser Ser Asp Ser Ser Asp Ser Ser Ser Asp Ser Asp Ser
                485                 490                 495

Ser Thr Asp Asp Ser Glu Glu Glu Arg Ala Gln Arg Leu Ala Glu Leu
            500                 505                 510

Gln Glu Gln Leu Lys Ala Val His Glu Gln Leu Ala Ala Leu Ser Gln
        515                 520                 525

Pro Gln Gln Asn Lys Pro Lys Lys Glu Lys Asp Lys Lys Glu Lys
    530                 535                 540

Lys Lys Glu Lys His Lys Arg Lys Glu Glu Val Glu Glu Asn Lys Lys
545                 550                 555                 560

Ser Lys Ala Lys Glu Pro Pro Lys Lys Thr Lys Lys Asn Asn Ser
```

```
                    565                 570                 575
Ser Asn Ser Asn Val Ser Lys Lys Glu Pro Ala Pro Met Lys Ser Lys
                580                 585                 590

Pro Pro Pro Thr Tyr Glu Ser Glu Glu Glu Asp Lys Cys Lys Pro Met
            595                 600                 605

Ser Tyr Glu Glu Lys Arg Gln Leu Ser Leu Asp Ile Asn Lys Leu Pro
        610                 615                 620

Gly Glu Lys Leu Gly Arg Val Val His Ile Ile Gln Ser Arg Glu Pro
625                 630                 635                 640

Ser Leu Lys Asn Ser Asn Pro Asp Glu Ile Glu Ile Asp Phe Glu Thr
                645                 650                 655

Leu Lys Pro Ser Thr Leu Arg Glu Leu Glu Arg Tyr Val Thr Ser Cys
            660                 665                 670

Leu Arg Lys Lys Arg Lys Pro Gln Ala Glu Lys Val Asp Val Ile Ala
        675                 680                 685

Gly Ser Ser Lys Met Lys Gly Phe Ser Ser Glu Ser Glu Ser Ser
690                 695                 700

Ser Glu Ser Ser Ser Ser Asp Ser Glu Asp Ser Glu Thr Gly
705                 710                 715
```

<210> SEQ ID NO 2
<211> LENGTH: 12
<212> TYPE: DNA
<213> ORGANISM: Artificial Sequence
<220> FEATURE:
<223> OTHER INFORMATION: synthetic

<400> SEQUENCE: 2
ttcttcttct tc                                                    12

<210> SEQ ID NO 3
<211> LENGTH: 15
<212> TYPE: DNA
<213> ORGANISM: Artificial Sequence
<220> FEATURE:
<223> OTHER INFORMATION: synthetic

<400> SEQUENCE: 3
ttcttcttct tcttc                                                 15

<210> SEQ ID NO 4
<211> LENGTH: 18
<212> TYPE: DNA
<213> ORGANISM: Artificial Sequence
<220> FEATURE:
<223> OTHER INFORMATION: synthetic

<400> SEQUENCE: 4
ttcttcttct tcttcttc                                              18

<210> SEQ ID NO 5
<211> LENGTH: 21
<212> TYPE: DNA
<213> ORGANISM: Artificial Sequence
<220> FEATURE:
<223> OTHER INFORMATION: synthetic

<400> SEQUENCE: 5
ttcttcttct tcttcttctt c                                          21

<210> SEQ ID NO 6

```
<211> LENGTH: 12
<212> TYPE: DNA
<213> ORGANISM: Artificial Sequence
<220> FEATURE:
<223> OTHER INFORMATION: synthetic

<400> SEQUENCE: 6
gaagaagaag aa                                                          12

<210> SEQ ID NO 7
<211> LENGTH: 15
<212> TYPE: DNA
<213> ORGANISM: Artificial Sequence
<220> FEATURE:
<223> OTHER INFORMATION: synthetic

<400> SEQUENCE: 7
gaagaagaag aagaa                                                       15

<210> SEQ ID NO 8
<211> LENGTH: 18
<212> TYPE: DNA
<213> ORGANISM: Artificial Sequence
<220> FEATURE:
<223> OTHER INFORMATION: synthetic

<400> SEQUENCE: 8
gaagaagaag aagaagaa                                                    18

<210> SEQ ID NO 9
<211> LENGTH: 21
<212> TYPE: DNA
<213> ORGANISM: Artificial Sequence
<220> FEATURE:
<223> OTHER INFORMATION: synthetic

<400> SEQUENCE: 9
gaagaagaag aagaagaaga a                                                21

<210> SEQ ID NO 10
<211> LENGTH: 12
<212> TYPE: RNA
<213> ORGANISM: Artificial Sequence
<220> FEATURE:
<223> OTHER INFORMATION: synthetic

<400> SEQUENCE: 10
cuucuucuuc uu                                                          12

<210> SEQ ID NO 11
<211> LENGTH: 15
<212> TYPE: RNA
<213> ORGANISM: Artificial Sequence
<220> FEATURE:
<223> OTHER INFORMATION: synthetic

<400> SEQUENCE: 11
cuucuucuuc uucuu                                                       15

<210> SEQ ID NO 12
<211> LENGTH: 18
<212> TYPE: RNA
<213> ORGANISM: Artificial Sequence
<220> FEATURE:
<223> OTHER INFORMATION: synthetic

<400> SEQUENCE: 12
```
cuucuucuuc uucuucuu                                                      18

<210> SEQ ID NO 13
<211> LENGTH: 21
<212> TYPE: RNA
<213> ORGANISM: Artificial Sequence
<220> FEATURE:
<223> OTHER INFORMATION: synthetic

<400> SEQUENCE: 13
cuucuucuuc uucuucuucu u                                                  21

<210> SEQ ID NO 14
<211> LENGTH: 6
<212> TYPE: PRT
<213> ORGANISM: Artificial Sequence
<220> FEATURE:
<223> OTHER INFORMATION: synthetic

<400> SEQUENCE: 14

Gly Ser Gly Gly Ser Gly
1               5

<210> SEQ ID NO 15
<211> LENGTH: 6
<212> TYPE: PRT
<213> ORGANISM: Artificial Sequence
<220> FEATURE:
<223> OTHER INFORMATION: synthetic

<400> SEQUENCE: 15

Gly Gly Ser Gly Gly Ser
1               5

<210> SEQ ID NO 16
<211> LENGTH: 21
<212> TYPE: DNA
<213> ORGANISM: Artificial Sequence
<220> FEATURE:
<223> OTHER INFORMATION: synthetic

<400> SEQUENCE: 16
ccactcacag actctcacaa c                                                  21

<210> SEQ ID NO 17
<211> LENGTH: 21
<212> TYPE: DNA
<213> ORGANISM: Artificial Sequence
<220> FEATURE:
<223> OTHER INFORMATION: synthetic

<400> SEQUENCE: 17
ctgcggtaca atcccagaac t                                                  21

<210> SEQ ID NO 18
<211> LENGTH: 20
<212> TYPE: DNA
<213> ORGANISM: Artificial Sequence
<220> FEATURE:
<223> OTHER INFORMATION: synthetic

<400> SEQUENCE: 18
agccagattt gcttgtttgg                                                    20

<210> SEQ ID NO 19

```
<211> LENGTH: 20
<212> TYPE: DNA
<213> ORGANISM: Artificial Sequence
<220> FEATURE:
<223> OTHER INFORMATION: synthetic

<400> SEQUENCE: 19
cagaggaaac gctggactct                                                    20

<210> SEQ ID NO 20
<211> LENGTH: 18
<212> TYPE: DNA
<213> ORGANISM: Artificial Sequence
<220> FEATURE:
<223> OTHER INFORMATION: synthetic

<400> SEQUENCE: 20
ccagcgcatc ggtcctat                                                      18

<210> SEQ ID NO 21
<211> LENGTH: 23
<212> TYPE: DNA
<213> ORGANISM: Artificial Sequence
<220> FEATURE:
<223> OTHER INFORMATION: synthetic

<400> SEQUENCE: 21
cttcctgcac caagtaaaga agt                                                23

<210> SEQ ID NO 22
<211> LENGTH: 9
<212> TYPE: PRT
<213> ORGANISM: Artificial Sequence
<220> FEATURE:
<223> OTHER INFORMATION: synthetic

<400> SEQUENCE: 22

Gly Ser Gly Gly Ser Gly Gly Ser Gly
1               5

<210> SEQ ID NO 23
<211> LENGTH: 12
<212> TYPE: PRT
<213> ORGANISM: Artificial Sequence
<220> FEATURE:
<223> OTHER INFORMATION: synthetic

<400> SEQUENCE: 23

Gly Ser Gly Gly Ser Gly Gly Ser Gly Gly Ser Gly
1               5                   10

<210> SEQ ID NO 24
<211> LENGTH: 15
<212> TYPE: PRT
<213> ORGANISM: Artificial Sequence
<220> FEATURE:
<223> OTHER INFORMATION: synthetic

<400> SEQUENCE: 24

Gly Ser Gly Gly Ser Gly Gly Ser Gly Gly Ser Gly Gly Ser Gly
1               5                   10                  15

<210> SEQ ID NO 25
<211> LENGTH: 18
<212> TYPE: PRT
<213> ORGANISM: Artificial Sequence
<220> FEATURE:
```

```
<223> OTHER INFORMATION: synthetic

<400> SEQUENCE: 25

Gly Ser Gly Gly Ser Gly Gly Ser Gly Gly Ser Gly Gly Ser Gly Gly
1               5                   10                  15

Ser Gly

<210> SEQ ID NO 26
<211> LENGTH: 21
<212> TYPE: PRT
<213> ORGANISM: Artificial Sequence
<220> FEATURE:
<223> OTHER INFORMATION: synthetic

<400> SEQUENCE: 26

Gly Ser Gly Gly Ser Gly Gly Ser Gly Gly Ser Gly Gly Ser Gly Gly
1               5                   10                  15

Ser Gly Gly Ser Gly
            20

<210> SEQ ID NO 27
<211> LENGTH: 24
<212> TYPE: PRT
<213> ORGANISM: Artificial Sequence
<220> FEATURE:
<223> OTHER INFORMATION: synthetic

<400> SEQUENCE: 27

Gly Ser Gly Gly Ser Gly Gly Ser Gly Gly Ser Gly Gly Ser Gly Gly
1               5                   10                  15

Ser Gly Gly Ser Gly Gly Ser Gly
            20

<210> SEQ ID NO 28
<211> LENGTH: 27
<212> TYPE: PRT
<213> ORGANISM: Artificial Sequence
<220> FEATURE:
<223> OTHER INFORMATION: synthetic

<400> SEQUENCE: 28

Gly Ser Gly Gly Ser Gly Gly Ser Gly Gly Ser Gly Gly Ser Gly Gly
1               5                   10                  15

Ser Gly Gly Ser Gly Gly Ser Gly Gly Ser Gly
            20                  25

<210> SEQ ID NO 29
<211> LENGTH: 30
<212> TYPE: PRT
<213> ORGANISM: Artificial Sequence
<220> FEATURE:
<223> OTHER INFORMATION: synthetic

<400> SEQUENCE: 29

Gly Ser Gly Gly Ser Gly Gly Ser Gly Gly Ser Gly Gly Ser Gly Gly
1               5                   10                  15

Ser Gly Gly Ser Gly Gly Ser Gly Gly Ser Gly Gly Ser Gly
            20                  25                  30

<210> SEQ ID NO 30
<211> LENGTH: 9
<212> TYPE: PRT
<213> ORGANISM: Artificial Sequence
<220> FEATURE:
```

```
<223> OTHER INFORMATION: synthetic

<400> SEQUENCE: 30

Gly Gly Ser Gly Gly Ser Gly Gly Ser
1               5

<210> SEQ ID NO 31
<211> LENGTH: 12
<212> TYPE: PRT
<213> ORGANISM: Artificial Sequence
<220> FEATURE:
<223> OTHER INFORMATION: synthetic

<400> SEQUENCE: 31

Gly Gly Ser Gly Gly Ser Gly Gly Ser Gly Gly Ser
1               5                   10

<210> SEQ ID NO 32
<211> LENGTH: 15
<212> TYPE: PRT
<213> ORGANISM: Artificial Sequence
<220> FEATURE:
<223> OTHER INFORMATION: synthetic

<400> SEQUENCE: 32

Gly Gly Ser Gly Gly Ser Gly Gly Ser Gly Gly Ser Gly Gly Ser
1               5                   10                  15

<210> SEQ ID NO 33
<211> LENGTH: 18
<212> TYPE: PRT
<213> ORGANISM: Artificial Sequence
<220> FEATURE:
<223> OTHER INFORMATION: syntehtic

<400> SEQUENCE: 33

Gly Gly Ser Gly Gly Ser Gly Gly Ser Gly Gly Ser Gly Gly Ser Gly
1               5                   10                  15

Gly Ser

<210> SEQ ID NO 34
<211> LENGTH: 21
<212> TYPE: PRT
<213> ORGANISM: Artificial Sequence
<220> FEATURE:
<223> OTHER INFORMATION: synthetic

<400> SEQUENCE: 34

Gly Gly Ser Gly Gly Ser Gly Gly Ser Gly Gly Ser Gly Gly Ser Gly
1               5                   10                  15

Gly Ser Gly Gly Ser
            20

<210> SEQ ID NO 35
<211> LENGTH: 24
<212> TYPE: PRT
<213> ORGANISM: Artificial Sequence
<220> FEATURE:
<223> OTHER INFORMATION: synthetic

<400> SEQUENCE: 35

Gly Gly Ser Gly Gly Ser Gly Gly Ser Gly Gly Ser Gly Gly Ser Gly
1               5                   10                  15

Gly Ser Gly Gly Ser Gly Gly Ser
            20
```

```
<210> SEQ ID NO 36
<211> LENGTH: 27
<212> TYPE: PRT
<213> ORGANISM: Artificial Sequence
<220> FEATURE:
<223> OTHER INFORMATION: synthetic

<400> SEQUENCE: 36

Gly Gly Ser Gly Gly Ser Gly Gly Ser Gly Gly Ser Gly Gly Ser Gly
1               5                   10                  15

Gly Ser Gly Gly Ser Gly Gly Ser Gly Gly Ser
            20                  25

<210> SEQ ID NO 37
<211> LENGTH: 30
<212> TYPE: PRT
<213> ORGANISM: Artificial Sequence
<220> FEATURE:
<223> OTHER INFORMATION: synthetic

<400> SEQUENCE: 37

Gly Gly Ser Gly Gly Ser Gly Gly Ser Gly Gly Ser Gly Gly Ser Gly
1               5                   10                  15

Gly Ser Gly Gly Ser Gly Gly Ser Gly Gly Ser Gly Gly Ser
            20                  25                  30
```